United States Patent
Gao et al.

(10) Patent No.: US 10,557,146 B2
(45) Date of Patent: Feb. 11, 2020

(54) MODIFIED PLANTS

(71) Applicant: The Institute of Genetics and Developmental Biology, Chinese Academy of Sciences, Beijing (CN)

(72) Inventors: Caixia Gao, Beijing (CN); Yanpeng Wang, Beijing (CN); Jin-Long Qiu, Beijing (CN)

(73) Assignee: THE INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 15/113,267

(22) PCT Filed: Jun. 27, 2014

(86) PCT No.: PCT/CN2014/080995
§ 371 (c)(1),
(2) Date: Jul. 22, 2016

(87) PCT Pub. No.: WO2015/109752
PCT Pub. Date: Jul. 30, 2015

(65) Prior Publication Data
US 2017/0114361 A1 Apr. 27, 2017

(30) Foreign Application Priority Data
Jan. 21, 2014 (CN) .......................... 2014 1 0027631

(51) Int. Cl.
*C12N 15/82* (2006.01)
*C12Q 1/6895* (2018.01)
(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
CPC .. A01H 5/10; C12N 15/8242; C12N 15/8255; C12N 15/8262; C12N 15/8277
See application file for complete search history.

(56) References Cited

U.S. PATENT DOCUMENTS

2012/0284813 A1* 11/2012 Olivier ..................... A01H 1/04
800/260
2013/0212729 A1* 8/2013 Clark ........................ A01H 5/10
800/263

FOREIGN PATENT DOCUMENTS

CN    1231673 A    10/1999
CN    1293711 A     5/2001
(Continued)

OTHER PUBLICATIONS

Cermak, Tomas, et al. "Efficient design and assembly of custom TALEN and other TAL effector-based constructs for DNA targeting." Nucleic acids research 39.12 (2011): e82-e82.*
(Continued)

*Primary Examiner* — Weihua Fan
(74) *Attorney, Agent, or Firm* — Greer, Burns & Crain, Ltd.

(57) ABSTRACT

The present invention provides a mutant wheat plant resistant to powdery mildew and producing method thereof, wherein the mutant wheat plant comprises a loss of function mutation in a TaMLO-A1, TaMLO-B1 and TaMLO-D1 nucleic acid sequence. The present invention also provides a method for determining the presence or absence of a mutant TaMLO-A1, TaMLO-B1 and TaMLO-D1 nucleic acid or polypeptide in a wheat plant.

27 Claims, 14 Drawing Sheets
Specification includes a Sequence Listing.

(56) References Cited

FOREIGN PATENT DOCUMENTS

| CN | 103343120 A | 10/2013 | | |
|---|---|---|---|---|
| CN | 102649811 B | 4/2014 | | |
| WO | WO-2000078799 A2 | * | 6/2000 | ......... C12N 15/8242 |
| WO | WO 00/78799 | * | 12/2000 | ............. C07K 14/00 |
| WO | WO-2000078799 A2 | * | 12/2000 | ............. C07K 14/00 |
| WO | WO2000078799 A3 | * | 12/2000 | ............. C07K 14/00 |

OTHER PUBLICATIONS

Sato, Kazuhiro, et al. "Development of 5006 full-length cDNAs in barley: a tool for accessing cereal genomics resources." DNA research 16.2 (2009): 81-89.*

Li, Ting, et al. "High-efficiency TALEN-based gene editing produces disease-resistant rice." Nature biotechnology 30.5 (2012): 390-392.*

Upadhyay, Santosh Kumar, et al. "RNA-guided genome editing for target gene mutations in wheat." G3: Genes, Genomes, Genetics 3.12 (2013): 2233-2238.*

Cermak, Tomas, et al. "Efficient design and assembly of custom TALEN and other TAL effector-based constructs for DNA targeting." Nucleic acids research 39.12 (2011): e82-e82. (Year: 2011).*

Sato, Kazuhiro, et al. "Development of 5006 full-length cDNAs in barley: a tool for accessing cereal genomics resources." DNA research 16.2 (2009): 81-89. (Year: 2009).*

Li, Ting, et al. "High-efficiency TALEN-based gene editing produces disease-resistant rice." Nature biotechnology 30.5 (2012): 390-392. (Year: 2012).*

Upadhyay, Santosh Kumar, et al. "RNA-guided genome editing for target gene mutations in wheat." G3: Genes, Genomes, Genetics 3.12 (2013): 2233-2238. (Year: 2013).*

Belhaj, Khaoula, et al. "Plant genome editing made easy: targeted mutagenesis in model and crop plants using the CRISPR/Cas systenn." Plant methods 9.1 (2013): 39. (Year: 2013).*

Elliott, Candace, et al. "Functional conservation of wheat and rice Mlo orthologs in defense modulation to the powdery mildew fungus." Molecular plant-microbe interactions 15.10 (2002): 1069-1077. (Year: 2002).*

Várallyay, Éva, Gábor Giczey, and József Burgyán. "Virus-induced gene silencing of Mlo genes induces powdery mildew resistance in Triticum aestivum." Archives of virology 157.7 (2012): 1345-1350. (Year: 2012).*

Gupta, P. K., et al. "Molecular markers and their applications in wheat breeding." Plant breeding 118.5 (1999): 369-390. (Year: 1999).*

Akhunov, Eduard, Charles Nicolet, and Jan Dvorak. "Single nucleotide polymorphism genotyping in polyploid wheat with the Illumina GoldenGate assay." Theoretical and Applied Genetics 119.3 (2009): 507-517. (Year: 2009).*

Piffanelli, Pietro, et al. "A barley cultivation-associated polymorphism conveys resistance to powdery mildew." Nature 430.7002 (2004): 887. (Year: 2004).*

Paris, M., et al. "Typing Mlo alleles for powdery mildew resistance in barley by single nucleotide polymorphism analysis using MALDI-ToF mass spectrometry." Australian journal of agricultural research 54.12 (2003): 1343-1349. (Year: 2003).*

Tacconi, G., et al. "Haplotype characterization and markers at the barley Mlo powdery mildew resistance locus as tools for marker-assisted selection." Genome 49.8 (2006): 864-872. (Year: 2006).*

The Institute of Genetics and Development Biology Chinese Academy of Sciences, PCT/CN2014/080995 filed on Jun. 27, 2014, "International Search Report" dated Jan. 21, 2014.

Elliott, et al., "Functional Conservation of Wheat and Rice Mlo Orthologs in Defense Modulation to the Powdery Mildew Fungus", The American Phytopathological Society, vol. 15, No. 10, pp. 1069-1077 (2002).

Niu, et al., "Molecular Basis of Powdery Mildew Resistance in Wheat (*Triticum aestivum* L.)", African Journal of Biotechnology, vol. 8, (19), pp. 4708-4716 (2009).

Konishi, Shogo et al., "Identification of Novel Mlo Family Members in Wheat and Their Genetic Characterization", Genes Genet. Syst. (2010) vol. 85, pp. 167-175. Aug. 31, 2010.

Wang, Yanpeng et al., "Simultaneous Editing of Three Homoeoalleles in Hexaploid Bread Wheat Confers Heritable Resistance to Powdery Mildew", Nature Biotechnology, vol. 32, No. 9, pp. 947-952. Sep. 2014.

Yahiaoui, Nabila et al., "Independent Evolution of Functional Pm3 Resistance Genes in Wild Tetraploid Wheat and Domesticated Bread Wheat", The Plant Journal, (2009), vol. 57, pp. 846-856. Dec. 9, 2008.

Response to 10A PC 927405AU Mar. 8, 2018.

Response to Office Action—PC927405EP dated Feb. 20, 2018.

Shan, Qiwei, et al., "Targeted Genome Modification of Crop Plants Using a CRISPR-Cas System", Nature Biotechnology, vol. 31, No. 8, pp. 686-688. Aug. 2013.

Feldman, Moshe, et al., "Genomic Asymmetry in Allopolyploid Plants: Wheat as a Model", Journal of Experimental Botany, vol. 63, No. 14, pp. 5045-5059. Jun. 6, 2012.

* cited by examiner

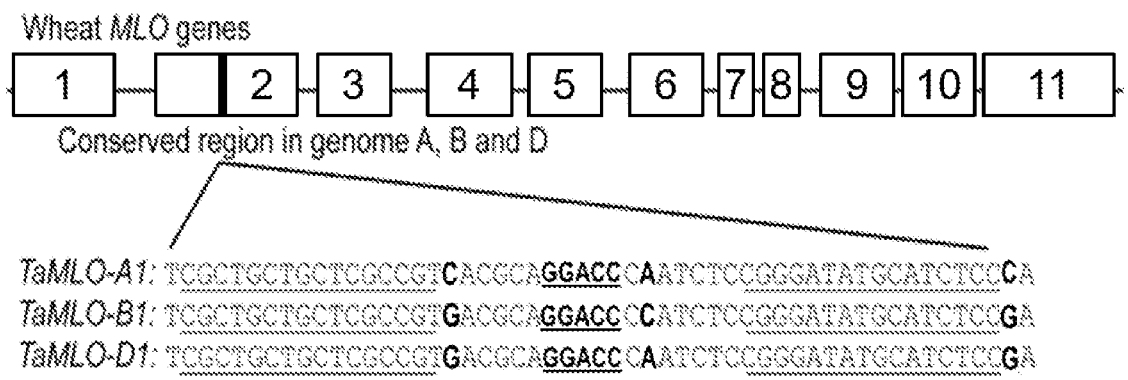

Figure 1A

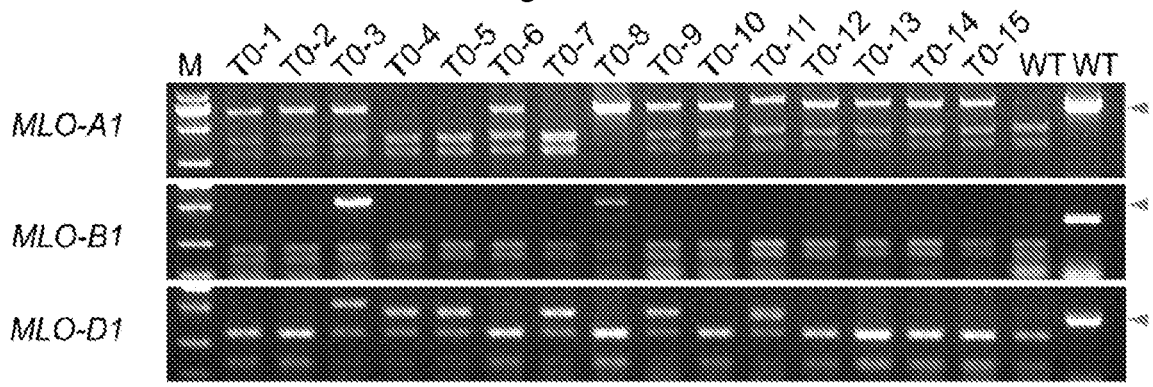

Figure 1B

```
T0-1 A1:  TCGCTGCTGCTCGCCGTcacg.....................TATGCATCTCCCA   -19
T0-2 A1:  TCGCTGCTGCTCGCCGTcacgcagga...aatctcCGGGATATGCATCTCCCA     -3
T0-3 A1:  ...........................caatctcCGGGATATGCATCTCCCA    -32
     B1:  TCGCTGCTGCTCGCCGTgacgcagga/cccoatctcCGGGATATGCATCTCCGA  +141
     D1:  TCGCTGCTGCTCGCCGTgacgcagga............/GGATATGCATCTCCGA -11/+81
T0-4 D1:  TCGCTGCTGCTCGCCGTgacgcagg.....atctcCGGGATATGCATCTCCGA     -5
T0-5 D1:  TCGCTGCTGCTCGCCGTgacgcag......aatctcCGGGATATGCATCTCCGA    -5
T0-6 A1:  TCGCTGCTGCTCGCCGTgacgca.......aatctcCGGGATATGCATCTCCGA    -6
          TCGCTGCTGCTCGCCGTcacgcagga...aatctcCGGGATATGCATCTCCCA    -3
          TCGCTGCTGCTCGCCGTcacgcagga....atctcCGGGATATGCATCTCCCA    -4
          TCGCTGCTGCTCGCCGTcacgcaggac..aatctcCGGGATATGCATCTCCCA    -2
T0-7 D1:  TCGCTGCTGCTCGCCGTgacgcaggac..aatctcCGGGATATGCATCTCCGA     -2
T0-8 A1:  TCGCTGCTGCTCGCCGTcacgcag.......tctcCGGGATATGCATCTCCCA     -7
          TCGCTGCTGCTCGCCGTcacgcagg...caatctcCGGGATATGCATCTCCCA    -3
     B1:  TCGCTGCTGCTCGCCGTgacgcagg../cccatctCCGGGATATGCATCTCCGA -2/+113
T0-9 A1:  TCGCTGCTGCTCGCCGTcacg..........tctcCGGGATATGCATCTCCCA    -10
     D1:  TCGCTGCTGCTCGCCGTgacgcaggac.....ctcCGGGATATGCATCTCCGA    -5
          TCGCTGCTGCTCGCCGTgacgcaggac....tctcCGGGATATGCATCTCCGA    -4
          TCGCTGCTGCTCGCCGTgacgcaggac..aatctcCGGGATATGCATCTCCGA    -2
T0-10 A1: TCGCTGCTGCTCGCCGTcacg..........ctcCGGGATATGCATCTCCCA    -11
T0-11 A1: TCGCTGCTGCTCGCCGTcacg.../gacccaatctcCGGGATATGCATCTCCCA -3/+61
      D1: TCGCTGCTGCTC..........................CATCTCCGA        -29
T0-12 A1: TCGCTGCCGCTCGCCGTcacgc........atctcCGGGATATGCATCTCCCA    -8
T0-13 A1: TCGCTGCCGCTCGCCGTcacgcagga......ctcCGGGATATGCATCTCCCA    -6
T0-14 A1: TCGCTGCCGCTCGCCGTcacgc......aatctcCGGGATATGCATCTCCCA     -7
T0-15 A1: TCGCTGCCGCTCGCCGTcacgca..........cCGGGATATGCATCTCCCA    -11
```

Figure 1C

Figure 4A

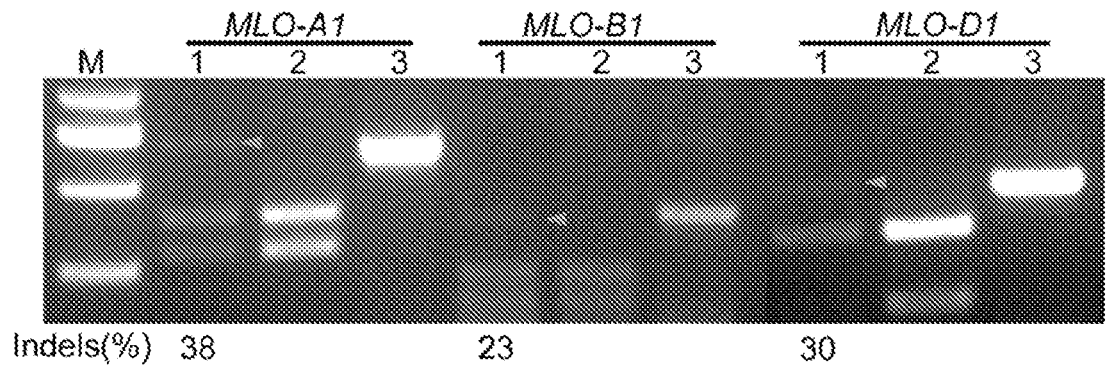

Indels(%)   38            23            30

Figure 4B

*MLO-A1*
WT: TCGCTGCTGCTCGCCGTcacgcaggacccaatctccGGGATATGCATCTCCCA
M1: TCGCTGCTGCTCGCCGTcacgcagg....aatctccGGGATATGCATCTCCCA  −4
M2: TCGCTGCTGCTCGCCGTcacgcagga...aatctccGGGATATGCATCTCCCA  −3
M3: TCGCTGCTGCTCGCCGTcacgcagacc.caatctccGGGATATGCATCTCCCA  −1
M4: TCGCTGCTGCTCGCCGTcacgcagga...aatctccGGGATATGCATCTCCCA  −3
M5: TCGCTGCTGCTCGCCGTcacgcag....caatctccGGGATATGCATCTCCCA  −4

*MLO-B1*
WT: TCGCTGCTGCTCGCCGTgacgcaggacccatctccGGGATATGCATCTCCGA
M1: TCGCTGCTGCTCGCCGTgacgca......catctccGGGATATGCATCTCCGA  −6
M2: TCGCTGCTGCTCGCCGTgacgca...ccccatctccGGGATATGCATCTCCGA  −3
M3: TCGCTGCTGCTCGCCGTgacgca.......atctccGGGATATGCATCTCCGA  −7
M4: TCGCTGCTGCTCGCCGTgacgcag....ccatctccGGGATATGCATCTCCGA  −4
M5: TCGCTGCTACTCGCCGTgacgcaggc....atctccGGGATATGCATCTCCGA  −4

*MLO-D1*
WT: TCGCTGCTGCTCGCCGTgacgcaggacccaatctccGGGATATGCATCTCCGA
M1: TCGCTGCTGCTCGCCGTgacgcagga....atctccGGGATATGCATCTCCGA  −4
M2: TCGCTGCTGCTCGCCGTgacgca.......atctccGGGATATGCATCTCCGA  −7
M3: TCGCTGCTGCTCGCCGTgacgcaggc........./cGGGATATGCATCTCCGA  −9/+92

Figure 4C

*tamlo-aa*: (T1 plants from one selfing of T0 line T0-9)
a: TCGCTGCTGCTCGCCGTcacg..........tctcCGGGATATGCATCTCCCA  −10

*tamlo-bb*: (T2 plants from two selfings of T0 line T0-8)
b: TCGCTGCTGCTCGCCGTgacgcagg../cccatctCGGGATATGCATCTCCGA  −2/+113

*tamlo-dd*: (T1 plants from one selfing of T0 line T0-7)
d: TCGCTGCTGCTCGCCGTgacgcaggac..aatctcCGGGATATGCATCTCCGA  −2

*tamlo-aabb*: (T2 plants from two selfings of T0 line T0-8)
a: TCGCTGCTGCTCGCCGTcacgcag.......tctcCGGGATATGCATCTCCCA  −7
b: TCGCTGCTGCTCGCCGTgacgcagg../cccatctCGGGATATGCATCTCCGA  −2/+113

*tamlo-aadd*: (T1 plants from one selfing of T0 line T0-11)
a: TCGCTGCTGCTCGCCGTcacgc.../acccaatctcCGGGATATGCATCTCCCA  −3/+61
d: TCGCTGCTGCTC.....................CATCTCCGA  −29

*tamlo-bbdd*: (T2 plants from two selfings of T0 line T0-3)
b:  TCGCTGCTGCTCGCCGTgacgcagga/cccatctcCGGGATATGCATCTCCGA  +141
d:  TCGCTGCTGCTCGCCGTgacgcagga........../GGATATGCATCTCCGA  −11/+81

*tamlo-aabbdd*: (T2 plants from two selfings of T0 line T0-3)
a: ............................caatctcCGGGATATGCATCTCCCA  −32
b:  TCGCTGCTGCTCGCCGTgacgcagga/cccatctcCGGGATATGCATCTCCGA  +141
d:  TCGCTGCTGCTCGCCGTgacgcagga........../GGATATGCATCTCCGA  −11/+81

Figure 5

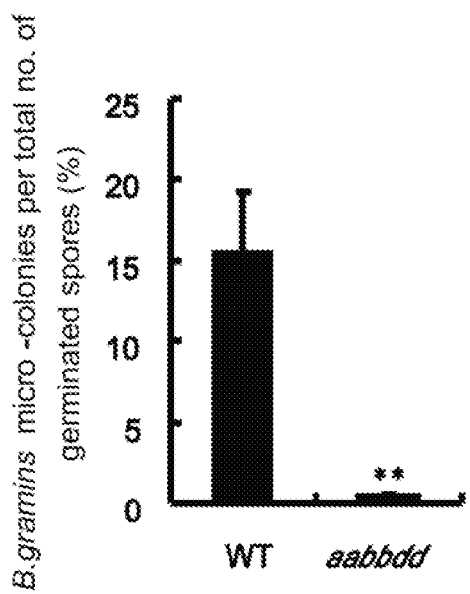

Figure 6A

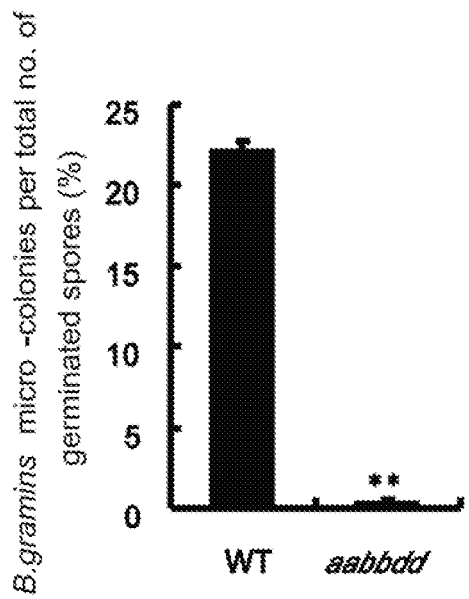

Figure 6B

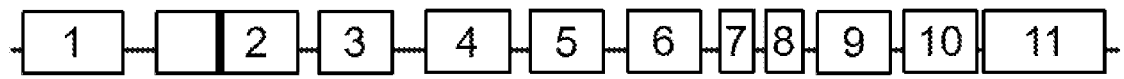

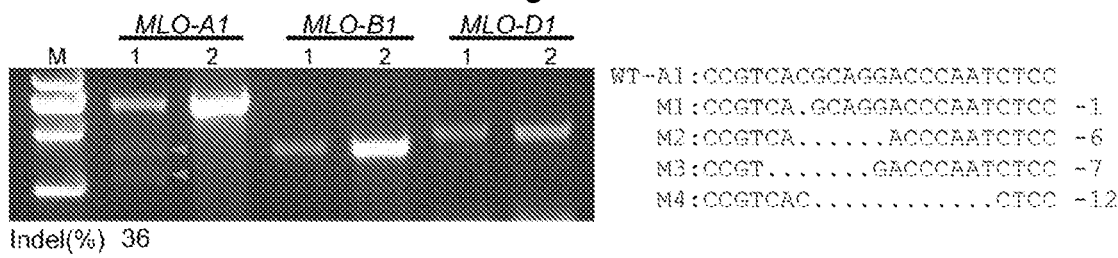

Figure 7A

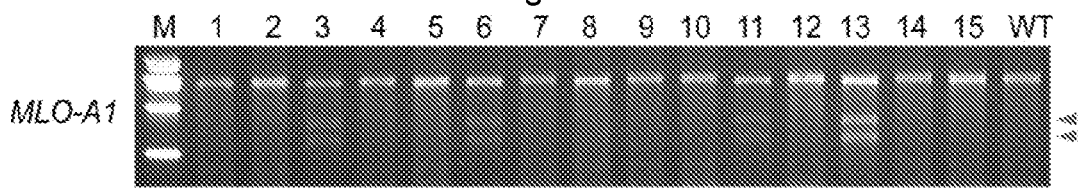

Figure 7B

```
MLO-A1:  TCGCTGCTGCTCGCCGTCACGCAGGACCCAATCTCCGGATATGCATCTCCCA
   M3:   TCGCTGCTGCTCGCCGTCA...AGGACCcAATCTCCGGATATGCATCTCCCA   -3
   M6:   TCGCTGCTGCTCGCCGTCA.gCAGGACCcAATCTCCGGATATGCATCTCCCA   -1
   M11:  TCGCTGCTGCTCGCCGTCA....GGACCcAATCTCCGGATATGCATCTCCCA   -4
   M13:  TCGCTGCTGCTCGCCGTCATCGCAGGACCCAATCTCCGGATATGCATCTCCCA  +1
```

Figure 7C

```
TCGCTGCTGCTCGCCGTGACGCAGGACCCCATCTCCGGGATATGCATCTCCGAaagcttgtcgacggatccatggtgagcaagggcgaggagct
gttcaccggggtggtgcccatcctggtcgagctggacggcgacgtaaacggccacaagttcagcgtgtccggcgagggcgagggcgatgccacc
tacggcaagctgaccctgaagttcatctgcaccaccggcaagctgcccgtgccctggcccaccctcgtgaccaccttcacctacggcgtgcagt
gcttcagccgctaccccgaccacatgaagcagcacgacttcttcaagtccgccatgcccgaaggctacgtccaggagcgcaccatcttcttcaa
ggacgacggcaactacaagacccgcgccgaggtgaagttcgagggcgacaccctggtgaaccgcatcgagctgaagggcatcgacttcaaggag
gacggcaacatcctggggcacaagctggagtacaactacaacagccacaacgtctatatcatggccgacaagcagaagaacggcatcaaggtga
acttcaagatccgccacaacatcgaggacggcagcgtgcagctcgccgaccactaccagcagaacacccccatcggcgacggccccgtgctgct
gcccgacaaccactacctgagcacccagtccgccctgagcaaagacccccaacgagaagcgcgatcacatggtcctgctggagttcgtgaccgcc
gccgggatcactcacggcatggacgagctgtacaagtaaccgggcgagctcgaattcgctgaaatcaccagtctctctctctacaaatctatctct
ctctattttctccataaataatgtgtgagtagtttcccgataagggaaattagggttcttatagggtttcgctcatgtgttgagcatataagaa
acccttagtatgtatttgtatttgtaaaatacttctatcaataaaattctaattcctaaaaccaaaatccagtactaaaatccagatctccta
aagtccctatagatctttgtcgtgaatatataaaccagacacgagacgactaaacctggagcccagacgccgttcgaagctagaagtaccgcttag
gcaggaggccgttagggaaaagatgctaaggcagggttggttacgttgactccccgtaggtttggtttaaatatgatgaagtggacggaagga
aggaggaagacaaggaaggataaggttgcaggccctgtgcaaggtaagaagatggaaatttgatagaggtacgctactatacttatactatacg
ctaagggaatgcttgtatttataccctatacccctaataaccccttatcaatttaagaaataatccgcataagccccgcttaaaaattggta
tcagagccatgaataggtctatgaccaaaactcaagaggataaaacctcaccaaaatacgaaagagttcttaactctaaagataaaagatcttt
caagatcaaaactagttccctcacaccggtgacgggatcgcatgcgatTCGCTGCTGCTCGCCGTGACGCAGGACCCCATCTCCGGGATATGC
ATCTCCGA
```

Figure 8 tcgtgcccctctctagagataatgagcattgcatgtctaagttataaaaaattaccacatattttttt
gtcacacttgtttgaagtgcagtttatctatctttatacatatatttaaactttactctacgaataata
taatctatagtactacaataatatcagtgttttagagaatcatataaatgaacagttagacatggtcta
aaggacaattgagtattttgacaacaggactctacagttttatcttttagtgtgcatgtgttctcctt
ttttttgcaaatagcttcacctatataatacttcatccatttattagtacatccatttagggtttag
ggttaatggtttttatagactaatttttttagtacatctattttattctattttagcctctaaattaag
aaaactaaaactctattttagttttttttatttaataatttagatataaaatagaataaaataaagtgac
taaaaattaaacaaatacccttaagaaattaaaaaaactaaggaaacatttttcttgtttcgagtaga
taatgccagcctgttaaacgccgtcgacgagtctaacggacaccaaccagcgaaccagcagcgtcgcgt
cgggccaagcgaagcagacggcacggcatctctgtcgctgcctctggaccctctcgatcgagagttcc
gctccaccgttggacttgctccgctgtcggcatccagaaattgcgtggcggagcggcagacgtgagccg
gcacggcaggcggcctcctcctcctctcacggcaccggcagctacggggattcctttcccaccgctcc
ttcgctttcccttcctcgcccgccgtaataaatagacacccctccacaccctctttccccaacctcgt
gttgttcggagcgcacacacacacaaccagatctcccccaaatccacccgtcggcacctccgcttcaag
gtacgccgctcgtcctcccccccccccctctctaccttctctagatcggcgttccggtccatggttag
ggcccggtagttctacttctgttcatgtttgtgttagatccgtgtttgtgttagatccgtgctgctagc
gttcgtacacggatgcgacctgtacgtcagacacgttctgattgctaacttgccagtgtttctctttgg
ggaatcctgggatggctctagccgttccgcagacgggatcgatttcatgattttttttgtttcgttgca
tagggtttggtttgccctttttcctttatttcaatatatgccgtgcacttgtttgtcgggtcatcttttc
atgcttttttttgtcttggttgtgatgatgtggtctggttgggcggtcgttctagatcggagtagaatt
aattctgtttcaaactacctggtggatttattaattttggatctgtatgtgtgtgccatacatattcat
agttacgaattgaagatgatggatggaaatatcgatctaggataggtatacatgttgatgcgggtttta
ctgatgcatatacagagatgcttttgttcgcttggttgtgatgatgtggtgtggttgggcggtcgttc
attcgttctagatcggagtagaatactgtttcaaactacctggtgtatttattaattttggaactgtat
gtgtgtgtcatacatcttcatagttacgagtttaagatggatggaaatatcgatctaggataggtatac
atgttgatgtgggttttactgatgcatatacatgatggcatatgcagcatctattcatatgctctaacc
ttgagtacctatctattataataaacaagtatgttttataattattttgatcttgatatacttggatga
tggcatatgcagcagctatatgtggattttttagccctgccttcatacgctatttatttgcttggtac
tgtttcttttgtcgatgctcaccctgttgtttggtgttacttctgcaaaagcttgccaagct*atcaaac*
*aagtttgtacaaaaaagctgaacgagaaacgtaaaatgatataaatatcaatatattaaattagattt*

Figure 9A

*gcataaaaaacagactacataatactgtaaaacacaacatatccagtcactatg*gcggccgcattaggc
accccaggctttacactttatgcttccggctcgtataatgtgtggattttgagttaggatccggcgaga
ttttcaggagctaaggaagctaaaatggagaaaaaaatcactggatataccaccgttgatatatcccaa
tggcatcgtaaagaacattttgaggcatttcagtcagttgctcaatgtacctataaccagaccgttcag
ctggatattacggccttttaaagaccgtaaagaaaaataagcacaagttttatccggcctttattcac
attcttgcccgcctgatgaatgctcatccggaattccgtatggcaatgaaagacggtgagctggtgata
tgggatagtgttcacccttgttacaccgttttccatgagcaaactgaaacgttttcatcgctctggagt
gaataccacgacgatttccggcagtttctacacatatattcgcaagatgtggcgtgttacggtgaaaac
ctggcctatttccctaaagggtttattgagaatatgttttcgtctcagccaatccctgggtgagtttc
accagttttgatttaaacgtggccaatatggacaacttcttcgcccccgttttcaccatgggcaaatat
tatacgcaaggcgacaaggtgctgatgccgctggcgattcaggttcatcatgccgtctgtgatggcttc
catgtcggcagaatgcttaatgaattacaacagtactgcgatgagtggcagggcggggcgtaatctaga
ggatccggcttactaaaagccagataacagtatgcgtatttgcgcgctgattttttgcggtataagaata
tatactgatatgtatacccgaagtatgtcaaaaagaggtgtgctatgaagcagcgtattacagtgacag
ttgacagcgacagctatcagttgctcaaggcatatatgatgtcaatatctccggtctggtaagcacaac
catgcagaatgaagcccgtcgtctgcgtgccgaacgctggaaagcggaaaatcaggaagggatggctga
ggtcgcccggtttattgaaatgaacggctcttttgctgacgagaacagggactggtgaaatgcagttta
aggtttacacctataaagagagagccgttatcgtctgtttgtggatgtacagagtgatattattgaca
cgcccgggcgacggatggtgatcccctggccagtgcacgtctgctgtcagataaagtctcccgtgaac
ttacccggtggtgcatatcggggatgaaagctggcgcatgatgaccaccgatatggccagtgtgccgg
tctccgttatcggggaagaagtggctgatctcagccaccgcgaaaatgacatcaaaaacgccattaacc
tgatgttctggggaatataaatgtcaggctcccttatacacagccagtctgcaggtcgac*catagtgac
tggatatgttgtgttttacagtattatgtagtctgttttttatgcaaaatctaatttaatatattgata
tttatatcattttacgtttctcgttcagctttcttgtacaaagtgg*tcgataattccttaattaacta
gttctagagcggccgcccaccgcggtggagctc**gaatttccccgatcgttcaaacatttggcaataaag
tttcttaagattgaatcctgttgccggtcttgcgatgattatcatataatttctgttgaattacgtta
agcatgtaataattaacatgtaatgcatgacgttatttatgagatgggttttatgattagagtcccg
caattatacatttaatacgcgatagaaaacaaaatatagcgcgcaaactaggataaattatcgcgcgc
ggtgtcatctatgtt**act

Figure 9A continued tctagaATGgtggatctacgcacgctcggctacagtcagcagcagcaagagaagatcaaaccgaaggtg
cgttcgacagtggcgcagcaccacgaggcactggtgggccatgggtttacacacgcgcatcgttgcg
ctcagccaacacccggcagcgttagggaccgtcgctgtcacgtatcagcacataatcacggcgttgcca
gaggcgacacacgaagacatcgttggcgtcggcaaacagtggtccggcgcacgcgccctggaggccttg
ctcacggatgcgggggagttgagaggtccgccgttacagttggacacaggccaacttgtgaagattgca
aaacgtggcggcgtgaccgcaatggaggcagtgcatgcatcgcgcaatgcactgacgggtgccccctg
AACCTGACCCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACGGTGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACAATGGCGGCAAGCAAGCGCTCGAAACGGT
GCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACGGTGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACGGTGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACAATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACGGTGGCGGCAAGCAAGCGCTCGAAAGCATTGTGGCCCAGCTGAGCCGGCCTGATCCGGCGTTG

Figure 9B

GCCGCGTTGAccaacgaccacctcgtcgccttggcctgcctcggcggacgtcctgccatggatgcagtg
aaaaagggattgccgcacgcgccggaattgatcagaagagtcaatcgccgtattggcgaacgcacgtcc
catcgcgttgccggatcc

Figure 9B Continued tctagaATGgtggatctacgcacgctcggctacagtcagcagcagcaagagaagatcaaaccgaaggtg
cgttcgacagtggcgcagcaccacgaggcactggtgggccatgggtttacacacgcgcacatcgttgcg
ctcagccaacacccggcagcgttagggaccgtcgctgtcacgtatcagcacataatcacggcgttgcca
gaggcgacacacgaagacatcgttggcgtcggcaaacagtggtccggcgcacgcgccctggaggccttg
ctcacggatgcgggggagttgagaggtccgccgttacagttggacacaggccaacttgtgaagattgca
aaacgtggcggcgtgaccgcaatggaggcagtgcatgcatcgcgcaatgcactgacgggtgccccctg
AACCTGACCCCGGACCAAGTGGTGGCTATCGCCAGCAACAAGGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACAAGGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACAAGGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACATTGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACAAGGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACATTGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACGGTGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACAAGGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACATTGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACGGTGGCGGCAAGCAAGCGCTCGAAACGGT
GCAGCGGCTGTTGCCGGTGCTGTGCCAGGACCATGGCCTGACCCCGGACCAAGTGGTGGCTATCGCCA
GCAACATTGGCGGCAAGCAAGCGCTCGAAACGGTGCAGCGGCTGTTGCCGGTGCTGTGCCAGGACCAT

Figure 9C

GGCCTGACCCCGGACCAAGTGGTGGCTATCGCCAGCAACGGTGGCGGCAAGCAAGCGCTCGAAACGGT
GCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAAGCAAGCGCTCGAAACGGT
GCAGCGGCTGTTGCCGGTGCTGTGCCAGGACCATGGCCTGACTCCGGACCAAGTGGTGGCTATCGCCA
GCCACGATGGCGGCAAGCAAGCGCTCGAAACGGTGCAGCGGCTGTTGCCGGTGCTGTGCCAGGACCAT
GGCCTGACCCCGGACCAAGTGGTGGCTATCGCCAGCAACAAGGGCGGCAAGCAAGCGCTCGAAAGCAT
TGTGGCCCAGCTGAGCCGGCCTGATCCGGCGTTGGCCGCGTTGAccaacgaccacctcgtcgccttggc
ctgcctcggcggacgtcctgccatggatgcagtgaaaaagggattgccgcacgcgccggaattgatcag
aagagtcaatcgccgtattggcgaacgcacgtcccatcgcgttgccggatcc

Figure 9C Continued

*Caaataatgattttatttgactgatagtgacctgttcgttgcaacaaattgatgagcaatgctttttt
ataatgccaactttgtacaaaaaagcaggct*ccgaattcgcccttcaccatggattataaggatcacga
tggcgactacaaggaccacgatattgactacaaagacgatgacgataaaatggctcctaagaaaagcg
caaagtcggtatccatggcgttccctctagaATGgtggatctacgcacgctcggctacagtcagcagca
gcaagagaagatcaaaccgaaggtgcgttcgacagtggcgcagcaccacgaggcactggtgggccatgg
gtttacacacgcgcacatcgttgcgctcagccaacacccggcagcgttagggaccgtcgctgtcacgta
tcagcacataatcacggcgttgccagaggcgacacacgaagacatcgttggcgtcggcaaacagtggtc
cggcgcacgcgccctggaggccttgctcacggatgcgggggagttgagaggtccgccgttacagttgga
cacaggccaacttgtgaagattgcaaaacgtggcggcgtgaccgcaatggaggcagtgcatgcatcgcg
caatgcactgacgggtgcccCCCTGAACCTGACCCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACAATGGCGGCAAGCAAGCGCTCGAAACGGTGCAGCGGCTG
TTGCCGGTGCTGTGCCAGGACCATGGCCTGACTCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACGGTGGCGGCAAGCAAGCGCTCGAAACGGTGCAGCGGCTG
TTGCCGGTGCTGTGCCAGGACCATGGCCTGACCCCGGACCAAGTGGTGGCTATCGCCAGCAACAATGG
CGGCAAGCAAGCGCTCGAAACGGTGCAGCGGCTGTTGCCGGTGCTGTGCCAGGACCATGGCCTGACTC
CGGACCAAGTGGTGGCTATCGCCAGCCACGATGGCGGCAAGCAAGCGCTCGAAACGGTGCAGCGGCTG
TTGCCGGTGCTGTGCCAGGACCATGGCCTGACCCCGGACCAAGTGGTGGCTATCGCCAGCAACGGTGG

Figure 9D

CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACAATGGCGGCAAGCAAGCGCTCGAAACGGTGCAGCGGCTG
TTGCCGGTGCTGTGCCAGGACCATGGCCTGACTCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACGGTGGCGGCAAGCAAGCGCTCGAAACGGTGCAGCGGCTG
TTGCCGGTGCTGTGCCAGGACCATGGCCTGACCCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACAATGGCGGCAAGCAAGCGCTCGAAACGGTGCAGCGGCTG
TTGCCGGTGCTGTGCCAGGACCATGGCCTGACTCCGGACCAAGTGGTGGCTATCGCCAGCCACGATGG
CGGCAAGCAAGCGCTCGAAACGGTGCAGCGGCTGTTGCCGGTGCTGTGCCAGGACCATGGCCTGACTC
CGGACCAAGTGGTGGCTATCGCCAGCCACGATGGCGGCAAGCAAGCGCTCGAAACGGTGCAGCGGCTG
TTGCCGGTGCTGTGCCAGGACCATGGCCTGACCCCGGACCAAGTGGTGGCTATCGCCAGCAACAATGG
CGGCAAGCAAGCGCTCGAAACGGTGCAGCGGCTGTTGCCGGTGCTGTGCCAGGACCATGGCCTGACCC
CGGACCAAGTGGTGGCTATCGCCAGCAACGGTGGCGGCAAGCAAGCGCTCGAAAGCATTGTGGCCCAG
CTGAGCCGGCCTGATCCGGCGTTGGCCGCGTTGAccaacgaccacctcgtcgccttggcctgcctcgg
cggacgtcctgccatggatgcagtgaaaaagggattgccgcacgcgccggaattgatcagaagagtca
atcgccgtattggcgaacgcacgtcccatcgcgttgccggatccCagctggtgaagtccgagctggaa
gaaaaaaagagcgagctgcgccacaagctcaagtacgtgccccacgagtacatcgagctgatcgagat
cgcccgcaacagcacccaagaccgcatcctggagatgaaagtgatggagttcttcatgaaggtgtacg
gctaccgcggcaagcacctgggcggctcccgcaagcccgatggcgccatctacaccgtgggctccccc
atcgactatggcgtcattgtcgacaccaaggcctactccggcggctacaacttacccatcggtcaggc
cgacgagatgcaacgctacgtgaaggagaaccagacccgcaataagcacattaatcccaacgagtggt
ggaaggtgtaccctcctccgtgaccgagttcaaattcctgttcgtgtccggccacttcaagggcaat
tataaggcccaactgacccgcctgaaccacaagaccaactgcaacggcgccgtgctgtccgtggagga
actgctgatcggcggcgagatgatcaaggctggtaccctgaccctggaagaggtgcgccgcaagttca
acaatggtgaaatcaatttcaggtccggcggcggaGagggcagaggaagtcttctaacatgcggtgac
gtggaggagaatcccggccctaggatggactacaaagaccatgacggtgattataaagatcatgacat
cgattacaaggatgacgatgacaagatggcccccaagaagaagaggaaggtgggcattcacggggtgc
cggctagcATGgtggatctacgcacgctcggctacagtcagcagcagcaagagaagatcaaaccgaag

Figure 9D continued gtgcgttcgacagtggcgcagcaccacgaggcactggtgggccatgggtttacacacgcgcacatcgt
tgcgctcagccaacacccggcagcgttagggaccgtcgctgtcacgtatcagcacataatcacggcgt
tgccagaggcgacacacgaagacatcgttggcgtcggcaaacagtggtccggcgcacgcgccctggag
gccttgctcacggatgcgggggagttgagaggtccgccgttacagttggacacaggccaacttgtgaa
gattgcaaaacgtggcggcgtgaccgcaatggaggcagtgcatgcatcgcgcaatgcactgacgggtg
cccCCCTGAACCTGACCCCGGACCAAGTGGTGGCTATCGCCAGCAACAAGGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACAAGGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACAAGGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACATTGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACAAGGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACATTGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACAAGGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACATTGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACCCCGGACCAAGTGGTGGC
TATCGCCAGCAACATTGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACTCCGGACCAAGTGGTGGC
TATCGCCAGCCACGATGGCGGCAAGCAAGCGCTCGAAACGGTGCAGCGGCTGTTGCCGGTGCTGTGCC
AGGACCATGGCCTGACTCCGGACCAAGTGGTGGCTATCGCCAGCCACGATGGCGGCAAGCAAGCGCTC
GAAACGGTGCAGCGGCTGTTGCCGGTGCTGTGCCAGGACCATGGCCTGACTCCGGACCAAGTGGTGGC
TATCGCCAGCCACGATGGCGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACAAGGGCGGCAAGCAAGCGCTC

Figure 9D continued

GAAAGCATTGTGGCCCAGCTGAGCCGGCCTGATCCGGCGTTGGCCGCGTTGAccaacgaccacctcgt
cgccttggcctgcctcggcggacgtcctgccatggatgcagtgaaaaagggattgccgcacgcgccgg
aattgatcagaagagtcaatcgccgtattggcgaacgcacgtcccatcgcgttgccAgatct*caacta*
*gtcaaaagtgaactggaggagaagaaatctgaacttcgtcataaattgaaatatgtgcctcatgaata*
*tattgaattaattgaaattgccagaaattccactcaggatagaattcttgaaatgaaggtaatggaat*
*tttttatgaaagtttatggatatagaggtaaacatttgggtggatcaaggaaaccggacggagcaatt*
*tatactgtcggatctcctattgattacggtgtgatcgtggatactaaagcttatagcggaggttataa*
*tctgccaattggccaagcagatgaaatggagcgatatgtcgaagaaaatcaaacacgaaacaaacatc*
*tcaaccctaatgaatggtggaaagtctatccatcttctgtaacggaatttaagttttatttgtgagt*
*ggtcactttaaaggaaactacaaagctcagcttacacgattaaatcatatcactaattgtaatggagc*
*tgttcttagtgtagaagagcttttaattggtggagaaatgattaaagccggcacattaaccttagagg*
*aagtgagacggaaatttaataacggcgagataaac*tttTAATAG

*aagggcgaattcgacccagctttcttgtacaaagttggcattataaaaaataattgctcatcaatttgt*
*tgcaacgaacaggtcactatcagtcaaaataaaatcattatttg*

Figure 9D continued

MODIFIED PLANTS

FIELD OF THE INVENTION

The present invention relates to conferring pathogen resistance in wheat plants.

INTRODUCTION

In plants, resistance to pathogens is frequently triggered by a recognition event followed by a coordinated complex defence response resulting in localized containment of the intruder.

Powdery mildew (Pm) is one of the most important cereal diseases worldwide. The powdery mildew disease, caused by obligate biotrophic ascomycete fungi of the order Erysiphales, is a major impediment for cereal (e.g. wheat and barley) agriculture in temperate climates. Powdery mildew in wheat is caused by the infection of *Blumeria graminis* f. sp. *tritici* (Bgt) (also called *Erysiphe graminis* f. sp. *tritici*).

MLO proteins function as negative regulators of plant defence to powdery mildew disease[25]. Loss-of-function mlo alleles in barley[26,40] *Arabidopsis*[27] and tomato[28] lead to broad-spectrum and durable resistance to the fungal pathogen causing powdery mildew.

Resistance responses to the powdery mildew pathogen have been genetically well characterized. In most analyzed cases resistance is specified by race-specific resistance genes following the rules of Flor's gene-for-gene hypothesis. In this type of plant-pathogen interactions, resistance is specified by and dependent on the presence of two complementary genes, one from the host and one from the fungal pathogen. The complementary genes have been termed operationally (pathogen) resistance ("R") gene and avirulence ("Avr") gene, respectively. Most of the powdery mildew resistance genes (Mix) act as dominant or semidominant traits.

However, monogenic resistance mediated by recessive (mlo) alleles of the Mlo locus is different. Apart from being recessive, it differs from race-specific resistance to single pathogen strains in that it confers broad spectrum resistance to almost all known isolates of the pathogen and mlo resistance alleles exhibit a defence mimic phenotype in the absence of the pathogen. Thus, the genetic data indicate that the Mlo wild type allele exerts a negative regulatory function on defence responses to pathogen attack (WO98/04586).

Bread wheat (*Triticum aestivum* L., 2n=42, AABBDD) is a major staple crop worldwide and provides about 20% of all calories consumed by humans. Because of its economic importance, new traits have always been sought to improve yield, quality and adaptation to biotic and abiotic stresses, mostly through classical breeding. Bread wheat is an allohexaploid, with three similar but not identical copies of most of its genes[5]. Its large genome (17,000 megabases), high ploidy level and high content of repetitive DNA (80% to 90%) make it one of the most challenging species for forward and reverse genetics studies[6].

In wheat, powdery mildew is caused by *Blumeria graminis* f. sp. *tritici* (Bgt), and is one of the most destructive diseases worldwide. Modification of MLO genes in wheat may provide the opportunity to breed varieties with broad-spectrum and durable resistance to Bgt. In bread wheat, there are three MLO homoeologs (TaMLO-A1, TaMLO-B1 and TaMLO-D1), which are 98% and 99% identical at the nucleotide and protein levels, respectively[29]. TaMLO-B1 can rescue the resistance of a barley mlo mutant to powdery mildew disease, indicating that the function of these MLO genes has been conserved during evolution[29]. However, to date, no spontaneous or and induced mlo mutants have been reported in bread wheat, probably because of its hexaploid nature and the inherent difficulty in mutating all three MLO homoeoalleles. Moreover, no successful progress has been made with transgenic approaches to downregulating MLO in wheat. Therefore, there is a significant need to develop wheat genotypes that are resistant to Pm.

Recently, genome editing techniques have emerged as alternative methods to conventional mutagenesis methods (such as physical and chemical mutagenesis) or methods using the expression of transgenes in plants to produce mutant plants with improved phenotypes that are important in agriculture. These techniques employ sequence-specific nucleases (SSNs)[1] including zinc finger nucleases (ZFNs)[7], transcription activator-like effector nucleases (TALENs[2]), and the RNA-guided nuclease Cas9 (CRISPR/Cas9)[41, 3], which generate targeted DNA double-strand breaks (DSBs), which are then repaired mainly by either error-prone non-homologous end joining (NHEJ)[8] or high-fidelity homologous recombination (HR)[1,9]. The SSNs have been used to create targeted knockout plants in various species ranging from the model plants, *Arabidopsis*[10,11] and tobacco[12], to important crops, such as barley[13,14], soybean[15], rice[16-21] and maize[22,23]. Although heritable gene modification has been demonstrated in *Arabidopsis*[10,11,24] and rice[18] using the CRISPR/Cas9 system and TALENs, germline transmission of a mutation created by such genome editing strategies has not yet been achieved in all MLO gene in hexaploid bread wheat. Only genome editing of a single MLO gene in bread wheat using a transient protoplast expression system[17] has been demonstrated.

The inventors surprisingly demonstrate herein that both TALEN and CRISPR/Cas are efficient at simultaneously mutating all three endogenous MLO wheat genes and thus producing novel stably transmitted genetic disease resistance traits in hexaploid wheat. The inventors show that TALEN-induced mutations in three TaMLO homoeologs are faithfully inherited, and that simultaneous mutation of all three TaMLO homoeologs confers broad spectrum resistance to powdery mildew, a resistance trait that has not been found in the natural wheat population[4]. Furthermore, the inventors prove the feasibility of engineering targeted DNA insertion through non-homologous end joining of the double strand breaks caused by TALENs in multiple wheat genes.

This work demonstrates for the first time that multiple homoeologous genes in a polyploidy organism can be edited simultaneously and precisely, and that these edited genes are segregating normally to the following generations. For the first time mlo-mediated disease resistance is obtained in a polyploid plant. Targeted gene mutations in wheat are particularly important as classical approaches in mutagenesis are usually not successful because of gene redundancy caused by the presence of three homoeologous gene copies on the three subgenomes of polyploid wheat.

The invention described herein is thus aimed at providing mutant wheat plants resistant to powdery mildew and related methods, thus providing products and methods of agricultural importance.

SUMMARY OF THE INVENTION

The inventors have successfully undertaken genome editing of hexaploid wheat, and in a one-step procedure obtained a long-wanted type of disease resistance.

Thus, in a first aspect, the invention relates to a mutant wheat plant comprising a loss of function mutation in a TaMLO-A1, TaMLO-B1, and/or a TaMLO-D1 nucleic acid sequence. In one embodiment, the invention relates to a mutant wheat plant comprising a loss of function mutation in a TaMLO-A1, TaMLO-B1, and a TaMLO-D1 nucleic acid sequence and said mutation confers resistance to powdery mildew In another aspect, the invention relates to an isolated mutant TaMLO-A1 comprising SED ID NO. 39.

In another aspect, the invention relates to an isolated mutant TaMLO-B1 comprising SED ID NO. 40.

In another aspect, the invention relates to an isolated mutant TaMLO-D1 comprising SED ID NO. 41.

In another aspect, the invention relates to a primer or primer pair selected from SED ID NOs. 18 to 25.

In another aspect, the invention relates to the use of a primer selected from SED ID NOs. 18 to 25 in determining the presence of a mutant TaMLO-A1, TaMLO-B1, and/or TaMLO-D1 nucleic acid in a wheat plant.

In another aspect, the invention relates to a method for producing a mutant wheat plant resistant to Pm comprising introducing a loss of function mutation into a TaMLO-A1, TaMLO-B1 and/or a TaMLO-D1 nucleic acid sequence in a mutant wheat plant using targeted genome modification.

In another aspect, the invention relates to a method for conferring resistance to powdery mildew to a wheat plant comprising producing a plant as described herein.

In another aspect, the invention relates to a detection kit for determining the presence or absence of a mutant TaMLO-A1, TaMLO-B1, and/or TaMLO-D1 nucleic acid or polypeptide in a wheat plant.

In another aspect, the invention relates to a method for determining the presence or absence of a mutant TaMLO-A1, TaMLO-B1, and/or TaMLO-D1 nucleic acid or polypeptide in a wheat plant.

In another aspect, the invention relates to a vector comprising SEQ ID NOs. 11 or 12.

In another aspect, the invention relates to a vector as shown in FIG. 9.

DESCRIPTION OF FIGURES

FIG. 1. Targeted knock-out of TaMLO genes using TALENs. (a) Sites within a conserved region of exon 2 of wheat TaMLO homoeologs targeted by TALENs. The TALEN-targeted sequences in MLO-A1, MLO-B1 and MLO-D1 are underlined, and the AvaII restriction site in the spacer is GGACC (SEQ ID NO. 38). There are three SNP s, two are in the spacer region. The first is C/G/G respectively directly adjacent to the underlined 5' region. The second is A/C/A 3' of the AvaII region following residue C directly adjacent to the AvaII region. The third one lies near the far right of the TALEN binding site (penultimate 3' residue). (b) Outcome of PCR/RE assay to detect TALEN-induced mutations in 15 representative T 0 transgenic wheat plants. Mutations were identified in TaMLO genes amplified with gene-specific primers from independent seedlings. Lanes T0-1 to T0-15, PCR fragments amplified from the transgenic wheat plants digested with AvaII. Lanes WT, PCR fragments amplified from a wild type control plant with or without AvaII digestion. The bands marked by arrowheads are caused by TALEN-induced mutations. (c) TALEN-induced mutant TaMLO alleles identified by sequencing 15 representative transgenic wheat plants. The numbers on the right show the type of mutation and how many nucleotides are involved, with "−" and "+" indicating deletion or insertion of the given number of nucleotides. SEQ ID NOS: 14-16, 48-98, 120, 131, and 142.

FIG. 4. TALEN-induced targeted mutations in TaMLO genes in wheat protoplasts. (a) The coding sequences of the two nuclease monomers are expressed from the maize Ubiquitin 1 (Ubi-1) promoter and separated by a T2A translational skipping sequence. (b) Gel of a PCR/RE assay to detect TALEN-induced mutations in TaMLO genes in wheat protoplasts. Specific primers were used to amplify TaMLO-A1, TaMLO-B1 and TaMLO-D1, respectively. Mutations occurred in all three gene sets. Lanes marked with "1", digested T-MLO-transformed protoplasts; lanes marked with "2" and "3", digested and undigested wild type controls. Red arrowheads indicate bands with mutations. The numbers at the bottom of the gel indicate indel mutation frequencies measured from the band intensities. (d) Sequences of mutations in the three MLO homoeoalleles in the protoplasts. The wild-type sequences are shown at the top of each sequence group. The numbers at the side indicate the type of mutation and how many nucleotides are involved. SEQ ID NOS: 120-148.

FIG. 5. DNA sequences of TaMLO genomic loci in various homozygous mutants. All the mutants (tamlo-aa, tamlo-bb, tamlo-dd, tamlo-aabb, tamlo-aadd, tamlo-bbdd and tamlo-aabbdd) were identified in T1 or T2 and corresponding heterozygous T0 lines are indicated in brackets. Sizes of the indels are given to the right of each sequence (+, insertion; −, deletion). All the different combinations of homozygous mutants were used to assess the impact of TALEN-induced mutations of TaMLO on wheat resistance to powdery mildew. SEQ. ID NOS: 149-171.

FIG. 6. Loss of TaMLO function confers bread wheat broad-spectrum resistance to powdery mildew. (a) Leaves of the plants challenged with virulent *Blumeria graminis* f. sp. *tritici* (Bgt) isolate E22. (b) Leaves of the plants challenged with virulent Bgt isolate B13. Percentage of micro-colonies formed from the total number of germinated spores of Bgt inoculated on the leaves of wild-type (WT) and tamlo-aabbdd (aabbdd) mutant. At least 2000 germinated spores per genotype per experiment were examined 72 hours after inoculation. Values are mean±s.d. of four independent experiments. ** $P<0.01$ (t-test).

FIG. 7. Generation of TaMLO-A1 knockout mutants with the CRISPR-Cas9 system. (a) Schematic of the sgRNA target sites in exon 2 of TaMLO. The sgMLO-A1 target site is underlined. There are two SNPs are in red in the 20-nt sgRNA targeting site (C/G/G and A/C/A). (b) T7EI assay to detect sgMLO-A1-induced mutations in wheat protoplasts. Gene-specific primers (table 2) were used to detect mutations in TaMLO-A1, TaMLO-B1 and TaMLO-D1, respectively. Lanes marked with "1", sgRNA:Cas9-transformed protoplasts; Lanes marked with "2", wild-type controls. Arrowheads indicate the digested fragments by T7E1. The percentage below the gel indicates the indel mutation frequency measured from band intensities. Sequences of the mutations in TaMLO-A1 are shown to the right of the gel. (c) T7E1 assay and DNA sequencing to detect CRISPR-induced mutations in transgenic wheat plants. Arrowheads indicate the digested fragments by T7E1. The sequences of mutants in TaMLO-A1 are shown at the bottom of the gel. SEQ ID NOS: 172-188.

FIG. 8. DNA sequence of the GFP donor cassette. The cassette contains the GFP coding sequence (in bold) and the CaMV 35S terminator sequence (in italics), and is flanked by two T-MLO target sequences (underlined) at both ends. SEQ ID NO: 189

FIG. 9. Vector sequences. (a) The sequence of UBI-attr1-attr2-Nos in vector pYP010: 4047 bp. Underlined is the sequence of Ubi-1, the attr1 and attr2 are in italics. Nos is indicated in bold. (SEQ ID NO. 7) (b) The sequence of TAL-L in vector pZHY500: 2202 bp. The sequences of N terminal and C terminal are underlined. TAL-L is labelled in bold. (SEQ ID NO. 8) (c) The sequence of TAL-R in vector pZHY501: 2304 bp. The sequences of N terminal and C terminal are indicated. TAL-R is labelled in bold. (SEQ ID NO. 9) (d) The sequence of TALENs (TAL-L+TAL-R) in vector pZHY013. Sequences in italics are attr1 and attr2. The sequences of N terminal and C terminal parts are indicated underlined. TAL-L and TAL-R are in bold. The FokI sequences are in italics and underlined. T2A motif is underlined and in bold. (SEQ ID NO. 10).

DETAILED DESCRIPTION

Figure 2A:
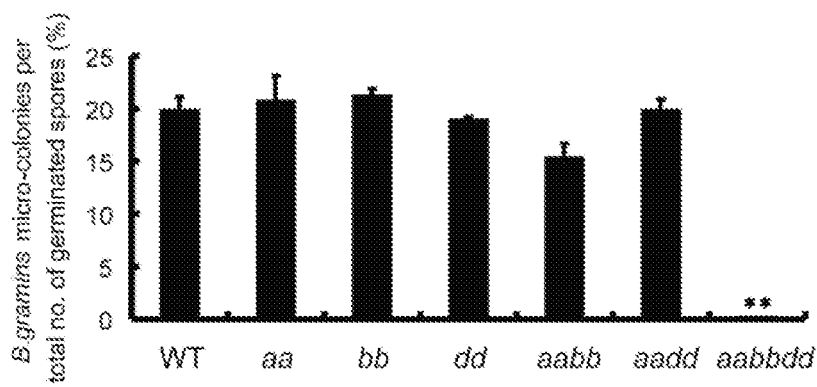
FIG. 2. Loss of TaMLO function confers resistance of bread wheat to powdery mildew disease. (a) Percentage of micro-colonies formed from the total number of germinated spores of *Blumeria graminis* f. sp. *tritici* (Bgt) inoculated on the leaves of wild-type (WT) and various tamlo mutants. At least 2,000 germinated spores per genotype per experiment were examined 72 hours after inoculation with virulent Bgt isolate E09. Values are the mean±s.d. of four independent experiments. **$P<0.01$ (t-test). (b) Micrographs of micro-colony formation of Bgt on the surfaces of leaves of the indicated genotypes 3 days post inoculation. Powdery mildew spores and colonies were stained with Coomassie blue. Bar=200 µm. (c) Macroscopic infection phenotypes of representative leaves of WT and the indicated mlo mutants 7 days after inoculation of detached leaves with Bgt. Bar=1 cm. (d) Disease symptoms of wild-type (WT) and tamlo-aabbdd mutant plants. The photograph was taken 7 days after inoculation in planta. Bar=2 cm.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene", "allele" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences. Thus, according to the various aspects of the invention, genomic DNA, cDNA or coding DNA may be used. In one embodiment, the nucleic acid is cDNA or coding DNA.

The terms "peptide", "polypeptide" and "protein" are used interchangeably herein and refer to amino acids in a polymeric form of any length, linked together by peptide bonds.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods.

For the purposes of the invention, a "mutant" plant is a plant that has been altered compared to the naturally occurring wild type (WT) plant. Specifically, the endogenous nucleic acid sequences of each of the MLO homologs in wheat (wild type nucleic acid sequences TaMLO-A1, TaMLO-B1 and TaMLO-D1) have been altered compared to wild type sequences using mutagenesis methods as described herein. This causes inactivation of the endogenous Mlo genes and thus disables Mb function. Such plants have an altered phenotype and show resistance or increased resistance to Pm compared to wild type plants. Therefore, the resistance is conferred by the presence of mutated endogenous TaMLO-A1, TaMLO-B1 and TaMLO-D1 genes in the wheat plant genome which has been specifically targeted using targeted genome modification and is not conferred by the presence of transgenes expressed in wheat As used herein, wild type nucleic acid sequences are designated using capital letters, that is TaMLO-A1, TaMLO-B1 and TaMLO-D1. Mutant mlo nucleic acid sequences use non-capitalisation, that is taml-a1, tamlo-b1, tamlo-d1. Mutant wheat plants of the invention comprise and express mutant mlo alleles.

mlo mutations that down-regulate or disrupt functional expression of the wild-type Mlo sequence are recessive, such that they are complemented by expression of a wild-type sequence. Thus "Mlo function" can be determined by assessing the level of constitutive defence response and/or susceptibility of the plant to a pathogen such as, for example, powdery mildew. Thus, according to the invention, a putative nucleotide sequence with Mlo function can be tested upon complementation of a suitable mlo mutant. The term "mlo function" is used to refer to sequences which confer a mlo mutant phenotype on a plant. The capitalisation of "Mlo" and non-capitalisation of "mlo" is thus used to differentiate between "wild-type and mutant" function.

A mlo mutant phenotype according to the invention is characterised by the exhibition of an increased resistance against Pm. In other words, a triple mlo mutant confers resistance to the pathogen causing Pm.

The aspects of the invention involve targeted mutagenesis methods, specifically genome editing, and in a preferred embodiment exclude embodiments that are solely based on generating plants by traditional breeding methods.

In a first aspect, the invention relates to a mutant wheat plant comprising a loss of function mutation in a TaMLO-A1, TaMLO-B1, and/or a TaMLO-D1 nucleic acid sequence. Thus, the mutant wheat plant according to the first aspect of the invention comprises taml-a1, tamlo-b1 and/or tamlo-d1 mutant nucleic acid sequences.

In one embodiment, the invention relates to a mutant wheat plant comprising a loss of function mutation in a TaMLO-A1, TaMLO-B1, and a TaMLO-D1 nucleic acid sequence wherein said mutation confers resistance to powdery mildew. Thus, the mutant wheat plant comprises a loss of function mutation in each of the endogenous MLO genes, that is in each of TaMLO-A1, TaMLO-B1 and TaMLO-D1. Thus, the mutant wheat plant according to the first aspect of the invention comprises taml-a1, tamlo-b1 and tamlo-d1 mutant nucleic acid sequences. The presence of these mutant mlo alleles confers Pm resistance.

The Pm resistance shown by such mutant plants is caused by the inactivation (loss of function) of the MLO wild type alleles due to the loss of function mutation, resulting in a recessive resistance phenotype.

In a preferred embodiment, the mutation is introduced into the wild type TaMLO-A1, TaMLO-B1, and/or TaMLO-D1, preferably each of TaMLO-A1, TaMLO-B1 and TaMLO-D1 nucleic acid sequences in a wheat plant using targeted genome modification.

In one embodiment, said targeted genome modification comprises the use of SSNs. These may be selected from ZFNs, TALENs, or CRISPR/Cas9. In one embodiment, the SSN is selected from a TALEN. In another embodiment, the SSN is selected from CRISPR/Cas9. This is described in more detail below.

The loss of function mutation in one, two or in each of TaMLO-A1, TaMLO-B1 and TaMLO-D1 may be a deletion or insertion with reference the wild type TaMLO-A1, TaMLO-B1 and TaMLO-D1 sequence.

The plant of the invention includes plants wherein said plant is heterozygous for the each of the mutations. In a preferred embodiment however, said plant is homozygous for the mutation in each of TaMLO-A1, TaMLO-B1, and TaMLO-D1. Such plants can be designed as having the genotype tamlo-aabbdd. Progeny that is also homozyous can easily be generated from these plants.

According to the various aspects of the invention, the wild type TaMLO-A1 comprises or consists of SEQ ID NO. 1, a fragment or a functional variant thereof. The corresponding amino acid sequence is SEQ ID NO. 4. According to the various aspects of the invention, the wild type TaMLO-B1 comprises or consists of SEQ ID NO. 2, a fragment or a functional variant thereof. The corresponding amino acid sequence is SEQ ID NO. 5. According to the various aspects of the invention, the wild type TaMLO-D1 comprises or consists of SEQ ID NO. 3, a fragment or a functional variant thereof. The corresponding amino acid sequence is SEQ ID NO. 6.

Thus, the invention relates to a mutant wheat plant comprising a loss of function mutation in each of TaMLO-A1, TaMLO-B1, and TaMLO-D1 wherein said mutation confers resistance to powdery mildew wherein the wild type sequence of TaMLO-A1 comprises or consists of SEQ ID NO. 1 or cDNA thereof, the wild type sequence of TaMLO-B1 comprises or consists of SEQ ID NO. 2 or cDNA thereof and the wild type sequence of TaMLO-AD1 comprises or consists of SEQ ID NO. 3 or cDNA thereof.

The term "functional variant of a nucleic acid or protein sequence" as used herein, for example with reference to SEQ ID NOs: 1, 2 or 3 refers to a variant gene sequence or part of the gene sequence which retains the biological function of the full non-variant TaMLO sequence and hence act to modulate responses to Pm. A functional variant also comprises a variant of the gene of interest encoding a polypeptide which has sequence alterations that do not affect function of the resulting protein, for example in non-conserved residues. Also encompassed is a variant that is substantially identical, i.e. has only some sequence variations, for example in non-conserved residues, to the wild type sequences as shown herein and is biologically active.

Generally, variants of a particular TaMLO nucleotide or amino acid sequence according to the various aspects of the invention will have at least about 80%-99%, for example 85%, 86%, 87%, 88%, 89%, 90%, 92%, 94%, 95%, 96%, 97%, 98% or 99% or more sequence identity to that particular non-variant TaMLO nucleotide sequence as determined by sequence alignment programs known in the art.

Also, the various aspects of the invention the aspects of the invention, including the methods and uses, encompass not only a TaMLO nucleic acid sequence, but also a fragment thereof. By "fragment" is intended a portion of the nucleotide sequence or a portion of the amino acid sequence and hence of the protein encoded thereby. Fragments of a nucleotide sequence may encode protein fragments that retain the biological activity of the native protein and hence act to modulate responses to Pm.

In one embodiment, the plant comprises the mutations in TaMLO-A1, TaMLO-B1 and/or TaMLO-D1 as shown in FIG. 5 or combinations thereof. In one embodiment, the mutations are as shown for tamlo-aabbdd. In other words, in said wheat plant, the endogenous TaMLO-A1 is a mutant TaMLO-A1 and comprises SEQ ID NO. 39, the endogenous TaMLO-B1 is a mutant TaMLO-B1 and comprises SEQ ID NO. 40, and the endogenous TaMLO-D1 is a mutant TaMLO-D1 and comprises SEQ ID NO. 41.

In one aspect, the mutant plant is TALEN free (see examples).

The wheat plant is selected from the list that includes, but is not limited to, *Triticum aestivum, T. aethiopicum, T. araraticum, T. boeoticum, T. carthlicum, T. compactum, T.*

*dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii* and *T. zhukovskyi*.

According to another embodiment the various aspects of the invention described herein, the plant is of the species *Triticum aestivum* or *Triticum turgidum*. According to another preferred embodiment, the plant belongs to the cultivar Bobwhite or the cultivar Don Pedro. More preferably, the cultivars BW208 and BW2003 (Bobwhite), which belong to the wheat species *Triticum aestivum* L. ssp *aestivum*, and the variety Don Pedro, which belongs to the wheat species *Triticum turgidum* L. ssp *durum*, are selected.

Bobwhite is the name of the cultivar obtained from the International Maize and Wheat Improvement Center (CIMMYT). BW208 and BW2003 are different Bobwhite lines. Don Pedro is a hard wheat variety, also from CIMMYT.

In particular, the invention relates to a triple mutant wheat genotype (*Triticum aestivum*), designated Accession Number CGMCC 9322 deposited under the Budapest Treaty at the China General Microbiological Culture Collection Center, Institute of Microbiology, Chinese Academy of Sciences, No. 1 Beichen West Road, Chaoyang District, Beijing 100101 on 18 Jun. 2014 by Caixia Gao, The Institute of Genetics and Developmental Biology Chinese Academy of Sciences, No. 1 Beichen West Road, Chaoyang District, Beijing 100101. The depositor's reference is Tamlo. The invention thus relates to any plants, parts thereof, including seeds, having this genotype. This mutant is described herein as Tamlo-aabbdd (FIG. 5).

A triple mutant wheat plant according to the invention shows resistance or increased resistance to Pm compared to a control plant, preferably a wild type plant, because the mutations in TaMLO-A1, TaMLO-B1, and TaMLO-D1 are knock out (loss of function) mutations that down-regulate or disrupt functional expression of the wild-type Mlo. Also, the wheat plant according to the invention shows increased yield compared to a control plant under biotic stress conditions wherein said stress is Pm.

Resistance can for example be assessed by assessing survival, growth, yield or size of pathogen colonies.

The terms "increase", "improve" or "enhance" are interchangeable. Yield for example is increased by at least a 3%, 4%, 5%, 6%, 7%, 8%, 9% or 10%, preferably at least 15% or 20%, more preferably 25%, 30%, 35%, 40% or 50% or more in comparison to a control plant. The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant. Thus, according to the invention, yield comprises one or more of and can be measured by assessing one or more of: increased seed yield per plant, increased seed filling rate, increased number of filled seeds, increased harvest index, increased number of seed capsules and/or pods, increased seed size, increased growth or increased branching, for example inflorescences with more branches. Preferably, yield comprises an increased number of seed capsules/pods and/or increased branching. Yield is increased relative to control plants.

A control plant as used herein is a plant, which has not been modified according to the methods of the invention. Accordingly, the control plant does not have a mutant tamlo nucleic acid sequence as described herein. In one embodiment, the control plant is a wild type wheat plant. In another embodiment, the control plant is a plant that does not have a mutant tamlo nucleic acid sequence as described here, but is otherwise modified. The control plant is typically of the same plant species, preferably the same ecotype or the same or similar genetic background as the plant to be assessed.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid of interest. The term "plant" also encompasses plant cells, suspension cultures, protoplasts, callus tissue, embryos, meristematic regions, gametophytes, sporophytes, pollen and microspores, again wherein each of the aforementioned comprises the gene/nucleic acid of interest.

The invention also extends to harvestable parts of a mutant plant of the invention as described above such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, flour, starch or proteins. The invention also relates to food products and food supplements comprising the plant of the invention or parts thereof.

In one aspect, the invention relates to a seed of a mutant wheat plant of the invention. Seeds harvested from a mutant plant that is homozygous for the mlo mutation in each of TaMLO-A1, TaMLO-B1 and TaMLO-D1 are preferred.

In another embodiment, the present invention provides a regenerable mutant plant as described herein cells for use in tissue culture. The tissue culture will preferably be capable of regenerating plants having essentially all of the physiological and morphological characteristics of the foregoing mutant wheat plant, and of regenerating plants having substantially the same genotype. Preferably, the regenerable cells in such tissue cultures will be callus, protoplasts, meristematic cells, cotyledons, hypocotyl, leaves, pollen, embryos, roots, root tips, anthers, pistils, shoots, stems, petiole, flowers, and seeds. Still further, the present invention provides wheat plants regenerated from the tissue cultures of the invention.

In another aspect, the invention relates to an isolated nucleic acid comprising SEQ ID NO. 39 (mutant tamlo-a1) or corresponding cDNA. In another aspect, the invention relates to an isolated nucleic acid comprising SEQ ID NO. 40 (mutant tamlo-b1) or corresponding cDNA. In another aspect, the invention relates to an isolated nucleic acid comprising SEQ ID NO. 41 (mutant tamlo-d1) or corresponding cDNA.

Method for Producing Mutant Plants

In another aspect, the invention relates to a method for producing a mutant wheat plant resistant to Pm comprising introducing a loss of function mutation into a TaMLO-A1, TaMLO-B1, and/or a TaMLO-D1 nucleic acid sequence in a wheat plant using targeted genome modification.

Plants that have a loss of function mutation in one or two MLO genes can be crossed to obtain a loss of function triple mutant. For example, a plant obtained by a method above that has a loss of function mutation in TaMLO-A1 nucleic acid, can be crossed with a plant obtained by a method above that has a loss of function mutation in TaMLO-B1 and/or TaMLO-D1. The resulting double mutant can be crossed with another plant obtained by a method above that has a loss of function mutation in TaMLO-B1 and/or TaMLO-D1 as required to obtain the triple mutant. In another example, a plant obtained by a method above that has a loss of function mutation in TaMLO-A1 and TaMLO-B1 can be crossed with another plant obtained by a method above that has a loss of function mutation in TaMLO-D1. Other combinations are apparent to the skilled person. The double or single mutant can be as show in FIG. 5.

In one embodiment of the methods described herein, a loss of function mutation is introduced into in each of the three endogenous TaMLO genes simultaneously using targeted genome modification. Thus, the resulting mutant wheat plant comprises a loss of function mutation in each of the endogenous MLO genes, that is TaMLO-A1, TaMLO-B1, and TaMLO-D1. The mutant plant thus comprises mutant tamlo-a1, tamlo-b1 and tamlo-d1 nucleic acid sequences. Preferably, the resulting mutant wheat plant is homozygous for these mutations.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customizable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate its nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440, 432and 8,450,471. Reference 30 describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and a large monomeric DNA nuclease guided to a DNA target sequence adjacent to the PAM (protospacer adjacent motif) sequence motif by a complex of two non-coding RNAs: CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3.

Cas9 expression plasmids for use in the methods of the invention can be constructed as described in the art. One example is provided as described in the example section herein.

The method for producing a mutant wheat plant according to the invention resistant to Pm using genome editing comprises the use of a SSN. This may be selected from a meganuclease, ZFN, TALEN, or CRISPR/Cas9. In one embodiment, the SSNs is a TALEN.

Thus, in one embodiment, the method comprises the use of TALEN. In this embodiment, the method comprises introducing an expression vector comprising a TALEN into a wheat plant and screening for TALEN-induced targeted mutations in TaMLO-A1, TaMLO-B1 and/or TaMLO-D1 genes. The method may also comprise the further step of regenerating a plant and selecting or choosing a plant resistant to Pm.

In one embodiment, said vector comprises a pair of TALENs (T-MLO) targeting a conserved region in exon 2 (FIG. 1a, 9 and table 1). The vector construct encodes a pair of TALENs that targets sequences conserved between all three homoeologues MLO genes of wheat.

Thus, in one embodiment, the target sequence site in TaMLO is TCGCTGCTGCTCGCCGTgacgcaggacccatctc-CGGGATATGCATCTCCGA (SEQ ID NO. 13, Table 1).

Specifically, the binding site sequences of the second exon conserved region TaMLO-A, TaMLO-B and TaMLO-D to which these TALENs bind see also are FIG. 1):

```
MLO-A:
                                     (SEQ ID NO. 14)
TCGCTGCTGCTCGCCGTcacgcaggacccaatctcCGGGATATGCATC

TCCCA

MLO-B:
                                     (SEQ ID NO. 15)
TCGCTGCTGCTCGCCGTgacgcaggacccatctcCGGGATATGCATC

TCCGA

MLO-D:
                                     (SEQ ID NO. 16)
TCGCTGCTGCTCGCCGTgacgcaggacccaatctcCGGGATATGCATC

TCCGA
```

The three SNPs are in bold and underlined. The AvaII restriction site is shown in small letters and underlined.

A TALEN pair has for example the nucleic acid sequence SEQ ID NO. 11. The corresponding amino acid sequence is SEQ ID NO. 12.

In this embodiment, the TALEN pair recognizes 16 bp and 17 bp, respectively, of contiguous DNA separated by an 18 bp spacer DNA containing an AvaII restriction site as shown above, (FIG. 5a. 10 and Table 1). The TALEN recognition sequences are strictly conserved in TaMLO-B1 and TaMLO-D1, but have one nucleotide mismatch with the cognate TaMLO-A1 target site (FIG. 1a). In addition, the conserved spacer region in FIG. 1a contains two single nucleotide polymorphisms (SNPs) among the three MLO homoeo-alleles.

As shown in the examples, in order to detect the mutation at the site targeted by the genetic editing technique, an Ava II enzyme digestion locus was selected from the targeted sites; if mutation occurred, then the Ava II enzyme digestion locus was damaged and cannot be digested. However, non-mutated PCR products are susceptible to digestion.

In one embodiment, the TALENs are assembled by the Golden Gate cloning method and built into a single plasmid as described in the examples.

In one embodiment, screening for TALEN-induced targeted mutations in TaMLO-A1, TaMLO-B1 and TaMLO-D1 genes comprises obtaining a DNA sample from a transformed plant and carrying out DNA amplification and optionally restriction enzyme digestion to detect a mutation in TaMLO-A1, TaMLO-B1 and/or TaMLO-D1. When the target site is as shown above, the restriction enzyme is AvaII.

PCR fragments amplified from the transformed plants are then assessed using a gel electrophoresis based assay. In a further step, the presence of the mutation may be confirmed by sequencing the TaMLO-A1, TaMLO-B1 and/or TaMLO-D1 genes.

In another embodiment, the method comprises the use of CRISPR/Cas9. In this embodiment, the method therefore comprises introducing and co-expressing in a wheat plant Cas9 and sgRNA targeted to TaMLO-A1, TaMLO-B1 and/or TaMLO-D1 and screening for induced targeted mutations in TaMLO-A1, TaMLO-B1 and TaMLO-D1 genes. The method may also comprise the further step of regenerating a plant and selecting or choosing a plant resistant to Pm.

Cas9 and sgRNA may be comprises in a single or two expression vectors.

The target sequence in TaMLO-A1 may be CCGT-CACGCAGGACCCAATCTCC (SEQ ID NO. 17, see table 1).

In one embodiment, screening for CRISPR-induced targeted mutations in TaMLO-A1, TaMLO-B1 and TaMLO-D1 genes comprises obtaining a DNA sample from a transformed plant and carrying out DNA amplification and optionally restriction enzyme digestion to detect a mutation in TaMLO-A1, TaMLO-B1 and/or TaMLO-D1.

In one embodiment, the restriction enzyme is mismatch-sensitive T7 endonuclease. T7E1 enzyme that is specific to heteroduplex DNA caused by genome editing.

PCR fragments amplified from the transformed plants are then assessed using a gel electrophoresis assay based assay. In a further step, the presence of the mutation may be confirmed by sequencing the TaMLO-A1, TaMLO-B1 and/or TaMLO-D1 genes.

As shown in the examples, genomic DNA (i.e. wt and mutant) can be prepared from each sample, and DNA fragments encompassing each target site are amplified by PCR (see Table). The PCR products are digested by restriction enzymes as the target locus includes a restriction enzyme site. The restriction enzyme site is destroyed by CRISPR- or TALEN-induced mutations by NHEJ or HR, thus the mutant amplicons are resistant to restriction enzyme digestion, and result in uncleaved bands. Alternatively, the PCR products are digested by T7E1 (cleaved DNA produced by T7E1 enzyme that is specific to heteroduplex DNA caused by genome editing) and visualized by agarose gel electrophoresis. In a further step, they are sequenced.

In another aspect, the invention relates to a method for conferring resistance to Pm to a wheat plant or increasing resistance of a wheat plant to Pm comprising introducing a loss of function mutation into a TaMLO-A1, TaMLO-B1, and a TaMLO-D1 nucleic acid sequence using targeted genome modification.

Thus, the resulting mutant wheat plant comprising a loss of function mutation in each of the endogenous MLO genes in wheat, that is TaMLO-A1, TaMLO-B1 and TaMLO-D1. Thus, the resulting mutant wheat plant comprises mutant genes tamlo-a1, tamlo-b1 and tamlo-d1.

In one embodiment, ZFN, TALEN, or CRISPR/Cas9 is used. In one embodiment, the method comprises producing a mutant plant as described above.

In the methods above, amplification is preferably carried out using PCR and primers that specifically amplify TaMLO-A1, TaMLO-B1 and TaMLO-D1 (table 2) and as shown below:

The following primer pair amplifies the TaMLO-A1 target site:

```
MLO-A1-F
                                    (SEQ ID NO. 18)
TGGCGCTGGTCTTCGCCGTCATGATCATCGTC

MLO-A1-R
                                    (SEQ ID NO. 19)
TACGATGAGCGCCACCTTGCCCGGGAA
```

The following primer pair amplifies the TaMLO-B1 target site:

```
MLO-B1-F
                                    (SEQ ID NO. 20)
ATAAGCTCGGCCATGTAAGTTCCTTCCCGG

MLO-B1-R
                                    (SEQ ID NO. 21)
CCGGCCGGAATTTGTTTGTGTTTTTGTT
```

The following primer pair amplifies the TaMLO-D1 target site:

```
MLO-D1-F
                                    (SEQ ID NO. 22)
TGGCTTCCTCTGCTCCCTTGGTGCACCT

MLO-D1-R
                                    (SEQ ID NO. 23)
TGGAGCTGGTGCAAGCTGCCCGTGGACATT
```

The following primer pair amplifies all three alleles

```
MLO-F
                                    (SEQ ID NO. 24)
GTCTTCGCCGTCATGATCATCGTCTCC

MLO-R
                                    (SEQ ID NO. 25)
TGGTATTCCAAGGAGGCGGTCTCTGTCT
```

In a preferred embodiment, the methods above are carried out by transforming wheat embryos. In a further preferred embodiment, the methods comprise generating stable T2 plants preferably homozygous for the mutation.

In one embodiment, the methods do not comprise transforming wheat protoplasts.

The methods above use plant transformation to introduce an expression vector comprise a SSN into a plant. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle bombardment as described in the examples, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The SSN is preferably introduced into a plant as part of an expression vector. The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence. The vector desirably also has unique restriction sites for the insertion of DNA sequences. If a vector does not have unique restriction sites it may be modified to introduce or eliminate restriction sites to make it more suitable for further manipulation. Vectors suitable for use in expressing the nucleic acids, are known to the skilled person and a non-limiting example is pYP010.

The nucleic acid is inserted into the vector such that it is operably linked to a suitable plant active promoter. Suitable plant active promoters for use with the nucleic acids include, but are not limited to CaMV35S wheat U6, or maize ubiquitin promoters.

The vector may also comprise a GFP sequence or other marker as explained in the examples and in the figures.

A plant obtained or obtainable by the methods described above is also within the scope of the invention.

In one aspect, the mutant is TALEN free. Thus, according to the method above, the presence of a TALEN can be assessed as described in the examples.

In another aspect, the invention relates to an isolated nucleic acid selected from SED ID NOs. 18 to 25 or 42 to 47 or a sequence with at least 90%, 91%, 92%, 93%, 94%, 95%, 96%, 97%, 98% or 99% homology thereto. These sequences are primers which allow the amplification of the TaMLO-A1, TaMLO-B1 and TaMLO-D1 target sites respectively or primers that are allele specific as explained herein.

The invention also relates to an expression vector comprising a TALEN which targets SEQ ID NO. 13. The invention also relates to a host cell transformed with said vector. In one embodiment, the vector is as shown in FIG. 9 (SEQ ID NOs. 7-10).

Detection Methods

The invention also relates to diagnostic tests, methods and assays for determining the presence of one of more mutant tamlo-a1, tamlo-b1 and/or tamlo-d1 nucleic acid or polypeptide, preferably all of the mutant tamlo-a1, tamlo-b1 and/tamlo-d1 nucleic acids or polypeptides, in a wheat plant or part thereof which together confer resistance to Pm.

Broadly, the methods divide into those screening for the presence of one or more mutant nucleic acid sequences and those that rely on detecting the presence or absence of a polypeptide. The methods may make use of biological samples from one or more plants or cells modified according to the invention that are suspected to contain the nucleic acid sequences or polypeptide.

The use of diagnostic tests for mutant tamlo-a1, tamlo-b1 and/or tamlo-d1 nucleic acid which together confer resistance to Pm allows the researcher or plant breeder to establish, with full confidence and independent from time consuming resistance tests, whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants. The mlo mutant nucleic acids conferring the desirable disease resistance phenotype are recessive, and are not therefore detectable at the whole plant phenotype level when in a heterozygous condition in the presence of a wild-type Mlo allele.

Phenotypic screening for the presence of such recessive alleles is therefore only possible on material homozygous for the mlo locus and so delays substantially the generation in a plant breeding programme at which selection can be reliably and cost effectively applied. In a backcross breeding programme where, for example, a breeder is aiming to introgress a desirable mlo allele into an elite adapted high performing target genotype, the mlo locus will be permanently in the heterozygous condition until selfing is carried out. Nucleic acid or polypeptide testing for the presence of the recessive allele avoids the need to test selfed progeny of backcross generation individuals, thus saving considerable time and money. In other types of breeding scheme based on selection and selfing of desirable individuals, nucleic acid or polypeptide diagnostics for the desirable mlo alles in high throughput, low cost assays as provided by this invention, reliable selection for the desirable mlo alleles can be made at early generations and on more material than would otherwise be possible. This gain in reliability of selection plus the time saving by being able to test material earlier and without costly resistance phenotype screening is of considerable value in plant breeding.

There are various methods for determining the presence or absence in a test sample of a particular nucleic acid or polypeptide encoded by such nucleic acid, such as mutant tamlo-a1, tamlo-b1 and/or tamlo-d1 polypeptides which together confer resistance to Pm in a triple mutant.

For example, the sequence information provided herein also allows the design of diagnostic tests for determination of the presence of a specific mutant tamlo-a1, tamlo-b1 and/or tamlo-d1 nucleic acid sequence which confers Pm resistance, preferably determination of the presence of a specific tamlo-a1, tamlo-b1 and/or tamlo-d1 mutant nucleic acid or a susceptibility allele (e.g. wild-type), in any given wheat plant, cultivar, variety, population, landrace, part of a family or other selection in a breeding programme or other such genotype. A diagnostic test or detection method according to the invention may be based on determination of the presence or absence of a particular mutant tamlo-a1, tamlo-b1 and/or tamlo-d1 nucleic acid sequence which confers Pm resistance by means of nucleic acid or polypeptide determination.

At the nucleic acid level, a diagnostic test may involve hybridisation of a suitable oligo- or poly-nucleotide, such as a fragment of the Mlo gene. The hybridisation may involve PCR designed to amplify a product from a given allelic version of mlo, with subsequent detection of an amplified product by any of a number of possible methods including but not limited to gel electrophoresis, capillary electrophoresis and direct hybridisation of nucleotide sequence probes. A diagnostic test may be based on PCR designed to amplify various mutant nucleic acids from the Mlo locus, with a test to distinguish the different possible mutant nucleic acids from the wild type by any of a number of possible methods, including DNA fragment size, restriction site variation (e.g. CAPS—cleaved amplified polymorphic sites) and so on. A diagnostic test may also be based on a great number of possible variants of nucleic acid analysis that will be apparent to those skilled in the art, such as use of a synthetic mlo-derived sequence as a hybridisation probe.

The diagnostic test identifies the plants' genotype. The genotype of a plant can be characterized through a genetic marker profile which can identify plants of the same variety, or a related variety, or be used to determine or validate a pedigree.

There are many laboratory-based techniques available for the analysis, comparison and characterization of a plant genotype to assess the presence of a mutant allele according to the invention. These include but are not limited to among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs).

In one embodiment, genotyping is based on SNPs. This can be based on fluorescent detection of SNP-specific hybridization probes on PCR products such as Taqman or Molecular Beacons. Other strategies such as Sequenom homogeneous Mass Extend (hME) and iPLEX genotyping systems involve MALDI-TOF mass spectrophotometry of SNP-specific PCR primer extension products. SNP in TaMLO genes as described herein can be used.

In one embodiment, Kompetitive Allele Specific PCR (KASP) genotyping is used. This requires the presence of 1) a purified DNA sample, 2) two allele-specific forward primers, and 3) a common reverse primer. KASP is a SNP genotyping system FRET (Fluorescent Resonance Energy Transfer). FRET allows for the detection of SNP's without the need for a separation step. Coupled with the power of competitive allele specific PCR, the KASP is a well described system for determination of SNP or insertion/deletion genotypes Particular markers used for these purposes are not limited to any particular set of markers, but are envisioned to include any type of marker and marker profile which provides a means of distinguishing varieties.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Other exemplary approaches for detecting nucleic acid or polypeptides according to the methods described herein include analysing a sample from the plant or plant cell by:
(a) comparing the sequence of a mutant nucleic tamlo-a1, tamlo-b1 and/or tamlo-d1 nucleic acid in the sample with all or part of the wild type nucleotide sequence to determine whether the sample from the plant contains a mutation;
(b) determining the presence in the sample of a polypeptide including the wild type amino acid sequence of TaMLO-A1, TaMLO-B1 and TaMLO-D1 or a fragment thereof and, if present, determining whether the polypeptide is full length, and/or is mutated, and/or is expressed at the normal level;
(c) performing DNA fingerprinting to compare the restriction pattern produced when a restriction enzyme cuts nucleic acid in the sample with the restriction pattern obtained from the wild type TaMLO-A1, TaMLO-B1 and TaMLO-D1 nucleotide sequence or from a known mutant, allele or variant thereof;
(d) contacting the sample with a specific binding member capable of binding to nucleic acid including the wild type nucleotide sequence of TaMLO-A1, TaMLO-B1 and TaMLO-D1 or a fragment thereof, or a mutant, allele or variant thereof, the specific binding member including nucleic acid hybridisable with the wild type nucleotide or a polypeptide including a binding domain with specificity for nucleic acid and determining binding of the specific binding member;
(e) performing PCR involving one or more primers based on the wild type nucleotide sequence of TaMLO-A1, TaMLO-B1 and TaMLO-D1 or a mutant nucleotide sequence of tamlo-a1, tamlo-b1 and/or tamlo-d1 to screen the sample for nucleic acid including the wild type nucleotide sequence or a mutant, allele or variant thereof.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN'ases.

In one aspect, the invention relates to a method for determining the presence of a mutant tamlo-a1, tamlo-b1 and/or tamlo-d1 nucleic acid in a wheat plant.

In one embodiment, genotyping is based on detecting SNPs or mutations.

The method may comprise the steps of
a) obtaining a nucleic acid sample from a wheat plant
b) carrying out nucleic acid amplification of one or more TaMLO gene using one or more primer pairs selected from SED ID No. 18 to 25 or SEQ ID NOs. 42-47.

Primer pairs are allele specific and can be used to detect the triple mutant tamloaabbdd as shown in FIG. 5.

The following mutant allele specific primer pair amplifies Tamloa in the triple mutant tamloaabbdd.

```
MLO-MU-A1-F:
                                    (SEQ ID NO. 42)
CTGATGCTGGTGGGATTCAATCTCCGG

MLO-MU-A1-R:
                                    (SEQ ID NO. 43)
TGGTATTCCAAGGAGGCGGTCTCTGTCT
```

The following mutant allele specific primer pair amplifies Tamlob in the triple mutant tamloaabbdd.

```
MLO-MU-B1-F:
                                    (SEQ ID NO. 44)
ACATCGTTGCGCTCAGCCAACACCCGGC

MLO-MU-B1-R:
                                    (SEQ ID NO. 45)
TGGTATTCCAAGGAGGCGGTCTCTGTCT
```

The following mutant allele specific primer pair amplifies Tamlod in the triple mutant tamloaabbdd.

```
MLO-MU-D1-F:
                                    (SEQ ID NO. 46)
CTAACTATGCGTGACGGCGAGCAGCAGGA

MLO-MU-D1-R:
                                    (SEQ ID NO. 47)
TGGTATTCCAAGGAGGCGGTCTCTGTCT
```

In another embodiment, KASP genotyping is used. The method may comprise the steps of
a) obtaining a nucleic acid sample from a wheat plant
b) carrying out amplification using two allele-specific forward primers, and a common reverse primer.

The allele-specific primer may be selected from SEQ ID NOs. 42-47 for the triple mutant described herein. Common primers that can be used are described herein. Alternatively, primers can be designed using proprietary Kraken™ software system.

The nucleic acid is preferably DNA. The method may also include digesting the sample with a restriction enzyme or T7E1 to detect he mutant allele.

As shown in the examples, genomic DNA (i.e. wt and mutant) can be prepared from each sample, and DNA fragments encompassing each target site are amplified by PCR (see Table). The PCR products are digested by restriction enzymes as the target locus includes a restriction enzyme site. The restriction enzyme site is destroyed by CRISPR- or TALEN-induced mutations by NHEJ or HR, thus the mutant amplicons are resistant to restriction enzyme digestion, and result in uncleaved bands. Alternatively, the PCR products are digested by T7E1 (cleaved DNA produced by T7E1 enzyme that is specific to heteroduplex DNA caused by genome editing) and visualized by agarose gel electrophoresis. In a further step, they are sequenced.

The amplification product is analysed using a gel electrophoresis assay. In one embodiment, the sequence of the TaMLO-A1, TaMLO-B1, and/or TaMLO-D1 nucleic acid sequence is determined using sequence analysis. The sequence is then compared with the wild type nucleic acid sequence to assess the presence of a mutation.

Nucleic acid may be screened using a variant- or allele specific probe. Such a probe corresponds in sequence to a region of the gene, or its complement, containing a sequence alteration known to be associated with disease resistance. Under suitably stringent conditions, specific hybridisation of such a probe to test nucleic acid is indicative of the presence of the sequence alteration in the test nucleic acid. For efficient screening purposes, more than one probe may be used on the same test sample. The probe may be labelled.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

Specific primers that detect Tamlo-aabbdd as shown in FIG. 5 can be designed by one skilled in the art by routine methods. In other words, specific probes/primers that are specific to each of the tamlo-aa, tamlo-bb and tamlo-dd mutations in the triple mutant described herein can be designed based on the mutation in the nucleic acid sequence.

An alternative or supplement to looking for the presence of variant sequences in a test sample is to look for the presence of the normal sequence, e.g. using a suitably specific oligonucleotide probe or primer.

In one embodiment, the method comprises obtaining a wheat protoplast and said sample is isolated from a protoplast.

There are also various methods for determining the presence or absence in a test sample of a particular polypeptide, such as a TaMLO-A1, TaMLO-B1, and TaMLO-D1 polypeptide.

In another diagnostic test according to the invention a sample of a wheat described herein plant may be tested for the presence or absence of a binding partner for a specific binding member such as an antibody (or mixture of antibodies), specific for one or more particular mutant TaMLO-A1, TaMLO-B1, and TaMLO-D1 polypeptide and/or wild type TaMLO-A1, TaMLO-B1, and TaMLO-D1 polypeptide.

In another embodiment, the invention relates to method for determining the presence or absence of a wild type TaMLO-A1, TaMLO-B1, and TaMLO-D1 polypeptide in a wheat plant said method using antibodies which specifically detect a wild type TaMLO-A1, TaMLO-B1, and TaMLO-D1 polypeptide. The wild TaMLO-A1, TaMLO-B1, and TaMLO-D1 polypeptide may comprise SEQ ID NOs: 4, 5 or 6 encoded by the SEQ ID NO. 1, 2 or 3.

This is particularly useful if the mutant does not yield a protein due to the mutation. This is the case for the triple mutant deposited as described herein.

In another embodiment of the, the invention relates to method for determining the presence of a mutant TaMLO-A1, TaMLO-B1, and TaMLO-D1 polypeptide in a wheat plant said method comprising assessing presence of a mutant TaMLO-A1, TaMLO-B1, and TaMLO-D1 polypeptide using antibodies which specifically detect a mutant TaMLO-A1, TaMLO-B1, and TaMLO-D1 polypeptide. The mutant TaMLO-A1, TaMLO-B1, and TaMLO-D1 polypeptide may be encoded by the mutant TaMLO-A1, TaMLO-B1, and TaMLO-D1 nucleic acids described herein, for example as shown in SEQ ID NOs. 39-41.

In another aspect, the invention relates to detection kit for determining the presence of a mutant TaMLO-A1, TaMLO-B1, and/or TaMLO-D1 nucleic acid sequence in a wheat plant comprising one or more primer selected from SED ID NOs. 18-25 or 42 to 47. In one embodiment, said kit comprises all primers of SED ID NOs. 18-25 or 42 to 47. In one embodiment, restriction enzyme digest may also be used.

The various aspects of the invention described herein clearly extend to any plant cell or any plant produced, obtained or obtainable by any of the methods described herein, and to all plant parts and propagules thereof unless otherwise specified. The present invention extends further to encompass the progeny of a mutant plant cell, tissue, organ or whole plant that has been produced by any of the aforementioned methods, the only requirement being that progeny exhibit the same genotypic and/or phenotypic characteristic(s) as those produced by the parent in the methods according to the invention.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification, including reference to sequence database identifiers, are incorporated herein by reference in their entirety. Unless otherwise specified, when reference to sequence database identifiers is made, the version number is 1.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

TALEN Design and Construction

TALEN target sites were designed using the TAL effector-Nucleotide Targeter 2.0 (TALE-NT) program (https://tale-nt.cac.cornell.edu/). All the target sites had a T at the −1 position, and the corresponding TAL effector arrays were constructed using the Golden Gate method as previously described[33]. Information on all the TAL effecter arrays and target sites is given in Table 1. TALENs were assembled in vectors with a truncated N152/C63 backbone architecture (pZHY500 and pZHY501). The Gateway-compatible entry plasmid, pZHY013, was used as the intermediate vector to create TALEN expression vectors[34]. This plasmid contains two heterodimeric FokI nuclease domains separated by a T2A translational skipping sequence. TAL arrays in the plasmids pZHY500 and pZHY501 were released by digestion with XbaI/BamHI and subcloned into pZHY013 one-by-one[34, 35]. One array (left array) was first cloned into pZHY013 as an XbaI/BamHI fragment; the other (right array) was then cloned into the NheI/BglII sites, which have ends compatible with XbaI and BamHI. A Gateway LR reaction was performed to clone the TALEN coding sequences into the destination vector, pYP010 (a derivative of pZHY05134 by replacing the 35S promoter with the maize ubiquitin promoter.

Construction of Cas9 and sgRNA Expression Vectors

The plasmid pJIT163 was used to construct the Cas9 expression plasmid. It was digested with KpnI and HindIII and fused with the maize ubiquitin 1 promoter (Ubi) to construct vector pJIT163-Ubi. Full-length Cas9 (plant codon-optimized) products were digested with BamHI and MfeI and inserted into plasmid pJIT163-Ubi between the BamHI and MfeI sites to yield the expression vector pJIT163-Ubi-Cas9. The wheat U6 promoters and wheat gRNA scaffolds were synthesized by GenScript and cloned into pEASY-blunt vector (TransGen Biotech). The sequences of Cas9 and the gRNAs are given in a previous publication[17]. Wheat genomic DNA region immediately precede a 5'-NGG PAM, such as 5'-G-N(20)-GG-3' or 5'-N(21)-GG-3' was selected as target.

The CRSIPR/Cas9 target site in TaMLO contains two single nucleotide polymorphisms (SNPs) among the three homoeoalleles. We designed an sgRNA (sgMLO-A1) to specifically target TaMLO-A1. Our results show that sgRNA-A1-induced mutations only occurred in TaMLO-A1, so confirming the specificity of the sgRNA for TaMLO-A1. Therefore, off-target cleavage did not occur in TaMLO-B1 and TaMLO-D1. The results show that CRISPR/Cas9 is active in wheat plants and that transgenic mutant lines can be generated. Other mutants, including a triple mutant AA, BB and DD can be obtained using Cas9/sgRNA by targeting a conserved target site.

Wheat Protoplast Transformation

Wheat protoplasts were isolated and transformed as previously described[3]. Average transformation efficiencies were 60-80%. Protoplast transformation was carried out with 20 μg of TALEN plasmid per transformation, or a mixture of 10 μg pJIT163-Ubi-Cas9 plasmid and 10 μg pU6-gRNA plasmid.

Biolistic Transformation of Wheat

Biolistic transformation was performed using a PDS1000/He particle bombardment system (Bio-Rad, Hercules, Calif.) with a target distance of 6.0 cm from the stopping plate at helium pressure 1100 psi. Plasmid DNAs (T-MLO and pAHC20) were mixed in a 1:1 (1:1:1 for Cas9, sgRNA and pAHC20) molar ratio prior to bombardment. After bombardment, embryos were transferred to callus induction medium. In the third or fourth week, all calli were transferred to selective regeneration medium containing 5 mg/l phosphinothricin (PPT). PPT was present in all subsequent tissue culture procedures including 2 rounds of regeneration (4 weeks) and 2 rounds of rooting (4 weeks). After 10-12 weeks, T0 transgenic plants were obtained, transferred into soil and grown in a management greenhouse[37].

Screening of SSN-induced Mutations

Genomic DNA from individual wheat plants was extracted using the high-throughput Automation Workstation Biomek® FX (Beckmen) with the magnetic bead-based DNA extraction kit (GeneOn Biotech). The PCR/RE digestion screen assay and T7E1 assay were used to identify the mutations as previously described[36,36, 37]. The PCR products amplified with TaMLO-specific primers (Table 3) from individual mutant plants were cloned into pUC-T vector (CWBIO) for sequencing. Mutation frequencies (indels (%)) in protoplasts were calculated by measuring band intensities with UVP VisionWorks LS Image Acquisition Analysis Software 7.0[36].

Powdery Mildew Infection and Microscopic Analyses

Wheat plants were grown on soil in controlled environment chambers at 22° C. and 16-h photoperiod with light intensity ranging from 400-1,000 μmol $m^{-2}$ $s^{-1}$. Powdery mildew infection and microscopic analyses were performed as previously reported[39] with some modifications. Leaves originating from the main stem (leaves 2, 3, and 4) were cut into 5 cm segments and immediately placed in Petri dishes containing 1% (w/v) distilled water agar and 8.5 mM benzimidazole. The leaf segments were incubated at 22° C. in continuous light (100 μmol $m^{-2}$ $s^{-1}$) for four hour, then inoculated with virulent strains of *Blumeria graminis* f. sp. *tritici* (Bgt) E09, E22 and B13 to give approximately 15 to 20 sporulating colonies per $cm^2$ and incubated at 22° C. in continuous light (100 umol $m^{-2}$ $s^{-1}$). Seventy-two hours after inoculation, the leaf segments were fixed with 1:1 (v/v) ethanol:acetic acid for 24 h, cleared with lactoglycerol (1:1:1 [v/v] lactic acid:glycerol:$H_2O$) for 48 h, and stained for 7 sec with Coomassie blue (0.6% [w/v] Coomassie Brilliant Blue R 250 [Sigma] in methanol) to visualize the fungal structure, finally rinsed in distilled water and mounted in 50% (v/v) glycerol prior to microscopy. Samples were observed and analyzed under an Olympus BX51 light microscope, and photographs were taken using software Cellsens Entry 1.21.

Results and Discussion

To modify all three TaMLO copies, we deployed a pair of TALENs (T-MLO) targeting a conserved region in exon 2 (FIG. 1a). The TALEN pair recognizes 16 bp and 17 bp, respectively, of contiguous DNA separated by an 18 bp spacer DNA containing an AvaII restriction site (FIG. 1a and Table 1). The TALEN recognition sequences are strictly conserved in TaMLO-B1 and TaMLO-D1, but have one nucleotide mismatch with the cognate TaMLO-A1 target site (FIG. 1a). In addition, the conserved spacer region in FIG. 1a contains two single nucleotide polymorphisms (SNPs) among the three MLO homoeo-alleles. The TALENs were assembled by the Golden Gate cloning method[30], and built into a single plasmid by a T2A translational skipping sequence driven by the maize ubiquitin promoter (FIG. 4a). The activity of the resulting T-MLO was first evaluated by transforming the TALEN-carrying plasmid into wheat protoplasts. Analysis of genomic DNA from the transformed protoplasts using a previously developed PCR restriction enzyme digestion assay (PCR/RE)[16] demonstrated the occurrence of insertion/deletion (indel) mutations at the target site with efficiencies ranging from 23% to 38% in genomes A, B and D (FIGS. 4b and 4c); the one nucleotide difference did not affect T-MLO cleavage at the TaMLO-A1 site.

Next we co-transformed the T-MLO plasmid and pAHC20[31], a plasmid harboring the selectable bar gene, into immature wheat embryos by the particle bombardment method. Wheat seedlings were regenerated from herbicide-resistant calli after 6-8 weeks of selection on 5 µg/ml phosphinothricin (PPT). The MLO target sites (in TaMLO-A1, TaMLO-B1 and TaMLO-D1) were first amplified from the genomic DNA of these transgenic seedlings (T0 plants) using a conserved primer set (Table 2), and analyzed by the PCR/RE assay to detect potential mutations. We identified 27 mutations in 450 independent T0 transgenic lines (6.0%) from five independent transformation experiments in winter wheat variety Kenong199, and 8 mutations out of 237 T0 lines (3.4%) in spring wheat variety Bobwhite from one transformation experiment (Table 3). In order to identify in which of the TaMLO genes the mutations occurred, we designed primers to specifically amplify TaMLO-A1, TaMLO-B1 and TaMLO-D1. PCR/RE assays of the PCR amplicons with the specific primers (Table 2) revealed that T-MLO-induced mutations occurred in all three diploid genomes (FIG. 1b). The mutations were confirmed by sequencing, which showed that most of the mutations within the TALEN target region were small deletions of 1 to 10 bp (FIG. 1c). Among 27 T0 plants, we identified 12 mutants heterozygous for TaMLO-A1, 8 mutants heterozygous for TaMLO-D1, 1 mutant heterozygous for TaMLO-B1 but homozygous for TaMLO-A1, 3 mutants heterozygous for both TaMLO-A1 and TaMLO-D1, and 1 mutant heterozygous for all three homoeo-alleles (FIG. 1b and Table 6). In addition, we found two T0 plants (T0-6 and T0-9) in which multiple types of deletions occurred at a single target site, i.e., four mutation patterns were found in plant T0-6 in TaMLO-A1 and three in T0-9 in TaMLO-D1 (FIG. 1c and Table 6). This phenomenon has also been reported in barley[13], maize[23], rice[19] and Arabidopsis[11,24]. The above results support the view that TALENs can efficiently create targeted mutations in the bread wheat genome.

To investigate whether the mutations could be transmitted to the next generation, nine of the T0 plants, which carried mutations in the different diploid genomes, were self-pollinated, and individual T1 progeny were genotyped using MLO allele-specific primers. The segregation data indicated that the TALEN-generated mutations were passed to the next generation. In general, for mutations that were homozygous in T0, transmission rates were 100%, and most of the mutations that were heterozygous in T0 segregated in Mendelian fashion (1:2:1) in the T1 (Table 6). For example, in plant T0-8, a mutation in TaMLO-A1 that was homozygous in T0 was present in all 58 T1 progeny, while a mutation in TaMLO-B1 that was heterozygous in T0 segregated in a 1:2:1 ratio in 58 T1 progeny (Table 6). However, the segregation patterns of the complex mutations found in plants T0-6 and T0-9 did not fit a Mendelian ratio, probably because these mutations took place in somatic cells that did not participate in the production of gametes. Interestingly, some new mutations were detected in the T1 plants, e.g., the mutation that arose in plant T0-4 was only detected in TaMLO-D1, but in its T1 progeny we found additional mutations in TaMLO-A1 and TaMLO-B1 (Table 6), suggesting that the TALENs remained active in the T0 and/or T1 plants. Similar results have been reported in Arabidopsis plants treated with the CRISPR/Cas9 system[11]. We analyzed further the transmission of homozygous and heterozygous mutations from six T1 plants to their T2 offspring. Again, the homozygous mutations were 100% transmitted whereas the heterozygous mutations segregated in a Mendelian fashion (Table 4). These results demonstrate that TALEN-mediated gene modifications observed in primary transformed bread wheat plants (T0) can be stably transmitted to subsequent generations.

To investigate the possibility of achieving targeted modifications without incorporating foreign DNA into the bread wheat genome, we designed PCR primers specific for the Ubiquitin 1 promoter driving the bar gene in plasmid pAHC20 and the TALEN gene in the T-MLO plasmid. The PCR assay failed to detect the Ubiquitin promoter in 45 out of 652 (6.9%) T1 plants derived from 9 T0 lines and 22 out of 105 (21.0%) T2 plants derived from 3 T1 lines (Table 6 and Table 4). Two TALEN-free tamlo-aabbdd homozygous mutant plants were obtained (Table 4). This indicates that a TALEN-free plant line that carries only the desired DNA sequence change can be obtained through genetic segregation.

Figure 2B:
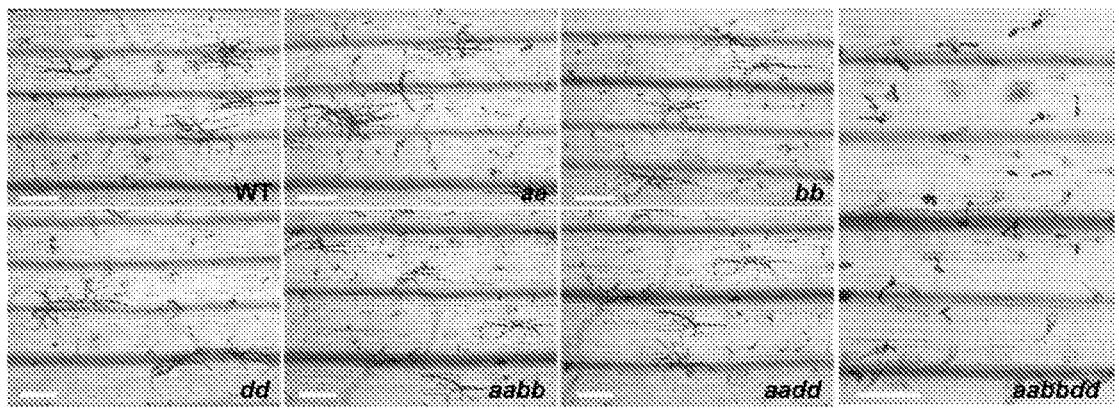
Figure 2C:
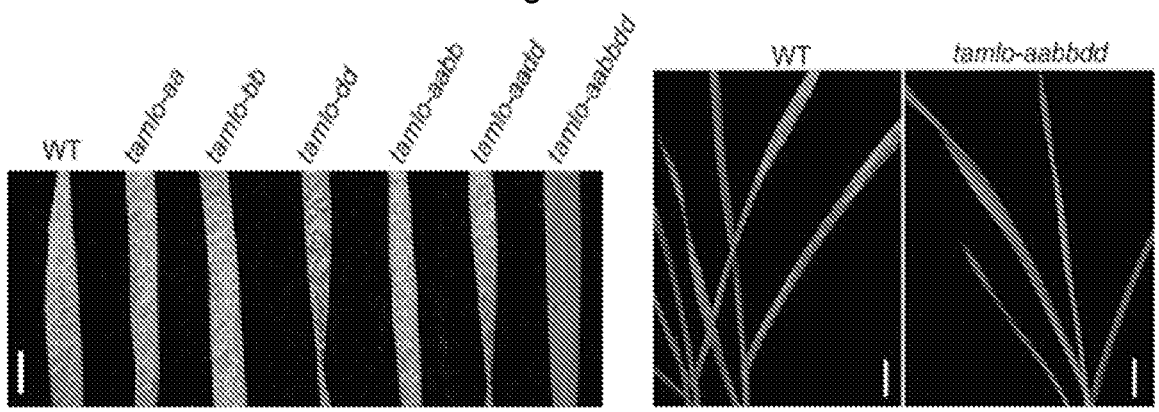
Figure 2D:
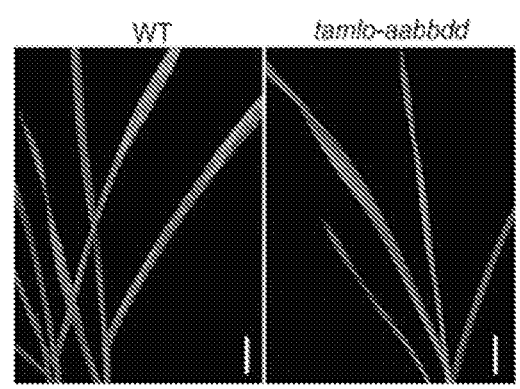

We assessed the impact of TALEN-induced mutations of TaMLO on wheat resistance to powdery mildew. All the combinations of the TaMLO-A1, TaMLO-B1 and TaMLO-D1 homozygous mutants (tamlo-aa, tamlo-bb, tamlo-dd, tamlo-aabb, tamlo-aadd, tamlo-bbdd and tamlo-aabbdd), were obtained by selfing and genotyped by RCR/RE and sequencing (FIG. 5). Seedling leaves of these bread wheat mutants (tamlo-aa, tamlo-bb, tamlo-dd, tamlo-aabb, tamlo-aadd and tamlo-aabbdd), were challenged with conidiospores of a virulent Bgt race. Microscopic examination showed that the number of mildew micro-colonies formed on the leaves was significantly reduced only in tamlo-aabbdd mutant plants (FIGS. 2a and 2b). Consistent with this finding, no apparent fungal growth was observed on the leaves of the tamlo-aabbdd plants, although abundant fungi were found on the leaves of wild type (WT) plants and those of the other mutant combinations (FIGS. 2c and 2d). The tamlo-aabbdd plants also exhibited strong resistance to several additional virulent Bgt races tested (FIG. 1). These results suggest that TaMLO-A1, TaMLO-B1 and TaMLO-D1 are all involved in the control of bread wheat response to Bgt infection, and that simultaneous mutation of the three homoeo-alleles confers broad-spectrum resistance to powdery mildew. To date, race-specific resistance controlled by the resistance (R) gene is commonly used for developing resistant wheat varieties, but this tends to break down as new Bgt races emerge in the field[32]. In contrast, loss-of-function mlo mutation-conferred resistance against powdery mildew has not been broken since its introgression into elite barley varieties three decades ago[25]. Therefore, the mlo-aabbdd alleles we generated in the elite wheat cultivars may provide excellent starting materials for breeding durable and broad-spectrum resistance in bread wheat.

We further demonstrated the application of SSNs in bread wheat by obtaining TaMLO mutant plants created with the CRISPR/Cas9 system. Previously, we reported that the CRISPR/Cas9 system could be used to induce sequence-specific genome modifications of MLO genes in wheat protoplasts[16]. Here, we used the T7 endonuclease I (T7E1) assay[21] to identify mutations induced by sgMLO-A1 in wheat protoplasts and transgenic plants (FIG. 7 and Table 1). So far we have identified mutations in TaMLO-A1. We found four independent mutants carrying mutations in TaMLO-A1 among 72 T0 transgenic wheat lines (FIG. 7c). This mutation frequency (5.6%) is similar to that obtained using TALENs (Table 3).

Figure 3A:
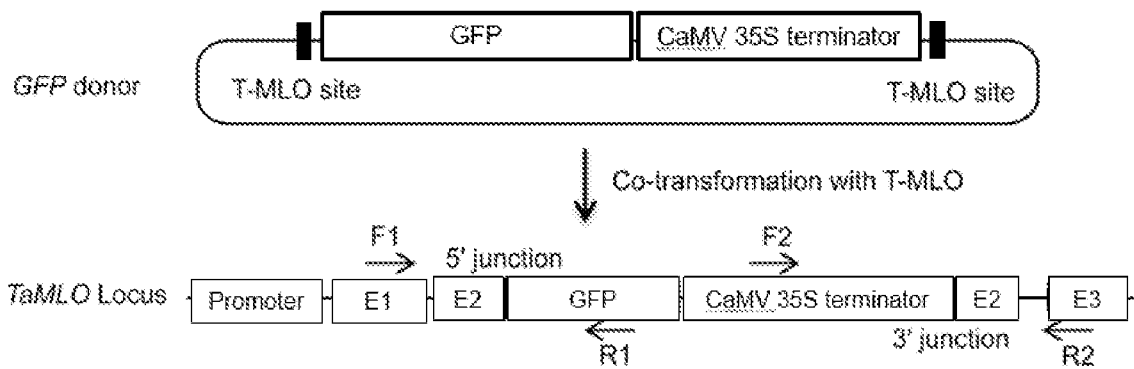
FIG. 3. Non-homologous end joining (NHEJ)-mediated knock-in of a GFP reporter gene at a TaMLO site in wheat protoplasts. (a) Structure of the GFP donor plasmid and the anticipated outcome of a GFP knock-in event. A cauliflower mosaic virus (CaMV) 35S terminator lies downstream of the GFP coding sequence. The cassette is flanked by two T-MLO sites, which generate a linear structure by recombination with the co-transformed T-MLO plasmid. The locations and names of the primers used for PCR analysis of knock-in events are shown. (b) Measurement of GFP knock-in efficiency in wheat protoplasts by flow cytometry. Three fields of protoplasts are shown. Protoplasts were transformed with the following DNA constructs (from left to right): 1) T-MLO plus GFP donor plasmids; 2) GFP donor plasmid alone; 3) Positive control with GFP-expression driven by the maize Ubiquitin 1 (Ubi-1) promoter. Flow cytometry was used to quantify the percentage of GFP-expressing protoplasts. Bar=100 µm. (c) Sequencing of 5' and 3' junctions confirm NHEJ-mediated knock-in events. The 5' junction sequences were PCR-amplified with primers F1 and R1, and the 3' junctions with primers and R2. T-MLO sites are underlined. There are inherent SNPs in the T-MLO site. The numbers on the right show the type of mutation and how many nucleotides are involved, with "−" and "+" indicating nucleotide deletion and insertion, respectively. SEQ ID NOS: 99-119.
Figure 3B:
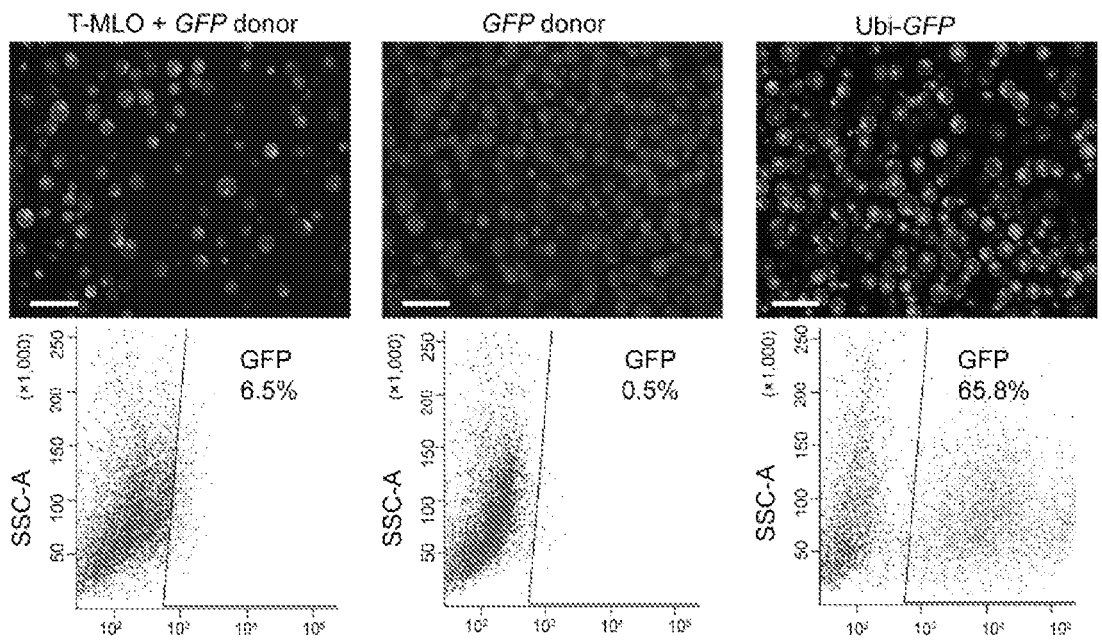
Figure 3C:

The important role of TaMLO genes in regulating powdery mildew disease resistance as described above prompted us to test if we could achieve gene addition downstream of their promoters via NHEJ at DSBs caused by TALENs, as this approach may be required for further improving the efficacy of TaMLO gene products. We constructed a donor vector containing a promoter-less GFP coding sequence and CaMV 35S terminator, flanked by T-MLO recognition sites (FIGS. 3a and 8) and co-transformed the T-MLO plasmid and the GFP donor vector into wheat protoplasts. Correct insertion of the GFP coding sequence into TaMLO loci rendered the protoplasts fluorescent (FIG. 3b). We detected significantly more fluorescent protoplasts from transformations with the TALENs and the GFP donor than with the GFP donor alone (FIG. 3b). Sequencing of PCR products of the genomic DNA of the transformed protoplasts confirmed that the GFP cassette had been inserted into the TaMLO loci, accompanied by small deletions and insertions due to NHEJ at the 5' and 3' junctions (FIG. 3c). We also tested targeted knock-in at the TaMLO loci with ssDNAs (ssDNA-1 and ssDNA-2) encoding His-tag and Myc-tag peptides, respectively (Table 5). The T-MLO plasmid and pAHC20, in combination with either ssDNA-1 or ssDNA-2, were co-transformed into immature wheat embryos via particle bombardment. The His-tag sequence was integrated in the correct orientation into TaMLO-A1 target site in one of 69 regenerated transgenic plants, while in 1 of 39 transgenic plants the Myc-tag sequence was integrated into TaMLO-B1 in the opposite orientation with two copies (Table 3). Analysis of T1 populations showed that the insertions were inherited in Mendelian fashion. These results demonstrate that targeted gene insertion via NHEJ is feasible in bread wheat, and may be used for further manipulating the function of TaMLO and other genes controlling important agronomic traits.

Crop improvement requires the constant creation and use of new allelic variants. The great promise of genome editing for crop improvement has only now begun to be realized, and has only been demonstrated in very few cases. Our study proves that TALENs and the CRISPR/Cas9 system can be used to generate novel genetic traits in hexaploid bread wheat. In addition, we show that targeted DNA insertion can be achieved through the NHEJ pathway. The latter strategy should be valuable for creating traits that cannot be produced by simple mutagenesis. Our work presents a successful example of the use of SSNs for molecular breeding of bread wheat. The rapidity and precision with which changes can be achieved by this approach should definitely help to improve wheat at a rate sufficient to guarantee world food security.

TABLE 1

SSN target loci and sequences

| Gene Name | SSN ID | Target Site | Left Binding Site RVDs/Oligo-F (5'-3') | Right Binding Site RVDs/Oligo-R (5'-3') | Detection method |
| --- | --- | --- | --- | --- | --- |
| TaMLO | T-MLO | TCGCTGCTGCTCGCCGTg acgcaggacccccatctcC GGGATATGCATCTCCGA SEQ ID NO. 13 | HD NN HD NG NN HD NG NN HD NG HD NN HD HD NN NG | HD NN NN NI NN NI NG NN HD NI NG NI NG HD HD HD NN | PCR/RE:AvaII |
| TaMLO-A1 | sgMLO-A1 | CCGTCACGCAGGACCCAA TCTCC SEQ ID No. 17 | CTTGGAGATTGGGTCCTGCG TGA SEQ ID No. 26 | AAACTCACGCAGGACCCAAT CTC SEQ ID No. 27 | T7E1 |

TABLE 2

PCR primers used and their applications

| Primer name | Primer sequence | Experiment |
| --- | --- | --- |
| MLO-A1-F | TGGCGCTGGTCTTCGCCGTCATGATCATCGTC SEQ ID No. 18 | Gene specific primer amplifying the TaMLO-A1 target site |
| MLO-A1-R | TACGATGAGCGCCACCTTGCCCGGGAA SEQ ID No. 19 | |
| MLO-B1-F | ATAAGCTCGGCCATGTAAGTTCCTTCCCGG SEQ ID No. 20 | Gene specific primer amplifying the TaMLO-B1 target site |
| MLO-B1-R | CCGGCCGGAATTTGTTTGTGTTTTTGTT SEQ ID No. 21 | |
| MLO-D1-F | TGGCTTCCTCTGCTCCCTTGGTGCACCT SEQ ID No. 22 | Gene specific primer amplifying the TaMLO-D1 target site |
| MLO-D1-R | TGGAGCTGGTGCAAGCTGCCCGTGGACATT SEQ ID No. 23 | |
| MLO-F | GTCTTCGCCGTCATGATCATCGTCTCC SEQ ID No. 24 | Amplifying the TaMLO target site: This primer can be used to amplify all three alleles |
| MLO-R | TGGTATTCCAAGGAGGCGGTCTCTGTCT SEQ ID No. 25 | |

TABLE 2-continued

PCR primers used and their applications

| Primer name | Primer sequence | Experiment |
| --- | --- | --- |
| F1 | GTCTTCGCCGTCATGATCATCGTCTCC<br>SEQ ID No. 28 | Detecting NHEJ-mediated GFP inserts |
| R1 | GGTGCTCAGGTAGTGGTTGTC<br>SEQ ID No. 29 | |
| F2 | CTTTGTCGTGAATATAAACCAGACACGAG<br>SEQ ID No. 30 | Detecting NHEJ-mediated GFP inserts |
| R2 | TGGTATTCCAAGGAGGCGGTCTCTGTCT<br>SEQ ID No. 31 | |
| Ubi-F | CAGTTAGACATGGTCTAAAGGACAATTGAG<br>SEQ ID No. 32 | Detecting the absence of TALENs |
| Ubi-R | CCAACCACCACCACATCATCACAACCAA<br>SEQ ID No. 33 | |

The gene specific primers amplify both wild type and mutant TaMLO genes.

TABLE 3

Frequencies of SSN-induced knockout and knock-in mutations in transgenic wheat plants (T0).

| Gene Name | SSN ID | Varieties | Experiment No. | Total number of plants tested | Number of mutated plants | Mutation frequency (%)[a] |
| --- | --- | --- | --- | --- | --- | --- |
| TaMLO | T-MLO | Kenong199 | 1 | 45 | 3 | 6.7 |
| | | | 2 | 64 | 4 | 6.3 |
| | | | 3 | 51 | 3 | 5.9 |
| | | | 4 | 92 | 5 | 5.4 |
| | | | 5 | 198 | 12 | 6.1 |
| | | Bobwhite | 1 | 237 | 8 | 3.4 |
| | T-MLO + ssDNA1 | Kenong199 | 1 | 69 | 1 | 1.4 |
| | T-MLO + ssDNA2 | Kenong199 | 1 | 39 | 1 | 2.6 |
| | sgMLO-A1 | Kenong199 | 1 | 72 | 4 | 5.6 |

[a]Based on the number of mutated plants over the total number of plants tested.

TABLE 4

Molecular and genetic analysis of TALEN-induced mutations in TaMLO homologs and their transmission to T2 generation.

| | Analysis of T1 plants | | Mutation segregation in T2 | | | | | |
| --- | --- | --- | --- | --- | --- | --- | --- | --- |
| Plant ID | Genotype of TaMLO homoeologs | Mutation detected (bp) | No. of tested plants | WT | Hetero | Homo | Mutation transmission (%)[a] | TALEN-free (%)[b] |
| T0-2-15[c] | aa | −3 | 37 | 0 (AA) | 0 (Aa) | 37 (aa) | 100 | 100 |
| T0-2-26 | Aa | −3 | 42 | 11 (AA) | 19 (Aa) | 12 (aa) | 73.5* | 14.2 |
| | aa | −32 | | 0 (AA) | 0 (Aa) | 24 (aa) | 100 | |
| T0-3-2 | Bb | +141 | 24 | 6 (BB) | 11 (Bb) | 7 (bb) | 75* | 16.7 |
| | dd | −11/+81 | | 0 (DD) | 0 (Dd) | 24 (dd) | 100 | |
| T0-5-4[c] | dd | −5 | 83 | 0 (DD) | 0 (Dd) | 83 (dd) | 100 | 100 |
| T0-8-12 | aa | −7 | 39 | 0 (AA) | 0 (Aa) | 39 (aa) | 100 | 30.8 |
| | Bb | −2/+113 | | 8 (BB) | 19 (Bb) | 12 (bb) | 79.5* | |
| T0-11-9[c] | Aa | −3/+61 | 52 | 14 (AA) | 27 (Aa) | 11 (aa) | 73.1* | 100 |
| | dd | −29 | | 0 (DD) | 0 (Dd) | 52 (dd) | 100 | |

[a]based on the number of plants carrying the observed mutation over the total number of plants tested;
[b]absence of intact TALEN construct and herbicide-resistance gene; based on the number of mutant plants not harbouring the Ubiquitin promoter over the total number of plants tested;
[c]TALEN-free plants selected from T1 generation;
*showing that the segregation of the heterozygous lines conforms to the Mendelian 1:2:1 ratio according to the $\chi^2$ test (P > 0.5);
WT, wild-type; Hetero, heterozygous; Homo, homozygous; −n, deletion of indicated number of nucleotides; +n, insertion of indicated number of nucleotides; −n/+n, simultaneous deletion and insertion of the indicated numbers of nucleotide at the same site; −n, . . . −n, multiple types of deletions occurred in different mutation events of the same target site.

TABLE 5

Sequences of the single-stranded DNA oligonucleotide donors.

| Donor name | Target site | Oligonucleotide sequence (5'-3') |
|---|---|---|
| ssDNA-1 | TaMLO | TTCGACTGGTCGGTGCGCGGTCACCCCATCATCATCATCATCAC SEQ ID No. 34 TCACCACGGGCGAGAACAAGGT SEQ ID No. 35 |
| ssDNA-2 |  | CGCTGCTGCTCGCCGTCACGCAGAACAGAAACTGATCTCTGAAG SEQ ID No. 36 AAGACCTGCCATCTCCGGGATATGCATCTCC SEQ ID No. 37 |

TABLE 6

Molecular and genetic analysis of TALEN-induced mutations in TaMLO homoeologs and their transmission to T1 generation.

| | Analysis of T0 plants | | | Mutation segregation in T1 population | | | | |
|---|---|---|---|---|---|---|---|---|
| Plant ID | Genotype of TaMLO homoeologs | Mutation detected (bp) | No. of tested plants | WT | Hetero | Homo | Mutation transmission (%)[a] | TALEN-free (%)[b] |
| T0-2 | Aa | −3 |  | 11 (AA) | 31 (Aa) | 14 (aa) | 80.4* | 5.4 |
|  | BB |  | 56 | 54 (BB) | 2 (Bb) | 0 (bb) |  | 0 |
|  | DD |  |  | 53 (DD) | 3 (Dd) | 0 (add) |  | 0 |
| T0-3 | Aa | −32 |  | 1 (AA) | 1 (Aa) | 1 (aa) | 66.7 |  |
|  | Bb | +141 | 3 | 0 (BB) | 3 (Bb) | 0 (bb) | 100 | 0 |
|  | Dd | −11/+81 |  | 0 (DD) | 0 (Dd) | 3 (dd) | 100 |  |
| T0-4 | AA |  |  | 114 (AA) | 9 (Aa) | 0 (aa) |  | 0 |
|  | BB |  | 123 | 121 (BB) | 2 (Bb) | 0 (bb) |  | 0 |
|  | Dd | −5 |  | 30 (DD) | 73 (Dd) | 20 (dd) | 75.6* | 8.1 |
| T0-5 | Dd | −5 | 149 | 25 (DD) | 95 (Dd) | 29 (dd) | 83.2* | 6.0 |
| T0-6 | Aa | −2, −4, −3, −6 | 68 | 58 (AA) | 10 (Aa) | 0 (aa) | 14.7 | 1.5 |
|  | AA |  |  | 47 (AA) | 1 (Aa) | 0 (aa) |  | 0 |
| T0-7 | BB |  | 48 | 46 (BB) | 2 (Bb) | 0 (bb) |  | 0 |
|  | Dd | −2 |  | 4 (DD) | 36 (Dd) | 8 (dd) | 91.7 | 8.3 |
| T0-8 | aa | −3, −7 | 58 | 0 (AA) | 0 (Aa) | 58 (aa) | 100 | 12.1 |
|  | Bb | −2/+113 |  | 16 (BB) | 31 (Bb) | 11 (bb) | 72.4* |  |
| T0-9 | Aa | −10 | 59 | 17 (AA) | 25 (Aa) | 15 (aa) | 67.8* | 6.8 |
|  | Dd | −2, −4, −5 |  | 54 (DD) | 5 (Dd) | 0 (dd) | 8.5 |  |
| T0-11 | Aa | −3/+61 | 88 | 23 (AA) | 44 (Aa) | 21 (aa) | 73.9* | 8.0 |
|  | Dd | −29 |  | 21 (DD) | 41 (Dd) | 26 (dd) | 76.1* |  |

[a]based on the number of plants carrying the observed mutation over the total number of plants tested;
[b]absence of intact TALEN construct and herbicide-resistance gene; based on the number of mutant plants not haboring the Ubiquitin-1 promoter over the total number of plants tested
*indicating that the segregation of the heterozygous lines conforms to the Mendelian 1:2:1 ratio according to $\chi^2$ test (P > 0.5); WT, wild-type; Hetero, heterozygous; Homo, homozygous; −n, deletion of indicated number of nucleotides; +n, insertion of indicated number of nucleotides; −n/+n, simultaneous deletion and insertion of the indicated numbers of nucleotide at the same site; −n, . . . −n, multiple types of deletions occurring in different mutation events at the same target site.

REFERENCES

All references are incorporated herein by reference.
1. Voytas, D. F. Plant genome engineering with sequence-specific nucleases. *Annu. Rev. Plant. Biol.* 64, 327-350 (2013).
2. Bogdanove, A. J. & Voytas, D. F. TAL effectors: customizable proteins for DNA pargeting. *Science* 333, 1843-1846 (2011).
3. Jinek, M. et al. A programmable dual-RNA-guided DNA endonuclease in adaptive bacterial immunity. *Science* 337, 816-821 (2012).
4. Várallyay, É., Giczey, G. & Burgyán, J. Virus-induced gene silencing of Mlo genes induces powdery mildew resistance in *Triticum aestivum. Arch. Virol.* 157, 1345-1350 (2012).
5. Slade, A. J. et al. A reverse genetic, nontransgenic approach to wheat crop improvement by TILLING. *Nat. Biotechnol.* 23, 75-81 (2005).
6. Dvorak, J. in Genetics and Genomics of the Triticeae, Vol. 7. (eds. G. J. Muehlbauer & C. Feuillet) 685-711 (Springer US, 2009).
7. Bibikova, M., Beumer, K., Trautman, J. K. & Carroll, D. Enhancing gene targeting with designed zinc finger nucleases. *Science* 300, 764 (2003).
8. Gorbunova, V. & Levy, A. A. Non-homologous DNA end joining in plant cells is associated with deletions and filler DNA insertions. *Nucleic Acids Res.* 25, 4650-4657 (1997).
9. Puchta, H., Dujon, B. & Hohn, B. Homologous recombination in plant cells is enhanced by in vivo induction of double strand breaks into DNA by a site-specific endonuclease. *Nucleic Acids Res.* 21, 5034-5040 (1993).
10. Zhang, F. et al. High frequency targeted mutagenesis in *Arabidopsis thaliana* using zinc-finger nucleases. *Proc. Nat.l Acad. Sci.* 107, 12028-12033 (2010).
11. Feng, Z. et al. Multigeneration analysis reveals the inheritance, specificity, and patterns of CRISPR/Cas-induced gene modifications in *Arabidopsis. Proc. Nat.l Acad. Sci.* doi:10.1073/pnas.1400822111 (2014).
12. Zhang, Y. et al. Transcription activator-like effector nucleases enable efficient plant genome engineering. *Plant physiol.* 161, 20-27 (2013).
13. Wendt, T. et al. TAL effector nucleases induce mutations at a pre-selected location in the genome of primary barley transformants. *Plant Mol. Biol.* 83, 279-285 (2013).
14. Gurushidze, M. et al. True-breeding targeted gene knock-out in barley using designer TALE-nuclease in haploid cells. *PloS one* 9, e92046. doi:10.1371/journal.pone.0092046 (2014).
15. Curtin, S. J. et al. Targeted mutagenesis of duplicated genes in soybean with zinc-finger nucleases. *Plant physiol.* 156, 466-473 (2011).
16. Shan, Q. et al. Rapid and efficient gene modification in rice and brachypodium using TALENs. *Mol. Plant* 6, 1365-1368 (2013).
17. Shan, Q. et al. Targeted genome modification of crop plants using a CRISPR-Cas system. *Nat. Biotechnol.* 31, 686-688 (2013).
18. Li, T. et al. High-efficiency TALEN-based gene editing produces disease-resistant rice. *Nat. Biotechnol.* 30, 390-392 (2012).
19. Feng, Z. et al. Efficient genome editing in plants using a CRISPR/Cas system. *Cell Res.* 23, 1229-1232 (2013).
20. Miao, J. et al. Targeted mutagenesis in rice using CRISPR-Cas system. *Cell Res.* 23, 1233-1236 (2013).
21. Xie, K. & Yang, Y. RNA-guided genome editing in plants using a CRISPR-Cas system. *Mol. Plant.* doi: 10.1093/mp/sst119 (2013).
22. Shukla, V. K. et al. Precise genome modification in the crop species *Zea mays* using zinc-finger nucleases. *Nature* 459, 437-441 (2009).
23. Liang, Z., Zhang, K., Chen, K. & Gao, C. Targeted mutagenesis in *zea mays* using TALENs and the CRISPR/Cas system. *J. Genet. Genomics* 41, 63-68 (2014).
24. Christian, M., Qi, Y., Zhang, Y. & Voytas, D. F. Targeted mutagenesis of *Arabidopsis thaliana* using engineered TAL effector nucleases. *G3 (Bethesda)* 3, 1697-1705 (2013).
25. Büschges, R. et al. The barley Mlo gene: A novel control element of plant pathogen resistance. *Cell* 88, 695-705 (1997).
26. Piffanelli, P. et al. A barley cultivation-associated polymorphism conveys resistance to powdery mildew. *Nature* 430, 887-891 (2004).
27. Consonni, C. et al. Conserved requirement for a plant host cell protein in powdery mildew pathogenesis. *Nat. Genet.* 38, 716-720 (2006).
28. Bai, Y. et al. Naturally occurring broad-spectrum powdery mildew resistance in a central american tomato accession is caused by loss of mlo function. *Mol. Plant Microbe In.* 21, 30-39 (2007).
29. Elliott, C. et al. Functional conservation of wheat and rice Mlo orthologs in defense modulation to the powdery mildew fungus. *Mol. Plant Microbe In.* 15, 1069-1077 (2002).
30. Cermak, T. et al. Efficient design and assembly of custom TALEN and other TAL effector-based constructs for DNA targeting. *Nucleic Acids Res.* 39 (2011).
31. Christensen, A. & Quail, P. Ubiquitin promoter-based vectors for high-level expression of selectable and/or screenable marker genes in monocotyledonous plants. *Transgenic. Res.* 5, 213-218 (1996).
32. McDonald, B. A. & Linde, C. Pathogen population genetics, evolutionary potential, and durable resistance. *Annu. Re. Phytopathol.* 40, 349-379 (2002).
33. Cermak, T. et al. Efficient design and assembly of custom TALEN and other TAL effector-based constructs for DNA targeting. *Nucleic Acids Res.* 39, 1-11 (2011).
34. Zhang, Y. et al. Transcription activator-like effector nucleases enable efficient plant genome engineering. *Plant physiol.* 161, 20-27 (2013).
35. Shan, Q. et al. Rapid and efficient gene modification in rice and brachypodium using TALENs. *Mol. Plant* 6, 1365-1368 (2013).
36. Shan, Q. et al. Targeted genome modification of crop plants using a CRISPR-Cas system. *Nat. Biotechnol.* 31, 686-688 (2013).
37. Rasco-Gaunt, S. et al. Procedures allowing the transformation of a range of European elite wheat (*Triticum aestivum* L.) varieties via particle bombardment. *J. Exp Bot.* 52, 865-874 (2001).
38. Xie, K. & Yang, Y. RNA-guided genome editing in plants using a CRISPR-Cas system. Molecular plant 6, 1975-1983 (2013).
39. Hein, I. et al. Virus-induced gene silencing-based functional characterization of genes associated with powdery mildew resistance in barley. *Plant physiol.* 138, 2155-2164 (2005).
40. Acevedo-Garcia et al: magical Mystery tour: MLO proteins in plant immunity and beyond. *New Phytologist.* 1-9 (2014)
41. Hsu et al: Development and Applications of CRISPR-Cas9 for Genome Engineering. *Cell* 157, 1262-1278, 2014

SEQUENCE LISTING

```
Coding sequence of TaMLO-A1:160 5bp;
The TALEN target site is indicated underlined.
                                        SEQ ID NO. 1
ATGGCGGAGGACGACGGGTACCCCCCGGCGCGGACGCTGCCGGAGACGCC
GTCCTGGGCGGTGGCGCTGGTCTTCGCCGTCATGATCATCGTCTCCGTCC
TCCTGGAGCACGCGCTCCACAAGCTCGGCCAGTGGTTCCACAAGCGGCAC
AAGAACGCGCTGGCGGAGGCGCTGGAGAAGATGAAGGCGGAGCTGATGCT
GGTGGGATTCATCTCGCTGCTGCTCGCCGTCACGCAGGACCCAATCTCCG
GGATATGCATCTCCCAGAAGGCCGCCAGCATCATGCGCCCCTGCAAGGTG
GAACCCGGTTCCGTCAAGAGCAAGTACAAGGACTACTACTGCGCCAAAGA
GGGCAAGGTGGCGCTCATGTCCACGGGCAGCCTGCACCAGCTCCACATAT
TCATCTTCGTGCTAGCCGTCTTCCATGTCACCTACAGCGTCATCATCATG
GCTCTAAGCCGTCTCAAGATGAGAACATGGAAGAAATGGGAGACAGAGAC
CGCCTCCTTGGAATACCAGTTCGCAAATGATCCTGCGCGGTTCCGCTTCA
CGCACCAGACGTCGTTCGTGAAGCGGCACCTGGGCCTGTCCAGCACCCCC
GGCGTCAGATGGGTGGTGGCCTTCTTCAGGCAGTTCTTCAGGTCGGTCAC
CAAGGTGGACTACCTCACCTTGAGGGCAGGCTTCATCAACGCGCACTTGT
CGCAGAACAGCAAGTTCGACTTCCACAAGTACATCAAGAGGTCCATGGAG
GACGACTTCAAAGTCGTCGTTGGCATCAGCCTCCCGCTGTGGGCTGTGGC
GATCCTCACCCTCTTCCTTGATATCGACGGGATCGGCACACTCACCTGGG
TTTCTTTCATCCCTCTCATCATCCTCTTGTGTGTTGGAACCAAGCTAGAG
ATGATCATCATGGAGATGGCCCTGGAGATCCAGGACCGGTCGAGCGTCAT
CAAGGGGGCACCCGTGGTCGAGCCCAGCAACAAGTTCTTCTGGTTCCACC
GCCCCGACTGGGTCCTCTTCTTCATACACCTGACGCTGTTCCAGAACGCG
TTTCAGATGGCACATTTCGTGTGGACAGTGGCCACGCCCGGCTTGAAGGA
CTGCTTCCATATGAACATCGGGCTGAGCATCATGAAGGTCGTGCTGGGGC
TGGCTCTCCAGTTCCTCTGTGCAGCTACATCACCTTCCCCCCTCTACGCGCTA
GTCACACAGATGGGGATCAAACATGAAGAGGTCCATCTTCGACGAGCAGAC
AGCCAAGGCGCTGACCAACTGGCGGAACACGGCCAAGGAGAAGAAGAAGG
TCCGAGACACGGACATGCTGATGGCGCAGATGATCGGCGACGCAACACCC
AGCCGAGGCACGTCCCCGATGCCTAGCCGGGGCTCATCGCCGGTGCACCT
GCTTCAGAAGGGCATGGGACGGTCTGACGATCCCCAGAGCGCACCGACCT
CGCCAAGGACCATGGAGGAGGCTAGGGACATGTACCCGGTTGTGGTGGCG
CATCCTGTACACAGACTAAATCCTGCTGACAGGAGAAGGTCGGTCTCTTC
ATCAGCCCTCGATGCCGACATCCCCAGCGCAGATTTTTCCTTCAGCCAGG
GATGA
```

-continued

Coding sequence of TaMLO-B1:1605 bp; The TALEN
target site is indicated underlined.
SEQ ID NO. 2

```
ATGGCGGAGGACGACGGGTACCCCCCAGCGAGGACGCTGCCGGAGACGCC
GTCCTGGGCGGTGGCCCTCGTCTTCGCCGTCATGATCATCGTGTCCGTCC
TCCTGGAGCACGCGCTCCATAAGCTCGGCCAGTGGTTCCACAAGCGGCAC
AAGAACGCGCTGGCGGAGGCGCTGGAGAAGATCAAGGCGGAGCTCATGCT
GGTGGGCTTCATCTCGCTGCTGCTCGCCGTGACGCAGGACCCCATCTCCG
GGATATGCATCTCCGAGAAGGCCGCCAGCATCATGCGGCCCTGCAAGCTG
CCCCCTGGCTCCGTCAAGAGCAAGTACAAAGACTACTACTGCGCCAAACA
GGGCAAGGTGTCGCTCATGTCCACGGGCAGCTTGCACCAGCTGCACATAT
TCATCTTCGTGCTCGCCGTCTTCCATGTCACCTACAGCGTCATCATCATG
GCTCTAAGCCGTCTCAAGATGAGGAACCTGGAAGAAATGGGAGACAGAGA
CGCCTCCCTGGAATACCAGTTCGCAAATGATCCTGCGCGGTTCCGCTTCA
CGCACCAGACGTCGTTCGTGAAGCGGCACCTGGGCCTCTCCAGCACCCCC
GGCGTCAGATGGGTGGTGGCCTTCTTCAGGCAGTTCTTCAGGTCGGTCAC
CAAGGTGGACTACCTCACCTTGAGGGCAGGCTTCATCAACGCGCATTTGT
CGCATAACAGCAAGTTCGACTTCCACAAGTACATCAAGAGGTCCATGGAG
GACGACTTCAAAGTCGTCGTTGGCATCAGCCTCCCGCTGTGGTGTGTGGC
GATCCTCACCCTCTTCCTTGACATTGACGGGATCGGCACGCTCACCTGGA
TTTCTTTCATCCCTCTCGTCATCCTCTTGTGTGTTGGAACCAAGCTGGAG
ATGATCATCATGGAGATGGCCCTGGAGATCCAGGACCGGGCGAGCGTCAT
CAAGGGGGCGCCCGTGGTTGAGCCCAGCAACAAGTTCTTCTGGTTCCACC
GCCCCGACTGGGTCCTCTTCTTCATACACCTGACGCTATTCCAGAACGCG
TTTCAGATGGCACATTTCGTGTGGACAGTGGCCACGCCCGGCTTGAAGAA
ATGCTTCCATATGCACATCGGGCTGAGCATCATGAAGGTCGTGCTGGGGC
TGGCTCTTCAGTTCCTCTGCAGCTATATCACCTTCCCGCTCTACGCGCTC
GTCACACAGATGGGATCAAACATGAAGAGGTCCATCTTCGACGAGCAGAC
GGCCAAGGCGCTGACAAACTGGCGGAACACGGCCAAGGAGAAGAAGAGG
TCCGAGACACGGACATGCTGATGGCGCAGATGATCGGCGACGCGACGCCC
AGCCGAGGGCGTCGCCCATGCCTAGCCGGGGCTCGTCGCCAGTGCACCT
GCTTCACAAGGGCATGGGACGGTCCGACGATCCCAGAGCACGCCAACCT
CGCCAAGGGCCATGGAGGAGGCTAGGGACATGTACCCGGTTGTGGTGGCG
CATCCAGTGCACAGACTAAATCCTGCTGACAGGAGAAGGTCGGTCTCGTC
GTCGGCACTCGATGTCGACATTCCCAGCGCAGATTTTCCTTCAGCCAGG
GATGA
```

Coding sequence of TaMLO-D1:1605 bp; The TALEN
target site is indicated underlined.
SEQ ID NO. 3

```
ATGGCGGAGGACGACGGGTACCCCCGGCGCGGACGCTGCCGGAGACGCC
GTCCTGGGCGGTGGCCCTCGTCTTCGCCGTCATGATCATCGTGTCCGTCC
TCCTGGAGCACGCGCTCCACAAGCTCGGCCAGTGGTTCCACAAGCGGCAC
AAGAACGCGCTGGCGGAGGCGCTGGAGAAGATCAAAGCGGAGCTGATGCT
GGTGGGGTTCATCTCGCTGCTGCTCGCCGTGACGCAGGACCCCAATCTCC
GGATATGCATCTCCGAGAAGGCCGCCAGCATCATGCGGCCCTGCAAGCTG
CCCCCTGGTTCCGTCAAGAGCAAGTACAAAGACTACTACTGCGCCAAAAA
GGGCAAGGTGTCGCTAATGTCCACGGGCAGCTTGCACCAGCTCCACATAT
TCATCTTCGTGCTCGCCGTCTTCCATGTCACCTACAGCGTCATCATCATG
GCTCTAAGCCGTCTCAAGATGAGGACATGGAAGAAATGGGAGACAGAGA
CGCCTCCTTGGAATACCAGTTCGCAAATGATCCTGCGCGGTTCCGCTTCA
CGCACCAGACGTCGTTCGTGAAGCGTCACCTGGGCCTCTCCAGCACCCCC
GGCATCAGATGGGTGGTGGCCTTCTTCAGGCAGTTCTTCAGGTCGGTCAC
CAAGGTGGACTACCTCACCCTGAGGGCAGGCTTCATCAACGCGCATTTGT
CGCATAACAGCAAGTTCGACTTCCACAAGTACATCAAGAGGTCCATGGAG
GACGACTTCAAAGTCGTCGTTGGCATCAGCCTCCCGCTGTGGTGTGTGGC
GATCCTCACCCTCTTCCTTGATATTGACGGGATCGGCACGCTCACCTGGA
TTTCTTTCATCCCTCTCGTCATCCTCTTGTGTGTTGGAACCAAGCTGGAG
ATGATCATCATGGAGATGGCCCTGGAGATCCAGGACCGGGCGAGCGTCAT
CAAGGGGGCGCCCGTGGTTGAGCCCAGCAACAAGTTCTTCTGGTTCCACC
GCCCCGACTGGGTCCTCTTCTTCATACACCTGACGCTGTTCCAGAATGCG
TTTCAGATGGCACATTTCGTCTGGACAGTGGCCACGCCCGGCTTGAAGAA
ATGCTTCCATATGCACATCGGGCTGAGCATCATGAAGGTCGTGCTGGGGC
TGGCTCTTCAGTTCCTCTGCAGCTATATCACCTTCCCGCTCTACGCGCTC
GTCACACAGATGGGATCAAACATGAAGAGGTCCATCTTCGACGAGCAGAC
GGCCAAGGCGCTGACAAACTGGCGGAACACGGCCAAGGAGAAGAAGAAGG
TCCGAGACACGGACATGCTGATGGCGCAGATGATCGGCGACGCGACGCCC
AGCCGAGGGCGTCGCCCATGCCTAGCCGGGGCTCGTCGCCAGTGCACCT
GCTTCACAAGGGCATGGGACGGTCCGACGATCCCAGAGCACGCCAACCT
CGCCAAGGGCCATGGAGGAGGCTAGGGACATGTACCCGGTTGTGGTGGCG
CATCCAGTGCACAGACTAAATCCTGCTGACAGGAGAAGGTCGGTCTCTTC
GTCGGCACTCGATGCCGACATCCCCAGCGCAGATTTTCCTTCAGCCAGG
GATGA
```

The amino acid sequence of TaMLO-A1:534 aa.
SEQ ID NO. 4

```
MAEDDGYPPARTLPETPSWAVALVFAVMIIVSVLLEHALHKLGQWFHKRH
KNALAEALEKMKAELMLVGFISLLLAVTQDPISGICISQKAASIMRPCKV
EPGSVKSKYKDYYCAKEGKVALMSTGSLHQLHIFIFVLAVFHVTYSVIIM
ALSRLKMRTVVKKWETETASLEYQFANDPARFRFTHQTSFVKRHLGLSST
PGVRWVVAFFROFFRSVTKVDYLTLRAGFINAHLSQNSKFDFHKYIKRSM
EDDFKVVVGISLPLWAVAILTLFLDIDGIGTLTVVVSFIPLIILLCVGTK
LEMIIMEMALEIQDRSSVIKGAPVVEPSNKFFWFHRPDWVLFFIHLTLFQ
NAFQMAHFVWTVATPGLKDCFHMNIGLSIMKVVLGLALQFLCSYITFPLY
ALVTQMGSNMKRSIFDEQTAKALTNWRNTAKEKKVRDTDMLMAQMIGDA
TPSRGTSPMPSRGSSPVHLLQKGMGRSDDPQSAPTSPRTMEEARDMYPVV
VAHPVHRLNPADRRRSVSSSALDADIPSADFSFSQG
```

The amino acid sequence of TaMLO-B1:534 aa.
SEQ ID NO. 5

```
MAEDDGYPPARTLPETPSWAVALVFAVMIIVSVLLEHALHKLGQWFHKRH
KNALAEALEKIKAELMLVGFISLLLAVTQDPISGICISEKAASIMRPCKL
PPGSVKSKYKDYYCAKQGKVSLMSTGSLHQLHIFIFVLAVFHVTYSVIIM
ALSRLKMRTWKKWETETASLEYQFANDPARFRFTHQTSFVKRHLGLSSTP
GVRWVVAFFRQFFRSVTKVDYLTLRAGFINAHLSHNSKFDFHKYIKRSME
DDFKVVVGISLPLWCVAILTLFLDIDGIGTLTWISFIPLVILLCVGTKLE
MIIMEMALEIQDRASVIKGAPVVEPSNKFFWFHRPDWVLFFIHLTLFQNA
FQMAHFVWTVATPGLKKCFHMIGLSIMKVVLGLALQFLCSYITFPLYAL
VTQMGSNMKRSIFDEQTAKALTNWRNTAKEKKKVRDTDMLMAQMIGDATP
SRGASPMPSRGSSPVHLLHKGMGRSDDPQSTPTSPRAMEEARDMYPVVVA
HPVHRLNPADRRRSVSSSALDVDIPSADFSFSQG
```

The amino acid sequence of TaMLO-D1: 534 aa
SEQ ID NO. 6

```
MAEDDGYPPARTLPETPSWAVALVFAVMIIVSVLLEHALHKLGQWFHKRH
KNALAEALEKIKAELMLVGFISLLLAVTQDPISGICISEKAASIMRPCSL
PPGSVKSKYKDYYCAKKGKVSLMSTGSLHQLHIFIFVLAVFHVTYSVIIM
ALSRLKMRTWKKWETETASLEYQFANDPARFRFTHQTSFVKRHLGLSSTP
GIRWVVAFFROFFRSVTKVDYLTLRAGFINAHLSHNSKFDFHKYIKRSME
DDFKVVVGISLPLWCVAILTLFLDIDGIGTLTWISFIPLVILLCVGTKLE
MIIMEMALEIQDRASVIKGAPVVEPSNKFFWFHRPDWVLFFIHLTLFQNA
FQMAHFVWTVATPGLKKCFHMIGLSIMKVVLGLALQFLCSYITFPLYAL
VTQMGSNMKRSIFDEQTAKALTNWRNTAKEKKKVRDTDMLMAQMIGDATP
SRGASPMPSRGSSPVHLLHKGMGRSDDPQSTPTSPRAMEEARDMYPVVVA
HPVHRLNPADRRRSVSSSALDADIPSADFSFSQG
```

The coding sequence of TALENs (TAL-L + TAL-R) in
vector pYP010.T2A motif site is indicated as
underlined and bold.
SEQ ID NO. 11

```
ATGGTGGATCTACGCACGCTCGGCTACAGTCAGCAGCAGCAAGAGAAGAT
CAAACCGAAGGTGCGTTCGACAGTGGCGCAGCACCACGAGGCACTGGTGG
GCCATGGGTTTACACACGCGCACATCGTTGCGCTCAGCCAACACCCGGCA
GCGTTAGGGACCGTCGCTGTCACGTATCAGCACATAATCACGGCCGTTGCC
AGAGGCGACACACGAAGACATCGTTGGCGTCGGCAAACAGTGGTCCGGCG
CACGCGCCCTGGAGGCCTTGCTCACGGATGCGGGGGAGTTGAGAGGTCCG
CCGTTACAGTTGGACACAGGCCAACTTGTGAAGATTGCAAAACGTGGCGG
CGTGACCGCAATGGAGGCAGTGCATGCATCGCGCAATGCACTGACGGTG
CCCCCCTGAACCTGACCCCGGACCAAGTGGTGGCTATCGCCAGCACGAT
GGCGGCAAGCAAGCGCTCGAAACGGTGCAGCGGCTGTTGCCGGTGCTGTG
CCAGGACCATGGCCTGACCCCCGGACCAAGTGGTGGCTATCGCCAACAA
ATGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGC
TGTGCCAGGACCATGGCCTGACCCCCGAACAAGTGGTGGCTATCGCCAGC
AACGGTGGCGGCAAGCAAGCGCTCGAAACGGTGCAGCGGCTGTTGCCGGT
GCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCG
GTGCTGTGCCAGGACCATGGCCTGACTCCGGACCAAGTGGTGGCTATCGC
CAGCCACGATGGCGGCAAGCAAGCGCTCGAAACGGTGCAGCGGCTGTTGC
CGGTGCTGTGCCAGGACCATGGCCTGACCCCGGACCAAGTGGTGGCTATC
GCCAGCAACGGTGGCGGCAAGCAAGCGCTCGAAACGGTGCAGCGGCTGTT
GCCGGTGCTGTGCCAGGACCATGGCCTGACCCCGGACCAAGTGGTGGCTA
TCGCCAGCAACAATGGCGGCAAGCAAGCGCTCGAAACGGTGCAGCGGCTG
TTGCCGGTGCTGTGCCAGGACCATGGCCTGACTCCGGACCAAGTGGTGGC
TATCGCCAGCCACGATGGCGGCAAGCAAGCGCTCGAAACGGTGCAGCGGC
TGTTGCCGGTGCTGTGCCAGGACCATGGCCTGACCCCGGACCAAGTGGTG
GCTATCGCCAGCAACAATGGCGGCAAGCAAGCGCTCGAAACGGTGCAGCG
GCTGTTGCCGGTGCTGTGCCAGGACCATGGCCTGACCCCGGACCAAGT
GGTGGCTATCGCCAGCCACGATGGCGGCAAGCAAGCGCTCGAAACGGTGC
AGCGGCTGTTGCCGGTGCTGTGCCAGGACCATGGCCTGACTCCGGACCAA
GTGGTGGCTATCGCCAGCAACGATGGCGGCAAGCAAGCGCTCGAAACGGT
GCAGCGGCTGTTGCCGGTGCTGTGCCAGGACCATGGCCTGACTCCGGACC
AAGTGGTGGCCATCGCCAGCCACGATGGCGGCAAGCAAGCGCTCGAAACG
GTGCAGCGGCTGTTGCCGGTGCTGTGCCAGGACCATGGCCTGACCCCCGA
CCAAGTGGTGGCTATCGCCAGCAACATGGCGGCAAGCAAGCGCTCGAAA
CGGTGCAGCGGCTGTTGCCGGTGCTGTGCCAGGACCATGGCCTGACCCCG
GACCAAGTGGTGGCTATCGCCAGCAACGGTGGCGGCAAGCAAGCGCTCGA
AAGCATTGTGGCCCAGCTGAGCCGGCCTGATCCGGCGTTGGCCGCGTTGA
```

-continued

```
CCAACGACCACCTCGTCGCCTTGGCCTGCCTCGGCGGACGTCCTGCCATG
GATGCAGTGAAAAAGGGATTGCCGCACGCGCCGGAATTGATCAGAAGAGT
CAATCGCCGTATTGGCGAACGCACGTCCCATCGCGTTGCCGGATCCCAGC
TGGTGAAGTCCGAGCTGGAAGAAAAAAGAGCGAGCTGCGCCACAAGCTC
AAGTACGTGCCCCACGAGTACATCGAGCTGATCGAGATCGCCCGCAACAG
CACCCAAGACGCATCCTGGAGATGAAAGTGATGGAGTTCTTCATGAAGG
TGTACGGCTACCGCGGCAAGCACCTGGGCGGCTCCCGCAAGCCCGATGGC
GCCATCTACACCGTGGGCTCCCCCATCGACTATGGCGTCATTGTCGACAC
CAAGGCCTACTCCGGCGGCTACAACTTACCCATCGGTCAGGCCGACGAGA
TGCAACGCTACGTGAAGGAGAACCAGACCCGCAATAAGCACATTAATCCC
AACGAGTGGTGGAAGGTGTACCCCTCCTCCGTGACCGAGTTCAAATTCCT
GTTCGTGTCCGGCCACTTCAAGGGCAATTATAAGGCCCAACTGACCCGCC
TGAACCACAAGACCAACTGCAACGGCGCCGTGCTGTCCGTGGAGGAACTG
CTGATCGGCGGCGAGATGATCAAGGCTGGTACCCTGACCCTGGAAGAGGT
GCGCCGCAAGTTCAACAATGGTGAAATCAATTTCAGGTCCGGCGGCGGAG
AGGGCAGAGGAAGTCTTCTAACATGCGGTGACGTGGAGGAGAATCCCGGC
CCTAGGATGGACTACAAAGACCATGACGGTGATTATAAAGATCATGCAT
CGATTACAAGGATGACGATGACAAGATGGCCCCCAAGAAGAAGAGGAGG
TGGGCATTCACGGGGTGCCGGCTAGCATGGTGGATCTACGCACGCTCGGC
TACAGTCAGCAGCAGCAAGAGAAGATCAAACCGAAGGTGCGTTCGACAGT
GGCGCAGCACCACGAGGCACTGGTGGGCCATGGGTTTACACACGCGCACA
TCGTTGCGCTCAGCCAACACCCGGCAGCGTTAGGGACCGTCGCTGTCACG
TATCAGCACATAATCACGGCGTTGCCAGAGGCGACACGAAGACATCGT
TGGCGTCGGCAAACAGTGGTCCGGCGCACGCGCCCTGGAGGCCTTGCTCA
CGGATGCGGGGAGTTGAGAGGTCCGCCGTTACAGTTGGACACAGGCCAA
CTTGTGAAGATTGCAAAACGTGGCGGCGTGACCGCAATGGAGGCAGTGCA
TGCATCGCGCAATGCACTGACAGGTGCCCCCCTGAACCTGACCCCGGACC
AAGTGGTGGCTATCGCCAGCAACAAGGGCGGCAAGCAAGCGCTCGAAACG
GTGCAGCGGCTGTTGCCGGTGCTGTGCCAGGACCATGGCCTGACCCCGGA
CCAAGTGGTGGCTATCGCCAGCAACAAGGGCGGCAAGCAAGCGCTCGAAA
CGGTGCAGCGGCTGTTGCCGGTGCTGTGCCAGGACCATGGCCTGACCCCG
GACCAAGTGGTGGCTATCGCCAGCAACAAGGGCGGCAAGCAAGCGCTCGA
AACGGTGCAGCGGCTGTTGCCGGTGCTGTGCCAGGACCATGGCCTGACCC
CGGACCAAGTGGTGGCTATCGCCAGCAACATTGGCGGCAAGCAAGCGCTC
GAAACGGTGCAGCGGCTGTTGCCGGTGCTGTGCCAGGACCATGGCCTGAC
CCCGGACCAAGTGGTGGCTATCGCCAGCAACAAGGGCGGCAAGCAAGCGC
TCGAAACGGTGCAGCGGCTGTTGCCGGTGCTGTGCCAGGACCATGGCCTG
ACCCCGGACCAAGTGGTGGCTATCGCCAGCAACATTGGCGGCAAGCAAGC
GCTCGAAACGGTGCAGCGGCTGTTGCCGGTGCTGTGCCAGGACCATGGCC
TGACCCCGGACCAAGTGGTGGCTATCGCCAGCAACGGTGGCGGCAAGCAA
GCGCTCGAAACGGTGCAGCGGCTGTTGCCGGTGCTGTGCCAGGACCATGG
CCTGACCCCGGACCAAGTGGTGGCTATCGCCAGCAACAAGGGCGGCAAGC
AAGCGCTCGAAACGGTGCAGCGGCTGTTGCCGGTGCTGTGCCAGGACCAT
GGCCTGACTCCGGACCAAGTGGTGGCTATCGCCAGCCACGATGGCGGCAA
GCAAGCGCTCGAAACGGTGCAGCGGCTGTTGCCGGTGCTGTGCCAGGACC
ATGGCCTGACCCCGGACCAAGTGGTGGCTATCGCCAGCAACATTGGCCGG
AAGCAAGCGCTCGAAACGGTGCAGCGGCTGTTGCCGGTGCTGTGCCAGGA
CCATGGCCTGACCCCGGACCAAGTGGTGGCTATCGCCAGCAACGGTGGCG
GCAAGCAAGCGCTCGAAACGGTGCAGCGGCTGTTGCCGGTGCTGTGCCAG
GACCATGGCCTGACCCCGGACCAAGTGGTGGCTATCGCCAGCAACATTGG
CGGCAAGCAAGCGCTCGAAACGGTGCAGCGGCTGTTGCCGGTGCTGTGCC
AGGACCATGGCCTGACCCCGGACCAAGTGGTGGCTATCGCCAGCAACGGT
GGCGGCAAGCAAGCGCTCGAAACGGTGCAGCGGCTGTTGCCGGTGCTGTG
CCAGGACCATGGCCTGACTCCGGACCAAGTGGTGGCTATCGCCAGCCACG
ATGGCGGCAAGCAAGCGCTCGAAACGGTGCAGCGGCTGTTGCCGGTGCTG
TGCCAGGACCATGGCCTGACTCCGGACCAAGTGGTGGCTATCGCCAGCCA
CGATGGCGGCAAGCAAGCGCTCGAAACGGTGCAGCGGCTGTTGCCGGTGC
TGTGCCAGGACCATGGCCTGACCCCGGACCAAGTGGTGGCTATCGCCA
GCAACAAGGGCGGCAAGCAAGCGCTCGAAAGCATTGTGGCCCAGCTGAGC
CGGCCTGATCCGGCGTTGGCCGCGTTGACCAACGACCACCTCGTCGCCTT
GGCCTGCCTCGGCGGACGTCCTGCCATGGATGCAGTGAAAAAGGGATTGC
CGCACGCGCCGGAATTGATCAGAAGAGTCAATCGCCGTATTGGCGAACGC
ACGTCCCATCGCGTTGCCAGATCTCAACTAGTCAAAAGTGAACTGGAGGA
GAAGAAATCTGAACTTCGTCATAAATTGAAATATGTGCCTCATGAATATA
TTGAATTAATTGAAATTGCCAGAAATTCCACTCAGGATAGAATTCTTGAA
ATGAAGGTAATGGAATTTTTTATGAAAGTTTATGGATATAGAGGTAAACA
TTTGGGTGGATCAAGGAAACCGGACGGAGCAATTTATACTGTCGGATCTC
CTATTGATTACGGTGTGATCGTGGATACTAAAGCTTATAGCGGAGGTTAT
AATCTGCCAATTGGCCAAGCAGATGAAATGGAGCGATATGTCGAAGAAAA
TCAAACAGAAAAACATCTCAACCCTAATGAATGGTGGAAAGTCTATC
CATCTTCTGTAACGGAATTTAAGTTTTTATTTGTGAGTGGTCACTTTAAA
GGAAACTACAAAGCTCAGCTTACACGATTAAATCATATCACTAATTGTAA
TGGAGCTGTTCTTAGTGTAGAAGAGCTTTTAATTGGTGGAGAAATGATTA
AAGCGGCACATTAACCTTAGAGGAAGTGAGACGGAAATTTAATAACGGC
GAGATAAACTTTTAATAG
```

The amino acid sequence of the TALENs. T2A motif site is indicated as underlined and bold.

SEQ ID NO. 12

```
MVDLRTLGYSQQQQEKIKPKVRSTVAQHHEALVGHGFTHAHIVALSQHPA
ALGTVAVTYQHIITALPEATHEDIVGVGKQWSGARALEALLTDAGELRGP
PLQLDTGQLVKIAKRGGVTAMEAVHASRNALTGAPLNLTPDQVVAIASHD
GGKQALETVQRLLPVLCQDHGLTPDQVVAIASNNGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASNNGGKQALETVQRLLP
VLCQDHGLTPDQVVAIASHDGGKQALETVQRLLPVLCQDHGLTPDQVVAI
ASNGGGKQALETVQRLLPVLCQDHGLTPDQVVAIASNNGGKQALETVQRL
LPVLCQDHGLTPDQVVAIASHDGGKQALETVQRLLPVLCQDHGLTPDQVV
AIASNGGGKQALETVQRLLPVLCQDHGLTPDQVVAIASHDGGKQALETVQ
RLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALET
VQRLLPVLCQDHGLTPDQVVAIASNNGGKQALETVQRLLPVLCQDHGLTP
DQVVAIASNGGGKQALESIVAQLSRPDPALAALTNDHLVALACLGGRPAM
DAVKKGLPHAPELIRRVNRRIGERTSHRVAGSQLVKSELEEKKSELRHKL
KYVPHEYIELIEIARNSTQDRILEMKVMEFFMKVYGYRGKHLGGSRKPDG
AIYTVGSPIDYGVIVDTKAYSGGYNLPIGQADEMQRYVKENQTRNKHINP
NEWWKVYPSSVTEFKFLFVSGHFKGNYKAQLTRLNHKTNCNGAVLSVEEL
LIGGEMIKAGTLTLEEVRRKFNNGEINFRSGGGEGRGSLLTCGDVENPG
PRMDYKDHDGDYKDHDIDYKDDDDKMAPKKKRKVGIHGVPASMVDLRTLG
YSQQQQEKIKPKVRSTVAQHHEALVGHGFTHAHIVALSQHPAALGTVAVT
YQHIITALPEATHEDIVGVGKQWSGARALEALLTDAGELRGPPLQLDTGQ
LVKIAKRGGVTAMEAVHASRNALTGAPLNLTPDQVVAIASNKGGKQALET
VQRLLPVLCQDHGLTPDQVVAIASNKGGKQALETVQRLLPVLCQDHGLTP
DQVVAIASNKGGKQALETVQRLLPVLCQDHGLTPDQVVAIASNIGGKQAL
ETVQRLLPVLCQDHGLTPDQVVAIASNKGGKQALETVQRLLPVLCQDHGL
TPDQVVAIASNIGGKQALETVQRLLPVLCQDHGLTPDQVVAIASNGGGKQ
ALETVQRLLPVLCQDHGLTPDQVVAIASNKGGKQALETVQRLLPVLCQDH
GLTPDQVVAIASHDGGKQALETVQRLLPVLCQDHGLTPDQVVAIASNIGG
KQALETVQRLLPVLCQDHGLTPDQVVAIASNGGGKQALETVQRLLPVLCQ
DHGLTPDQVVAIASNIGGKQALETVQRLLPVLCQDHGLTPDQVVAIASNG
GGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIAS
HDGGKQALETVQRLLPVLCQDHGLTPDQVVAIASNKGGKQALESIVAQLS
RPDPALAALTNDHLVALACLGGRPAMDAVKKGLPHAPELIRRVNRRIGER
TSHRVARSQLVKSELEEKKSELRHKLKYVPHEYIELIEIARNSTQDRILE
MKVMEFFMKVYGYRGKHLGGSRKPDGAIYTVGSPIDYGVIVDTKAYSGGY
NLPIGQADEMERYVEENQTRNKHLNPNEWWKVYPSSVTEFKFLFVSGHFK
GNYKAQLTRLNHITNCNGAVLSVEELLIGGEMIKAGTLTLEEVRRKFNNG
EINF
```

The coding sequences of mutant tamlo-aabbdd. Tamlo-a. Delete 32bp in target site. Deletion sequence is indicated with dots

SEQ ID NO. 39

```
ATGGCGGAGGACGACGGGTACCCCCCGGCGCGGACGCTGCCGGAGACGCC
GTCCTGGGCGGTGGCGCTGGTCTTCGCCGTCATGATCATCGTCTCCGTCC
TCCTGGGACACGCGCTCCACAAGCTCGGCCAGTGGTTCCACAAGCGCAC
AAGAACGCGCTGGCCGAGGCGCTGGAGAAGATGAAGGCGGAGCTGATGCT
GGTGGGATT................CAATCTCCG
GGATATGCATCTCCCAGAAGGCCGCCAGCATCATGCGCCCCTGCAAGGTG
GAACCCGGTTCCGTCAAGAGCAAGTACAAGGACTACTACTGCGCCAAAGA
GGGCAAGGTGGCGCTCATGTCCACGGGCAGCCTGCACCAGCTCCACATAT
TCATCTTCGTGCTAGCCGTCTTCCATGTCACCTACAGCGTCATCATCATG
GCTCTAAGCCGTCTCAAGATGAGAACATGGAAGAAATGGGAGACAGAGAC
CGCCTCCTTGGAATACCAGTTCGCAAATGATCCTGCGCGGTTCCGCTTCA
CGCACCAGACGTCGTTCGTGAAGCGGCACCTGGGCCTGCCTCCAGCACCCCC
GGCGTCAGATGGGTGGTGGCCTTCTTCAGGCAGTTCTTCAGGTCGGTCAC
CAAGGTGGACTACCTCACCTTGAGGGCAGGCTTCATCAACGCGCACTTGT
CGCAGAACAGCAAGTTCGACTTCCACAAGTACATCAAGAGGTCCATGGAG
GACGACTTCAAAGTCGTCGTTGGCATCAGCCTCCCGTGTGGGCTGTGGC
GATCTTCACCCTCTTCCTTGATATCGACGGGATCGGCACACTCACCTGGG
TTTCTTTCATCCCTCTCATCATCCTCTTGTGTGTTGGAACCAAGCTAGAG
ATGATCATCATGGAGATGGCCCTGGAGATCCAGGACCGGTCGAGCGTCAT
CAAGGGGCACCCGTGGTCGAGCCCAGCAACAAGTTCTTCTGGTTCCACC
GCCCCGACTGGGTCCTCTTCTTCATACACCTGACGCTGTTCCAGAACGCG
TTTCAGATGGCACATTTCGTGTGGACAGTGGCCACGCCCGGCTTGAAGGA
CTGCTTCCATATGAACATCGGGCTGAGCATCATGAAGGTCGTGCTGGGGC
TGGCTCTCCAGTTCCTGTGCAGCTACATCACCTTCCCCCTCTACGCGCTA
GTCACACAGATGGGATCAAACATGAAGAGGTCCATCTTCGACGAGCAGAC
AGCCAAGGCGCTGACCAACTGGCGGAACACGGCCAAGGAGAAGAAGAAGG
TCCGAGACACGGACATGCTGATGGCGCAGATGATCGGCGACGCAACACCC
AGCCAGGCGACGTCCCCGATCGCTAGCCGGGCTCATCGCCGGTGCACCT
GCTTCAGAAGGGCATGGGACGGTCTGACGATCCCCAGACGCACCGACCT
CGCCAAGGACCATGAGGAGGCTAGGGACATGTACCCGGTTGTGGTGGCG
CATCCTGTACACAGACTAAATCCTGCTGACAGGAGAAGGTCGGTCTCTTC
ATCAGCCCTCGATGCCGACATCCCCAGCGCAGATTTTTCCTTCAGCCAGG
GATGA
``` tamlo-b. Insert 141 bp in target site. Insertion
sequence is labelled in bold.

SEQ ID NO. 40

ATGGCGGAGGACGACGGGTACCCCCCAGCGAGGACGCTGCCGGAGACGCC
GTCCTGGGCGGTGGCCCTCGTCTTCGCCGTCATGATCATCGTGTCCGTCC
TCCTGGAGCACGCGCTCCATAAGCTCGGCCAGTGGTTCCACAAGCGGCAC
AAGAACGCGCTGGCGGAGGCGCTGGAGAAGATCAAGGCGGAGCTCATGCT
GGTGGGCTTCATCTCGCTGCTGCTCGCCGTGACGCAGGA**CGAGGCACTGG
TGGGCCATGGGTTTACACACGGCACATCGTTGCGCTCAGCCAACACCCG
GCAGCGTTAGGGACCGTCGCTGTCACGTATCAGCACATAATCACGGCGTT
GCCAGAGGCGACACACGAAGACATCGTTGG**CCCCATCTCCGGGATATGCA
TCTCCGAGAAGGCCGCCAGCATCATGCGGCCCTGCAAGCTGCCCCCTGGC
TCCGTCAAGAGCAAGTACAAAGACTACTACTGCGCCAAACAGGGCAAGGT
GTCGCTCATGTCCACGGGCAGCTTGCACCAGCTGCACATATTCATCTTCG
TGCTCGCCGTCTTCCATGTCACCTACAGCGTCATCATCATGGCTCTAAGC
CGTCTCAAGATGAGAACCTGGAAGAAATGGGAGACAGAGACCGCCTCCCT
GGAATACCAGTTCGCAAATGATCCTGCCGGTTCCGCTTCACGCACCAGA
CGTCGTTCGTGAAGCGGCACCTGGGCCTCTCCAGCACCCCCGGCGTCAGA
TGGGTGGTGGCCTTCTTCAGGCAGTTCTTCAGGTCGGTCACCAAGGTGGA
CTACCTCACCTTGAGGGCAGGCTTCATCAACGCGCATTTGTCGCATAACA
GCAAGTTCGACTTCCACAAGTACATCAAGAGGTCCATGGACGACTTC
AAAGTCGTCGTTGGCATCAGCCTCCCGCTGTGGIGTGGCGATCCTCAC
CCTCTTCCTTGACATTGACGGGATCGGCACGCTCACCTGGATTTCTTTCA
TCCCTCTCGTCATCCTCTTGTGTGTTGGAACCAAGCTGGAGATGATCATC
ATGGAGATGGCCTGGAGATCCAGGACCGGGCGAGCGTCATCAAGGGGGC
GCCCGTGGTTGAGCCCAGCAACAAGTTCTTCTGGTTCCACCGCCCCGACT
GGGTCCTCTTCTTCATACACCTGACGCTATTCCAGAACGCGTTTCAGATG
GCACATTTCGTGTGGACAGTGGCCACGCCCGGCTTGAAGAAATGCTTCCA
TATGCACATCGGGCTGAGCATCATGAAGGTCGTGCTGGGGCTGGCTCTTC
AGTTCCTCTGCAGCTATATCACCTTCCCGCTCTACGCGCTCGTCACACAG
ATGGGATCAAACATGAAGAGGTCCATCTTCGACGAGCAGACGGCCAAGGC
GCTGACAAACTGGCGGAACACGGCCAAGGAGAAGAAGAAGGTCCGAGACA
CGGACATGCTGATGGCGCAGATGATCGGCGACGCGACCAGCCAGCCGAGGG
GCGTCGCCCATGCCTAGCCGGGGCTCGTCGCCAGTGCACCTGCTTCACAA
GGGCATGGGACGGTCCGACGATCCCCAGAGCACGCCAACCTCGCCAAGGG
CCATGGAGGAGGCTAGGGACATGTACCCGGTTGTGGTGGCGCATCCAGTG
CACAGACTAAATCCTGCTGACAGGAGAAGGTCGGTCTCGTCGTCGGCACT
CGATGTCGACATTCCCAGCGCAGATTTTTCCTTCAGCCAGGGATGA tamlo-d. Delete 11 bp and insert 81 bp in target
site. Insertion sequence is labelled in bold.

SEQ ID NO. 41

ATGGCGGAGGACGACGGGTACCCCCCGGCGCGGACGCTGCCGGAGACGCC
GTCCTGGGCGGTGGCGCTCGTCTTCGCCGTCATGATCATCGTGTCCGTCC
TCCTGGAGCACGCGCTCCACAAGCTCGGCCAGTGGTTCCACAAGCGGCAC
AAGAACGCGCTGGCGGAGGCGCTGGAGAAGATCAAAGCGGAGCTGATGCT
GGTGGGGTTCATCTCGCTGCTGCTCGCCGTGACGCAGG**AGATGCATATCC
CGGAGATGGCTAAACTAACTATGCGTGACGGCGAGCAGCAGGAGATGCAT
ATCCCGGAGATGGCTAAACT**GGATATGCATCTCCGAGAAGGCCGCCAGCA
TCATGCGGCCCTGCAGCCTGCCCCCTGGTTCCGTCAAGAGCAAGTACAAA
GACTACTACTGCGCCAAAAAGGGCAAGGTGTCGCTAATGTCCACGGGCAG
CTTGCACCAGCTCCACATATTCATCTTCGTGCTCGCCGTCTTCCATGTCA
CCTACAGCGTCATCATCATGGCTCTAAGCCGTCTCAAGATGAGGACATGG
AAGAAATGGGAGACAGAGACCGCCTCCTTGGAATACCAGTTCGCAAATGA
TCCTGCGCGGTTCCGCTTCACGCACCAGACGTCGTTCGTGAAGCGTCACC
TGGGCCTCTCCAGCACCCCCGGCATCAGATGGGTGGTGGCCTTCTTCAGG
CAGTTCTTCAGGTCGGTCACCAAGGTGGACTACCTCACCCTGAGGGCAGG
CTTCATCAACGCGCATTTGTCGCATAACAGCAAGTTCGACTTCCACAAGT
ACATCAAGAGGTCCATGGAGGACGACTTCAAAGTCGTCGTTGGCATCAGC
CTCCCGCTGTGGTGTGGCGATCCTCACCCTCTTCCTTGATATTGACGG
GATCGGCACGCTCACCTGGATTTCTTTCATCCCTCTCGTCATCCTCTTGT
GTGTTGGAACCAAGCTGGAGATGATCATCATGGAGATGGCCCTGGAGATC
CAGGACCGGGCGAGCGTCATCAAGGGGGCGCCCGTGGTTGAGCCCAGCAA
CAAGTTCTTCTGGTTCCACCGCCCCGACTGGGTCCTCTTCTTCATACACC
TGACGCTGTTCCAGAATGCGTTTCAGATGGCACATTTCGTCTGGACAGTG
GCCACGCCCGGCTTGAAGAAATGCTTCCATATGCACATCGGGCTGAGCAT
CATGAAGGTCGTGCTGGGGCTGGCTCTTCAGTTCCTCTGCAGCTATATCA
CCTTCCCGCTCTACGCGCTCGTCACACAGATGGGATCAAACATGAAGAGG
TCCATCTTCGACGAGCAGACGGCCAAGGCGCTGACAAACTGGCGGAACAC
GGCCAAGGAGAAGAAGAAGGTCCGAGACACGGACATGCTGATGGCGCAGA
TGATCGGCGACGCGACGCCCAGCCGAGGGCGTCGCCCATGCCTAGCCGG
GGCTCGTCGCCAGTGCACCTGCTTCACAAGGGCATGGGTTCCGACGA
TCCCCAGAGCACGCCAACCTCGCCAAGGGCCATGGAGGAGGCTAGGGACA
TGTACCCGGTTGTGGTGGCGCATCCAGTGCACAGACTAAATCCTGCTGAC
AGGAGAAGGTCGGTCTCTTCGTCGGCACTCGATGCCGACATCCCCAGCGC
AGATTTTTCCTTCAGCCAGGGATGA

The invention claimed is:

1. A mutant wheat plant or plant part comprising a loss of function mutation in a TaMLO-A1, TaMLO-B1 and a TaMLO-D1 nucleic acid sequence, wherein said mutation has been introduced into SEQ NO. 13, SEQ ID NO. 14, SEQ ID NO. 15, SEQ ID NO. 16 or SEQ ID NO. 17 by using targeted genome modification, and wherein said mutation confers resistance to powdery mildew.

2. A mutant wheat plant or plant part according to claim 1 wherein said mutation has been introduced using zinc finger nucleases (ZFNs), transcription activator-like effector nucleases (TALENs), or clustered regularly interspaced short palindromic repeats (CRISPR)/Cas9.

3. A mutant wheat plant according to claim 1 wherein the wild type nucleic acid sequence of TaMLO-A1 comprises SEQ ID NO. 1, or a nucleic acid sequence encoding SEQ ID NO: 4, wherein the wild type TaMLO-B1 nucleic acid sequence comprises SEQ ID NO: 2 or a nucleic acid sequence encoding SEQ ID NO: 5, and wherein the wild type TaMLO-D1 nucleic acid sequence comprises SEQ ID NO: 3 or a nucleic acid sequence encoding SEQ ID NO: 6, or wherein said wild type sequence of TaMLO-A1, TaMLO-B1, or TaMLO-D1 is at least 95% identical to SEQ ID NO: 1, 2, or 3, respectively.

4. A mutant wheat plant or plant part according to claim 1, wherein said mutation is insertion, deletion or substitution.

5. A mutant wheat plant or plant part according to claim 1 wherein said wheat plant is selected from the group consisting of, Triticum aestivum, T. aethiopicum, T. araraticum, T. boeoticum, T. carthlicum, T. compactum, T. dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii and T. zhukovskyi.

6. A mutant wheat plant or plant part wherein a representative sample of seed of said wheat plant is deposited under CGMCC Accession Number 9322, comprising a loss of function mutation in a said TaMLO-A1, TaMLO-B1 and a TaMLO-D1 nucleic acid sequence wherein said mutation confers resistance to powdery mildew.

7. The mutant wheat plant of claim 1, where said plant comprises tamlo-a nucleic acid sequence comprising SED ID NO. 39; tamlo-b1 nucleic acid sequence comprising SED ID NO. 40, and tamlo-d1 nucleic acid sequence comprising SED ID NO. 41.

8. A plant or plant part produced by crossing a mutant wheat plant according to claim 1 with a second plant, wherein said plant or plant part produced comprises said loss of function mutation.

9. A plant part according to claim 8 wherein said plant part is a seed.

10. A primer pair selected from the group consisting of SEQ ID Nos: 42 and 43, SEQ ID Nos. 44 and 45 and SEQ ID Nos: 46 and 47.

11. A method of determining the presence of a mutant TaMLO-A1, TaMLO-B1, and/or TaMLO-D1 nucleic acid in a wheat plant comprising assaying said wheat plant by amplifying the nucleic acid with the primers of claim 10.

12. A method for producing a mutant wheat plant resistant to powdery mildew (Pm) comprising introducing a loss of function mutation into a TaMLO-A1, TaMLO-B1 and a TaMLO-D1 nucleic acid sequence in a wheat plant using targeted genome modification within SEQ ID NO: 13, 14, 15, 16 or 17.

13. A method according to claim 12 wherein said mutation is introduced using zinc finger nucleases (ZFNs), transcription activator-like effector nucleases (TALENs), or clustered regularly interspaced short palindromic repeats (CRISPR)/Cas9.

14. A method according to claim 12 comprising introducing an expression vector comprising a TALEN into a wheat plant and screening for the induced loss of function mutation within SEQ ID NO: 13, 14, 15, 16 or 17 of TaMLO-A1, TaMLO-B1 and TaMLO-D1 genes.

15. A method according to claim 12 comprising introducing and co-expressing in a wheat plant Cas9 and sgRNA targeted to TaMLO-A1, TaMLO-B1 and/or TaMLO-D1 and screening for the induced loss of function mutation within SEQ ID NO: 13, 14, 15, or 16 of TaMLO-A1, TaMLO-B1 and TaMLO-D1 genes.

16. A method according to claim 12 further comprising screening for the induced loss of function mutation within SEQ ID NO: 13, 14, 15, 16 or 17 of TaMLO-A1, TaMLO-B1 and TaMLO-D1 genes by obtaining a nucleic acid sample from a transformed plant and carrying out nucleic acid amplification and optionally restriction enzyme digestion to detect the mutation in TaMLO-A1, TaMLO-B1 and TaMLO-D1.

17. A method according to claim 16 wherein said nucleic acid amplification comprises primer selected from SED ID NOs. 18 to 25 or 42 to 47.

18. A method according to claim 16 comprising assessing PCR fragments amplified from the transformed plants using a gel electrophoresis based assay.

19. A method according to claim 12 comprising confirming the presence of the mutation by sequencing the TaMLO-A1, TaMLO-B1 and/or TaMLO-D1 nucleic acid.

20. A method according to claim 12 comprising producing a population of plants and selecting or choosing at least one plant resistant to powdery mildew (Pm), wherein the at least one plant comprises the loss of function mutation within SEQ ID NO: 13, 14, 15, 16 or 17 of TaMLO-A1, TaMLO-B1 and TaMLO-D1 genes.

21. A detection kit for determining the presence of a mutant TaMLO-A1, TaMLO-B1, and/or TaMLO-D1 nucleic acid or polypeptide in a wheat plant, comprising a polymerase and a primer pair, wherein said primer pair is selected from the group consisting of SEQ ID NOs: 42 and 43, SEQ ID Nos: 44 and 45, and SEQ ID Nos: 46 and 47.

22. A vector comprising a nucleic acid sequence comprising SEQ ID No: 11 or encoding a polypeptide comprising SEQ ID NO: 12.

23. The mutant wheat plant or plant part of claim 1, wherein said plant or plant part is homozygous for each of said loss of function mutation in said TaMLO-A1, TaMLO-B1 and TaMLO-D1 nucleic acid sequence.

24. A plant part of claim 1, wherein said plant part is seed, wherein the seed comprises the loss of function mutation in SEQ ID NO: 13, 14, 15, 16 or 17 of TaMLO-A1, TaMLO-B1 and TaMLO-D1 genes.

25. A plant or plant part produced by crossing said plant of claim 8 with a third plant, wherein said plant or plant part produced comprises said loss of function mutation.

26. The method of claim 14, wherein said vector comprises a pair of TALENs targeting nucleic acid sequence conserved between said TaMLO-A1, TaMLO-B1 and a TaMLO-D1 nucleic acid sequences.

27. The method of claim 14, wherein said TALEN comprises SEQ ID NO: 11 or encodes SEQ ID NO: 12.

* * * * *

SEQUENCE LISTING

<160> NUMBER OF SEQ ID NOS: 189

<210> SEQ ID NO 1
<211> LENGTH: 1605
<212> TYPE: DNA
<213> ORGANISM: Triticum aestivum

<400> SEQUENCE: 1

| atggcggagg | acgacgggta | cccccggcg | cggacgctgc | cggagacgcc | gtcctgggcg | 60 |
| gtggcgctgg | tcttcgccgt | catgatcatc | gtctccgtcc | tcctggagca | cgcgctccac | 120 |
| aagctcggcc | agtggttcca | caagcggcac | aagaacgcg | tggcggaggc | gctggagaag | 180 |
| atgaaggcgg | agctgatgct | ggtgggattc | atctcgctgc | tgctcgccgt | cacgcaggac | 240 |
| ccaatctccg | gatatgcat | ctcccagaag | gccgccagca | tcatgcgccc | tgcaaggtg | 300 |
| gaacccggtt | ccgtcaagag | caagtacaag | gactactact | gcgccaaaga | gggcaaggtg | 360 |
| gcgctcatgt | ccacgggcag | cctgcaccag | ctccacatat | tcatcttcgt | gctagccgtc | 420 |
| ttccatgtca | cctacagcgt | catcatcatg | gctctaagcc | gtctcaagat | gagaacatgg | 480 |
| aagaaatggg | agacagagac | cgcctccttg | gaataccagt | tcgcaaatga | tcctgcgcgg | 540 |
| ttccgcttca | cgcaccagac | gtcgttcgtg | aagcggcacc | tgggcctgtc | cagcaccccc | 600 |
| ggcgtcagat | gggtggtggc | cttcttcagg | cagttcttca | ggtcggtcac | caaggtggac | 660 |
| tacctcaccc | tgagggcagg | cttcatcaac | gcgcacttgt | cgcagaacag | caagttcgac | 720 |
| ttccacaagt | acatcaagag | gtccatggag | gacgacttca | aagtcgtcgt | tggcatcagc | 780 |

```
ctcccgctgt gggctgtggc gatcctcacc ctcttccttg atatcgacgg gatcggcaca    840
ctcacctggg tttctttcat ccctctcatc atcctcttgt gtgttggaac caagctagag    900
atgatcatca tggagatggc cctggagatc caggaccggt cgagcgtcat caaggggca     960
cccgtggtcg agcccagcaa caagttcttc tggttccacc gccccgactg ggtcctcttc   1020
ttcatacacc tgacgctgtt ccagaacgcg tttcagatgg cacatttcgt gtggacagtg   1080
gccacgcccg gcttgaagga ctgcttccat atgaacatcg gctgagcat catgaaggtc    1140
gtgctggggc tggctctcca gttcctgtgc agctacatca ccttccccct ctacgcgcta   1200
gtcacacaga tgggatcaaa catgaagagg tccatcttcg acgagcagac agccaaggcg   1260
ctgaccaact ggcggaacac ggccaaggag aagaagaagg tccgagacac ggacatgctg   1320
atggcgcaga tgatcggcga cgcaacaccc agccgaggca cgtccccgat gcctagccgg   1380
ggctcatcgc cggtgcacct gcttcagaag ggcatgggac ggtctgacga tccccagagc   1440
gcaccgacct cgccaaggac catggaggag gctagggaca tgtacccggt tgtggtggcg   1500
catcctgtac acagactaaa tcctgctgac aggagaaggt cggtctcttc atcagccctc   1560
gatgccgaca tccccagcgc agattttttcc ttcagccagg gatga                   1605

<210> SEQ ID NO 2
<211> LENGTH: 1605
<212> TYPE: DNA
<213> ORGANISM: Triticum aestivum

<400> SEQUENCE: 2
atggcggagg acgacgggta ccccccagcg aggacgctgc cggagacgcc gtcctgggcg     60
gtggccctcg tcttcgccgt catgatcatc gtgtccgtcc tcctggagca cgcgctccat    120
aagctcggcc agtggttcca caagcggcac aagaacgcgc tggcggaggc gctggagaag    180
atcaaggcgg agctcatgct ggtgggcttc atctcgctgc tgctcgccgt gacgcaggac    240
cccatctccg ggatatgcat ctccgagaag gccgccagca tcatgcggcc ctgcaagctg    300
cccccctggct ccgtcaagag caagtacaaa gactactact gcgccaaaca gggcaaggtg    360
tcgctcatgt ccacgggcag cttgcaccag ctgcacatat tcatcttcgt gctcgccgtc    420
ttccatgtca cctacagcgt catcatcatg gctctaagcc gtctcaagat gagaacctgg    480
aagaaatggg agacagagac cgcctccctg gaataccagt tcgcaaatga tcctgcgcgg    540
ttccgcttca cgcaccagac gtcgttcgtg aagcggcacc tgggcctctc cagcaccccc    600
ggcgtcagat gggtggtggc cttcttcagg cagttcttca ggtcggtcac caaggtggac    660
tacctcacct tgagggcagg cttcatcaac gcgcatttgt cgcataacag caagttcgac    720
ttccacaagt acatcaagag gtccatggag gacgacttca agtcgtcgt tggcatcagc     780
ctcccgctgt ggtgtgtggc gatcctcacc ctcttccttg acattgacgg gatcggcacg    840
ctcacctgga tttctttcat ccctctcgtc atcctcttgt gtgttggaac caagctggag   900
atgatcatca tggagatggc cctggagatc caggaccggg cgagcgtcat caaggggcg    960
cccgtggttg agcccagcaa caagttcttc tggttccacc gccccgactg ggtcctcttc   1020
ttcatacacc tgacgctatt ccagaacgcg tttcagatgg cacatttcgt gtggacagtg   1080
gccacgcccg gcttgaagaa atgcttccat atgcacatcg gctgagcat catgaaggtc    1140
gtgctggggc tggctcttca gttcctctgc agctatatca ccttcccgct ctacgcgctc   1200
gtcacacaga tgggatcaaa catgaagagg tccatcttcg acgagcagac ggccaaggcg   1260
ctgacaaaact ggcggaacac ggccaaggag aagaagaagg tccgagacac ggacatgctg   1320
```

-continued

| atggcgcaga tgatcggcga cgcgacgccc agccgagggg cgtcgcccat gcctagccgg | 1380 |
| ggctcgtcgc cagtgcacct gcttcacaag ggcatgggac ggtccgacga tccccagagc | 1440 |
| acgccaacct cgccaagggc catggaggag gctagggaca tgtacccggt tgtggtggcg | 1500 |
| catccagtgc acagactaaa tcctgctgac aggagaaggt cggtctcgtc gtcggcactc | 1560 |
| gatgtcgaca ttcccagcgc agattttttcc ttcagccagg gatga | 1605 |

<210> SEQ ID NO 3
<211> LENGTH: 1605
<212> TYPE: DNA
<213> ORGANISM: Triticum aestivum

<400> SEQUENCE: 3

| atggcggagg acgacgggta cccccccggcg cggacgctgc cggagacgcc gtcctgggcg | 60 |
| gtggcgctcg tcttcgccgt catgatcatc gtgtccgtcc tcctggagca cgcgctccac | 120 |
| aagctcggcc agtggttcca caagcggcac aagaacgcgc tggcggaggc gctggagaag | 180 |
| atcaaagcgg agctgatgct ggtggggttc atctcgctgc tgctcgccgt gacgcaggac | 240 |
| ccaatctccg ggatatgcat ctccgagaag gccgccagca tcatgcggcc ctgcagcctg | 300 |
| cccccctggtt ccgtcaagag caagtacaaa gactactact gcgccaaaaa gggcaaggtg | 360 |
| tcgctaatgt ccacgggcag cttgcaccag ctccacatat tcatcttcgt gctcgccgtc | 420 |
| ttccatgtca cctacagcgt catcatcatg gctctaagcc gtctcaagat gaggacatgg | 480 |
| aagaaatggg agacagagac cgcctccttg aataccagt tcgcaaatga tcctgcgcgg | 540 |
| ttccgcttca cgcaccagac gtcgttcgtg aagcgtcacc tgggcctctc cagcaccccc | 600 |
| ggcatcagat gggtggtggc cttcttcagg cagttcttca ggtcggtcac caaggtggac | 660 |
| tacctcaccc tgagggcagg cttcatcaac gcgcatttgt cgcataacag caagttcgac | 720 |
| ttccacaagt acatcaagag gtccatggag gacgacttca agtcgtcgt tggcatcagc | 780 |
| ctcccgctgt ggtgtgtggc gatcctcacc ctcttccttg atattgacgg gatcggcacg | 840 |
| ctcacctgga tttctttcat ccctctcgtc atcctcttgt gtgttggaac caagctggag | 900 |
| atgatcatca tggagatggc cctggagatc caggaccggg cgagcgtcat caaggggggcg | 960 |
| cccgtggttg agcccagcaa caagttcttc tggttccacc gccccgactg ggtcctcttc | 1020 |
| ttcatacacc tgacgctgtt ccagaatgcg tttcagatgg cacatttcgt ctggacagtg | 1080 |
| gccacgcccg gcttgaagaa atgcttccat atgcacatcg ggctgagcat catgaaggtc | 1140 |
| gtgctggggc tggctcttca gttcctctgc agctatatca ccttcccgct ctacgcgctc | 1200 |
| gtcacacaga tgggatcaaa catgaagagg tccatcttcg acgagcagac ggccaaggcg | 1260 |
| ctgacaaaact ggcggaacac ggccaaggag aagaagaagg tccgagacac ggacatgctg | 1320 |
| atggcgcaga tgatcggcga cgcgacgccc agccgagggg cgtcgcccat gcctagccgg | 1380 |
| ggctcgtcgc cagtgcacct gcttcacaag ggcatgggac ggtccgacga tccccagagc | 1440 |
| acgccaacct cgccaagggc catggaggag gctagggaca tgtacccggt tgtggtggcg | 1500 |
| catccagtgc acagactaaa tcctgctgac aggagaaggt cggtctcttc gtcggcactc | 1560 |
| gatgccgaca tccccagcgc agattttttcc ttcagccagg gatga | 1605 |

<210> SEQ ID NO 4
<211> LENGTH: 534
<212> TYPE: PRT
<213> ORGANISM: Triticum aestivum

<400> SEQUENCE: 4

```
Met Ala Glu Asp Asp Gly Tyr Pro Pro Ala Arg Thr Leu Pro Glu Thr
1               5                   10                  15
Pro Ser Trp Ala Val Ala Leu Val Phe Ala Val Met Ile Ile Val Ser
            20                  25                  30
Val Leu Leu Glu His Ala Leu His Lys Leu Gly Gln Trp Phe His Lys
        35                  40                  45
Arg His Lys Asn Ala Leu Ala Glu Ala Leu Glu Lys Met Lys Ala Glu
    50                  55                  60
Leu Met Leu Val Gly Phe Ile Ser Leu Leu Ala Val Thr Gln Asp
65                  70                  75                  80
Pro Ile Ser Gly Ile Cys Ile Ser Gln Lys Ala Ala Ser Ile Met Arg
                85                  90                  95
Pro Cys Lys Val Glu Pro Gly Ser Val Lys Ser Lys Tyr Lys Asp Tyr
            100                 105                 110
Tyr Cys Ala Lys Glu Gly Lys Val Ala Leu Met Ser Thr Gly Ser Leu
        115                 120                 125
His Gln Leu His Ile Phe Ile Phe Val Leu Ala Val Phe His Val Thr
    130                 135                 140
Tyr Ser Val Ile Ile Met Ala Leu Ser Arg Leu Lys Met Arg Thr Trp
145                 150                 155                 160
Lys Lys Trp Glu Thr Glu Thr Ala Ser Leu Glu Tyr Gln Phe Ala Asn
                165                 170                 175
Asp Pro Ala Arg Phe Arg Phe Thr His Gln Thr Ser Phe Val Lys Arg
            180                 185                 190
His Leu Gly Leu Ser Ser Thr Pro Gly Val Arg Trp Val Val Ala Phe
        195                 200                 205
Phe Arg Gln Phe Phe Arg Ser Val Thr Lys Val Asp Tyr Leu Thr Leu
    210                 215                 220
Arg Ala Gly Phe Ile Asn Ala His Leu Ser Gln Asn Ser Lys Phe Asp
225                 230                 235                 240
Phe His Lys Tyr Ile Lys Arg Ser Met Glu Asp Asp Phe Lys Val Val
                245                 250                 255
Val Gly Ile Ser Leu Pro Leu Trp Ala Val Ala Ile Leu Thr Leu Phe
            260                 265                 270
Leu Asp Ile Asp Gly Ile Gly Thr Leu Thr Trp Val Ser Phe Ile Pro
        275                 280                 285
Leu Ile Ile Leu Leu Cys Val Gly Thr Lys Leu Glu Met Ile Ile Met
    290                 295                 300
Glu Met Ala Leu Glu Ile Gln Asp Arg Ser Ser Val Ile Lys Gly Ala
305                 310                 315                 320
Pro Val Val Glu Pro Ser Asn Lys Phe Phe Trp Phe His Arg Pro Asp
                325                 330                 335
Trp Val Leu Phe Phe Ile His Leu Thr Leu Phe Gln Asn Ala Phe Gln
            340                 345                 350
Met Ala His Phe Val Trp Thr Val Ala Thr Pro Gly Leu Lys Asp Cys
        355                 360                 365
Phe His Met Asn Ile Gly Leu Ser Ile Met Lys Val Val Leu Gly Leu
    370                 375                 380
Ala Leu Gln Phe Leu Cys Ser Tyr Ile Thr Phe Pro Leu Tyr Ala Leu
385                 390                 395                 400
Val Thr Gln Met Gly Ser Asn Met Lys Arg Ser Ile Phe Asp Glu Gln
                405                 410                 415
```

```
Thr Ala Lys Ala Leu Thr Asn Trp Arg Asn Thr Ala Lys Glu Lys Lys
            420                 425                 430

Lys Val Arg Asp Thr Asp Met Leu Met Ala Gln Met Ile Gly Asp Ala
        435                 440                 445

Thr Pro Ser Arg Gly Thr Ser Pro Met Pro Ser Arg Gly Ser Ser Pro
    450                 455                 460

Val His Leu Leu Gln Lys Gly Met Gly Arg Ser Asp Asp Pro Gln Ser
465                 470                 475                 480

Ala Pro Thr Ser Pro Arg Thr Met Glu Glu Ala Arg Asp Met Tyr Pro
                485                 490                 495

Val Val Val Ala His Pro Val His Arg Leu Asn Pro Ala Asp Arg Arg
                500                 505                 510

Arg Ser Val Ser Ser Ser Ala Leu Asp Ala Asp Ile Pro Ser Ala Asp
            515                 520                 525

Phe Ser Phe Ser Gln Gly
    530

<210> SEQ ID NO 5
<211> LENGTH: 534
<212> TYPE: PRT
<213> ORGANISM: Triticum aestivum

<400> SEQUENCE: 5

Met Ala Glu Asp Asp Gly Tyr Pro Pro Ala Arg Thr Leu Pro Glu Thr
1               5                   10                  15

Pro Ser Trp Ala Val Ala Leu Val Phe Ala Val Met Ile Ile Val Ser
            20                  25                  30

Val Leu Leu Glu His Ala Leu His Lys Leu Gly Gln Trp Phe His Lys
        35                  40                  45

Arg His Lys Asn Ala Leu Ala Glu Ala Leu Glu Lys Ile Lys Ala Glu
    50                  55                  60

Leu Met Leu Val Gly Phe Ile Ser Leu Leu Ala Val Thr Gln Asp
65                  70                  75                  80

Pro Ile Ser Gly Ile Cys Ile Ser Glu Lys Ala Ala Ser Ile Met Arg
                85                  90                  95

Pro Cys Lys Leu Pro Pro Gly Ser Val Lys Ser Lys Tyr Lys Asp Tyr
            100                 105                 110

Tyr Cys Ala Lys Gln Gly Lys Val Ser Leu Met Ser Thr Gly Ser Leu
        115                 120                 125

His Gln Leu His Ile Phe Ile Phe Val Leu Ala Val Phe His Val Thr
    130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Val Arg Trp Val Val Ala Phe
        195                 200                 205

Phe Arg Gln Phe Phe Arg Ser Val Thr Lys Val Asp Tyr Leu Thr Leu
    210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Asp Phe Lys Val Val
```

```
                        245                 250                 255
        Val Gly Ile Ser Leu Pro Leu Trp Cys Val Ala Ile Leu Thr Leu Phe
                    260                 265                 270

Leu Asp Ile Asp Gly Ile Gly Thr Leu Thr Trp Ile Ser Phe Ile Pro
                    275                 280                 285

Leu Val Ile Leu Leu Cys Val Gly Thr Lys Leu Glu Met Ile Ile Met
                    290                 295                 300

Glu Met Ala Leu Glu Ile Gln Asp Arg Ala Ser Val Ile Lys Gly Ala
        305                 310                 315                 320

Pro Val Val Glu Pro Ser Asn Lys Phe Phe Trp Phe His Arg Pro Asp
                            325                 330                 335

Trp Val Leu Phe Phe Ile His Leu Thr Leu Phe Gln Asn Ala Phe Gln
                            340                 345                 350

Met Ala His Phe Val Trp Thr Val Ala Thr Pro Gly Leu Lys Lys Cys
                            355                 360                 365

Phe His Met His Ile Gly Leu Ser Ile Met Lys Val Val Leu Gly Leu
                            370                 375                 380

Ala Leu Gln Phe Leu Cys Ser Tyr Ile Thr Phe Pro Leu Tyr Ala Leu
        385                 390                 395                 400

Val Thr Gln Met Gly Ser Asn Met Lys Arg Ser Ile Phe Asp Glu Gln
                            405                 410                 415

Thr Ala Lys Ala Leu Thr Asn Trp Arg Asn Thr Ala Lys Glu Lys Lys
                            420                 425                 430

Lys Val Arg Asp Thr Asp Met Leu Met Ala Gln Met Ile Gly Asp Ala
                            435                 440                 445

Thr Pro Ser Arg Gly Ala Ser Pro Met Pro Ser Arg Gly Ser Ser Pro
                            450                 455                 460

Val His Leu Leu His Lys Gly Met Gly Arg Ser Asp Asp Pro Gln Ser
        465                 470                 475                 480

Thr Pro Thr Ser Pro Arg Ala Met Glu Glu Ala Arg Asp Met Tyr Pro
                            485                 490                 495

Val Val Val Ala His Pro Val His Arg Leu Asn Pro Ala Asp Arg Arg
                            500                 505                 510

Arg Ser Val Ser Ser Ser Ala Leu Asp Val Asp Ile Pro Ser Ala Asp
                            515                 520                 525

Phe Ser Phe Ser Gln Gly
                            530

<210> SEQ ID NO 6
<211> LENGTH: 534
<212> TYPE: PRT
<213> ORGANISM: Triticum aestivum

<400> SEQUENCE: 6

Met Ala Glu Asp Asp Gly Tyr Pro Pro Ala Arg Thr Leu Pro Glu Thr
1               5                   10                  15

Pro Ser Trp Ala Val Ala Leu Val Phe Ala Val Met Ile Ile Val Ser
                20                  25                  30

Val Leu Leu Glu His Ala Leu His Lys Leu Gly Gln Trp Phe His Lys
            35                  40                  45

Arg His Lys Asn Ala Leu Ala Glu Ala Leu Glu Lys Ile Lys Ala Glu
        50                  55                  60

Leu Met Leu Val Gly Phe Ile Ser Leu Leu Leu Ala Val Thr Gln Asp
65                  70                  75                  80
```

```
Pro Ile Ser Gly Ile Cys Ile Ser Glu Lys Ala Ala Ser Ile Met Arg
                85                  90                  95
Pro Cys Ser Leu Pro Pro Gly Ser Val Lys Ser Lys Tyr Lys Asp Tyr
            100                 105                 110
Tyr Cys Ala Lys Lys Gly Lys Val Ser Leu Met Ser Thr Gly Ser Leu
            115                 120                 125
His Gln Leu His Ile Phe Ile Phe Val Leu Ala Val Phe His Val Thr
        130                 135                 140
Tyr Ser Val Ile Ile Met Ala Leu Ser Arg Leu Lys Met Arg Thr Trp
145                 150                 155                 160
Lys Lys Trp Glu Thr Glu Thr Ala Ser Leu Glu Tyr Gln Phe Ala Asn
                165                 170                 175
Asp Pro Ala Arg Phe Arg Phe Thr His Gln Thr Ser Phe Val Lys Arg
            180                 185                 190
His Leu Gly Leu Ser Ser Thr Pro Gly Ile Arg Trp Val Val Ala Phe
            195                 200                 205
Phe Arg Gln Phe Phe Arg Ser Val Thr Lys Val Asp Tyr Leu Thr Leu
        210                 215                 220
Arg Ala Gly Phe Ile Asn Ala His Leu Ser His Asn Ser Lys Phe Asp
225                 230                 235                 240
Phe His Lys Tyr Ile Lys Arg Ser Met Glu Asp Phe Lys Val Val
                245                 250                 255
Val Gly Ile Ser Leu Pro Leu Trp Cys Val Ala Ile Leu Thr Leu Phe
                260                 265                 270
Leu Asp Ile Asp Gly Ile Gly Thr Leu Thr Trp Ile Ser Phe Ile Pro
            275                 280                 285
Leu Val Ile Leu Leu Cys Val Gly Thr Lys Leu Glu Met Ile Ile Met
        290                 295                 300
Glu Met Ala Leu Glu Ile Gln Asp Arg Ala Ser Val Ile Lys Gly Ala
305                 310                 315                 320
Pro Val Val Glu Pro Ser Asn Lys Phe Phe Trp Phe His Arg Pro Asp
                325                 330                 335
Trp Val Leu Phe Phe Ile His Leu Thr Leu Phe Gln Asn Ala Phe Gln
            340                 345                 350
Met Ala His Phe Val Trp Thr Val Ala Thr Pro Gly Leu Lys Lys Cys
            355                 360                 365
Phe His Met His Ile Gly Leu Ser Ile Met Lys Val Val Leu Gly Leu
        370                 375                 380
Ala Leu Gln Phe Leu Cys Ser Tyr Ile Thr Phe Pro Leu Tyr Ala Leu
385                 390                 395                 400
Val Thr Gln Met Gly Ser Asn Met Lys Arg Ser Ile Phe Asp Glu Gln
                405                 410                 415
Thr Ala Lys Ala Leu Thr Asn Trp Arg Asn Thr Ala Lys Glu Lys Lys
            420                 425                 430
Lys Val Arg Asp Thr Asp Met Leu Met Ala Gln Met Ile Gly Asp Ala
            435                 440                 445
Thr Pro Ser Arg Gly Ala Ser Pro Met Pro Ser Arg Gly Ser Ser Pro
450                 455                 460
Val His Leu Leu His Lys Gly Met Gly Arg Ser Asp Asp Pro Gln Ser
465                 470                 475                 480
Thr Pro Thr Ser Pro Arg Ala Met Glu Glu Ala Arg Asp Met Tyr Pro
                485                 490                 495
Val Val Val Ala His Pro Val His Arg Leu Asn Pro Ala Asp Arg Arg
```

```
                500             505             510
Arg Ser Val Ser Ser Ala Leu Asp Ala Asp Ile Pro Ser Ala Asp
        515                 520                 525

Phe Ser Phe Ser Gln Gly
    530

<210> SEQ ID NO 7
<211> LENGTH: 4017
<212> TYPE: DNA
<213> ORGANISM: Artificial Sequence
<220> FEATURE:
<223> OTHER INFORMATION: Vector

<400> SEQUENCE: 7
tcgtgcccct ctctagagat aatgagcatt gcatgtctaa gttataaaaa attaccacat     60 atttttttg tcacacttgt ttgaagtgca gtttatctat ctttatacat atatttaaac    120
tttactctac gaataatata atctatagta ctacaataat atcagtgttt tagagaatca    180
tataaatgaa cagttagaca tggtctaaag gacaattgag tattttgaca acaggactct    240
acagttttat cttttagtg tgcatgtgtt ctccttttt tttgcaaata gcttcaccta    300
tataatactt catccatttt attagtacat ccatttaggg tttagggtta atggtttta    360 tagactaatt ttttagtac atctattta ttctattta gcctctaaat taagaaaact    420
aaaactctat tttagttttt ttatttaata atttagatat aaaatagaat aaaataaagt    480
gactaaaaat taaacaaata cccttaaga aattaaaaaa actaaggaaa cattttctt    540 gtttcgagta gataatgcca gcctgttaaa cgccgtcgac gagtctaacg acaccaacc    600 agcgaaccag cagcgtcgcg tcgggccaag cgaagcagac ggcacggcat ctctgtcgct    660
gcctctggac ccctctcgat cgagagttcc gctccaccgt tggacttgct ccgctgtcgg    720
catccagaaa ttgcgtggcg gagcggcaga cgtgagccgg cacggcaggc ggcctcctcc    780
tcctctcacg gcaccggcag ctacggggga ttccttcc accgctcctt cgctttccct    840
tcctcgcccg ccgtaataaa tagacacccc ctccacaccc tctttcccca acctcgtgtt    900
gttcggagcg cacacacaca caaccagatc tcccccaaat ccaccgtcg cacctccgc    960 ttcaaggtac gccgctcgtc ctcccccccc cccctctct accttctcta gatcggcgtt   1020
ccggtccatg gttagggccc ggtagttcta cttctgttca tgtttgtgtt agatccgtgt   1080
ttgtgttaga tccgtgctgc tagcgttcgt acacggatgc gacctgtacg tcagacacgt   1140
tctgattgct aacttgccag tgtttctctt tggggaatcc tgggatggct ctagccgttc   1200
cgcagacggg atcgatttca tgattttttt tgtttcgttg catagggttt ggtttgccct   1260
tttcctttat ttcaatatat gccgtgcact tgtttgtcgg gtcatctttt catgcttttt   1320
tttgtcttgg ttgtgatgat gtggtctggt tgggcggtcg ttctagatcg gagtagaatt   1380
aattctgttt caaactacct ggtggattta ttaattttgg atctgtatgt gtgtgccata   1440
catattcata gttacgaatt gaagatgatg gatggaaata tcgatctagg ataggtatac   1500
atgttgatgc gggttttact gatgcatata cagagatgct ttttgttcgc ttggttgtga   1560
tgatgtggtg tggttgggcg gtcgttcatt cgttctagat cggagtagaa tactgtttca   1620
aactacctgg tgtatttatt aatttttggaa ctgtatgtgt gtgtcataca tcttcatagt   1680
tacgagttta agatggatgg aaatatcgat ctaggatagg tatacatgtt gatgtgggtt   1740
ttactgatgc atatacatga tggcatatgc agcatctatt catatgctct aaccttgagt   1800
acctatctat tataataaac aagtatgttt tataattatt ttgatcttga tatacttgga   1860
```

```
tgatggcata tgcagcagct atatgtggat tttttagcc ctgccttcat acgctattta    1920
tttgcttggt actgtttctt ttgtcgatgc tcaccctgtt gtttggtgtt acttctgcaa    1980
aagcttgcca agctatcaaa caagtttgta caaaaaagct gaacgagaaa cgtaaaatga    2040
tataaatatc aatatattaa attagatttt gcataaaaaa cagactacat aatactgtaa    2100
aacacaacat atccagtcac tatggcggcc gcattaggca ccccaggctt tacactttat    2160
gcttccggct cgtataatgt gtggattttg agtaggatc cggcgagatt ttcaggagct    2220
aaggaagcta aaatggagaa aaaatcact ggatatacca ccgttgatat atcccaatgg    2280
catcgtaaag aacattttga ggcatttcag tcagttgctc aatgtaccta taaccagacc    2340
gttcagctgg atattacggc cttttaaag accgtaaaga aaaataagca caagttttat    2400
ccggccttta ttcacattct tgcccgcctg atgaatgctc atccggaatt ccgtatggca    2460
atgaaagacg gtgagctggt gatatgggat agtgttcacc cttgttacac cgttttccat    2520
gagcaaactg aaacgttttc atcgctctgg agtgaatacc acgacgattt ccggcagttt    2580
ctacacatat attcgcaaga tgtggcgtgt tacggtgaaa acctggccta tttccctaaa    2640
gggtttattg agaatatgtt tttcgtctca gccaatccct gggtgagttt caccagtttt    2700
gatttaaacg tggccaatat ggacaacttc ttcgccccg ttttcaccat gggcaaatat    2760
tatacgcaag cgacaaggt gctgatgccg ctggcgattc aggttcatca tgccgtctgt    2820
gatggcttcc atgtcggcag aatgcttaat gaattacaac agtactgcga tgagtggcag    2880
ggcggggcgt aatctagagg atccggctta ctaaaagcca gataacagta tgcgtatttg    2940
cgcgctgatt tttgcggtat aagaatatat actgatatgt atacccgaag tatgtcaaaa    3000
agaggtgtgc tatgaagcag cgtattacag tgacagttga cagcgacagc tatcagttgc    3060
tcaaggcata tatgatgtca atatctccgg tctggtaagc acaaccatgc agaatgaagc    3120
ccgtcgtctg cgtgccgaac gctggaaagc ggaaaatcag gaagggatgg ctgaggtcgc    3180
ccggtttatt gaaatgaacg gctctttttgc tgacgagaac agggactggt gaaatgcagt    3240
ttaaggttta cacctataaa agagagagcc gttatcgtct gttttgtggat gtacagagtg    3300 atattattga cacgcccggg cgacggatgg tgatccccct ggccagtgca cgtctgctgt    3360
cagataaagt ctcccgtgaa ctttacccgg tggtgcatat cggggatgaa agctggcgca    3420
tgatgaccac cgatatggcc agtgtgccgg tctccgttat cggggaagaa gtggctgatc    3480
tcagccaccg cgaaaatgac atcaaaaacg ccattaacct gatgttctgg ggaatataaa    3540
tgtcaggctc ccttatacac agccagtctg caggtcgacc atagtgactg gatatgttgt    3600
gttttacagt attatgtagt ctgttttta tgcaaaatct aatttaatat attgatattt    3660
atatcatttt acgtttctcg ttcagctttc ttgtacaaag tggttcgata attccttaat    3720
taactagttc tagagcggcc gcccaccgcg gtggagctcg aatttccccg atcgttcaaa    3780
catttggcaa taaagtttct taagattgaa tcctgttgcc ggtcttgcga tgattatcat    3840
ataatttctg ttgaattacg ttaagcatgt aataattaac atgtaatgca tgacgttatt    3900
tatgagatgg gttttatga ttagagtccc gcaattatac atttaatacg cgatagaaaa    3960
caaaatatag cgcgcaaact aggataaatt atcgcgcgcg gtgtcatcta tgttact     4017
```

<210> SEQ ID NO 8
<211> LENGTH: 2202
<212> TYPE: DNA
<213> ORGANISM: Artificial Sequence
<220> FEATURE:

<223> OTHER INFORMATION: Vector

<400> SEQUENCE: 8

```
tctagaatgg tggatctacg cacgctcggc tacagtcagc agcagcaaga gaagatcaaa      60
ccgaaggtgc gttcgacagt ggcgcagcac cacgaggcac tggtgggcca tgggtttaca     120
cacgcgcaca tcgttgcgct cagccaacac ccggcagcgt tagggaccgt cgctgtcacg     180
tatcagcaca taatcacggc gttgccagag gcgacacacg aagacatcgt tggcgtcggc     240
aaacagtggt ccggcgcacg cgccctggag gccttgctca cggatgcggg ggagttgaga     300
ggtccgccgt tacagttgga cacaggccaa cttgtgaaga ttgcaaaacg tggcggcgtg     360
accgcaatgg aggcagtgca tgcatcgcgc aatgcactga cgggtgcccc cctgaacctg     420
acccccgacc aagtggtggc tatcgccagc cacgatggcg gcaagcaagc gctcgaaacg     480
gtgcagcggc tgttgccggt gctgtgccag gaccatggcc tgaccccgga ccaagtggtg     540
gctatcgcca gcaacaatgg cggcaagcaa gcgctcgaaa cggtgcagcg gctgttgccg     600
gtgctgtgcc aggaccatgg cctgactccg gaccaagtgg tggctatcgc cagccacgat     660
ggcggcaagc aagcgctcga aacggtgcag cggctgttgc cggtgctgtg ccaggaccat     720
ggcctgaccc cggaccaagt ggtggctatc gccagcaacg gtggcggcaa gcaagcgctc     780
gaaacggtgc agcggctgtt gccggtgctg tgccaggacc atggcctgac cccggaccaa     840
gtggtggcta tcgccagcaa caatggcggc aagcaagcgc tcgaaacggt gcagcggctg     900
ttgccggtgc tgtgccagga ccatggcctg actccggacc aagtggtggc tatcgccagc     960
cacgatggcg gcaagcaagc gctcgaaacg gtgcagcggc tgttgccggt gctgtgccag    1020
gaccatggcc tgaccccgga ccaagtggtg gctatcgcca gcaacggtgg cggcaagcaa    1080
gcgctcgaaa cggtgcagcg gctgttgccg gtgctgtgcc aggaccatgg cctgaccccg    1140
gaccaagtgg tggctatcgc cagcaacaat ggcggcaagc aagcgctcga aacggtgcag    1200
cggctgttgc cggtgctgtg ccaggaccat ggcctgactc cggaccaagt ggtggctatc    1260
gccagccacg atggcggcaa gcaagcgctc gaaacggtgc agcggctgtt gccggtgctg    1320
tgccaggacc atggcctgac cccggaccaa gtggtggcta tcgccagcaa cggtggcggc    1380
aagcaagcgc tcgaaacggt gcagcggctg ttgccggtgc tgtgccagga ccatggcctg    1440
accccggacc aagtggtggc tatcgccagc cacgatggcg gcaagcaagc gctcgaaacg    1500
gtgcagcggc tgttgccggt gctgtgccag gaccatggcc tgaccccgga ccaagtggtg    1560
gctatcgcca gcaacaatgg cggcaagcaa gcgctcgaaa cggtgcagcg gctgttgccg    1620
gtgctgtgcc aggaccatgg cctgactccg gaccaagtgg tggctatcgc cagccacgat    1680
ggcggcaagc aagcgctcga aacggtgcag cggctgttgc cggtgctgtg ccaggaccat    1740
ggcctgactc cggaccaagt ggtggctatc gccagccacg atggcggcaa gcaagcgctc    1800
gaaacggtgc agcggctgtt gccggtgctg tgccaggacc atggcctgac cccggaccaa    1860
gtggtggcta tcgccagcaa caatggcggc aagcaagcgc tcgaaacggt gcagcggctg    1920
ttgccggtgc tgtgccagga ccatggcctg accccggacc aagtggtggc tatcgccagc    1980
aacggtggcg gcaagcaagc gctcgaaagc attgtggccc agctgagccg gcctgatccg    2040
gcgttggccg cgttgaccaa cgaccacctc gtcgccttgg cctgcctcgg cggacgtcct    2100
gccatggatg cagtgaaaaa gggattgccg cacgcgccgg aattgatcag aagagtcaat    2160
cgccgtattg gcgaacgcac gtcccatcgc gttgccggat cc                       2202
```

<210> SEQ ID NO 9
<211> LENGTH: 2304
<212> TYPE: DNA
<213> ORGANISM: Artificial Sequence
<220> FEATURE:
<223> OTHER INFORMATION: Vector

<400> SEQUENCE: 9

```
tctagaatgg tggatctacg cacgctcggc tacagtcagc agcagcaaga gaagatcaaa      60
ccgaaggtgc gttcgacagt ggcgcagcac cacgaggcac tggtgggcca tgggtttaca     120
cacgcgcaca tcgttgcgct cagccaacac ccggcagcgt tagggaccgt cgctgtcacg     180
tatcagcaca taatcacggc gttgccgaga gcgacacacg aagacatcgt tggcgtcggc     240
aaacagtggt ccggcgcacg cgccctggag gccttgctca cggatgcggg ggagttgaga     300
ggtccgccgt tacagttgga cacaggccaa cttgtgaaga ttgcaaaacg tggcggcgtg     360
accgcaatgg aggcagtgca tgcatcgcgc aatgcactga cgggtgcccc cctgaacctg     420
accccggacc aagtggtggc tatcgccagc aacaagggcg gcaagcaagc gctcgaaacg     480
gtgcagcggc tgttgccggt gctgtgccag gaccatggcc tgaccccgga ccaagtggtg     540
gctatcgcca gcaacaaggg cggcaagcaa gcgctcgaaa cggtgcagcg gctgttgccg     600
gtgctgtgcc aggaccatgg cctgaccccg gaccaagtgg tggctatcgc cagcaacaag     660
ggcggcaagc aagcgctcga aacggtgcag cggctgttgc cggtgctgtg ccaggaccat     720
ggcctgaccc cggaccaagt ggtggctatc gccagcaaca ttggcggcaa gcaagcgctc     780
gaaacggtgc agcggctgtt gccggtgctg tgccaggacc atggcctgac cccggaccaa     840
gtggtggcta tcgccagcaa caagggcggc aagcaagcgc tcgaaacggt gcagcggctg     900
ttgccggtgc tgtgccagga ccatggcctg accccggacc aagtggtggc tatcgccagc     960
aacattggcg gcaagcaagc gctcgaaacg gtgcagcggc tgttgccggt gctgtgccag    1020
gaccatggcc tgaccccgga ccaagtggtg gctatcgcca gcaacggtgg cggcaagcaa    1080
gcgctcgaaa cggtgcagcg gctgttgccg gtgctgtgcc aggaccatgg cctgaccccg    1140
gaccaagtgg tggctatcgc cagcaacaag ggcggcaagc aagcgctcga aacggtgcag    1200
cggctgttgc cggtgctgtg ccaggaccat ggcctgactc cggaccaagt ggtggctatc    1260
gccagccacg atggcggcaa gcaagcgctc gaaacggtgc agcggctgtt gccggtgctg    1320
tgccaggacc atggcctgac cccggaccaa gtggtggcta tcgccagcaa cattggcggc    1380
aagcaagcgc tcgaaacggt gcagcggctg ttgccggtgc tgtgccagga ccatggcctg    1440
accccggacc aagtggtggc tatcgccagc aacggtggcg gcaagcaagc gctcgaaacg    1500
gtgcagcggc tgttgccggt gctgtgccag gaccatggcc tgaccccgga ccaagtggtg    1560
gctatcgcca gcaacattgg cggcaagcaa gcgctcgaaa cggtgcagcg gctgttgccg    1620
gtgctgtgcc aggaccatgg cctgaccccg gaccaagtgg tggctatcgc cagcaacggt    1680
ggcggcaagc aagcgctcga aacggtgcag cggctgttgc cggtgctgtg ccaggaccat    1740
ggcctgactc cggaccaagt ggtggctatc gccagccacg atggcggcaa gcaagcgctc    1800
gaaacggtgc agcggctgtt gccggtgctg tgccaggacc atggcctgac tccggaccaa    1860
gtggtggcta tcgccagcca cgatggcggc aagcaagcgc tcgaaacggt gcagcggctg    1920
ttgccggtgc tgtgccagga ccatggcctg actccggacc aagtggtggc tatcgccagc    1980
cacgatggcg gcaagcaagc gctcgaaacg gtgcagcggc tgttgccggt gctgtgccag    2040
gaccatggcc tgaccccgga ccaagtggtg gctatcgcca gcaacaaggg cggcaagcaa    2100
```

-continued

```
gcgctcgaaa gcattgtggc ccagctgagc cggcctgatc cggcgttggc cgcgttgacc    2160
aacgaccacc tcgtcgcctt ggcctgcctc ggcggacgtc ctgccatgga tgcagtgaaa    2220
aagggattgc cgcacgcgcc ggaattgatc agaagagtca atcgccgtat tggcgaacgc    2280
acgtcccatc gcgttgccgg atcc                                           2304
```

<210> SEQ ID NO 10
<211> LENGTH: 6219
<212> TYPE: DNA
<213> ORGANISM: Artificial Sequence
<220> FEATURE:
<223> OTHER INFORMATION: Vector

<400> SEQUENCE: 10

```
caaataatga ttttattttg actgatagtg acctgttcgt tgcaacaaat tgatgagcaa      60
tgctttttta taatgccaac tttgtacaaa aaagcaggct ccgaattcgc ccttcaccat     120
ggattataag gatcacgatg gcgactacaa ggaccacgat attgactaca agacgatga     180 cgataaaatg gctcctaaga aaaagcgcaa agtcggtatc catggcgttc cctctagaat     240
ggtggatcta cgcacgctcg gctacagtca gcagcagcaa gagaagatca accgaaggt     300 gcgttcgaca gtggcgcagc accacgaggc actggtgggc catgggttta cacacgcgca     360
catcgttgcg ctcagccaac acccggcagc gttagggacc gtcgctgtca cgtatcagca     420
cataatcacg cgcgttgccag aggcgacaca cgaagacatc gttggcgtcg gcaaacagtg     480
gtccggcgca cgcgccctgg aggccttgct cacggatgcg ggggagttga gaggtccgcc     540
gttacagttg gacacaggcc aacttgtgaa gattgcaaaa cgtggcggcg tgaccgcaat     600
ggaggcagtg catgcatcgc gcaatgcact gacgggtgcc ccctgaacc tgaccccgga     660 ccaagtggtg gctatcgcca gccacgatgg cggcaagcaa gcgctcgaaa cggtgcagcg     720
gctgttgccg gtgctgtgcc aggaccatgg cctgaccccg gaccaagtgg tggctatcgc     780
cagcaacaat ggcggcaagc aagcgctcga aacggtgcag cggctgttgc cggtgctgtg     840
ccaggaccat ggcctgactc cggaccaagt ggtggctatc gccagccacg atggcggcaa     900
gcaagcgctc gaaacggtgc agcggctgtt gccggtgctg tgccaggacc atggcctgac     960
cccggaccaa gtggtggcta tcgccagcaa cggtggcggc aagcaagcgc tcgaaacggt    1020
gcagcggctg ttgccggtgc tgtgccagga ccatggcctg accccggacc aagtggtggc    1080
tatcgccagc aacaatggcg gcaagcaagc gctcgaaacg gtgcagcggc tgttgccggt    1140
gctgtgccag gaccatggcc tgactccgga ccaagtggtg gctatcgcca gccacgatgg    1200
cggcaagcaa gcgctcgaaa cggtgcagcg gctgttgccg gtgctgtgcc aggaccatgg    1260
cctgaccccg gaccaagtgg tggctatcgc cagcaacggt ggcggcaagc aagcgctcga    1320
aacggtgcag cggctgttgc cggtgctgtg ccaggaccat ggcctgaccc cggaccaagt    1380
ggtggctatc gccagcaaca atggcggcaa gcaagcgctc gaaacggtgc agcggctgtt    1440
gccggtgctg tgccaggacc atggcctgac tccggaccaa gtggtggcta tcgccagcca    1500
cgatggcggc aagcaagcgc tcgaaacggt gcagcggctg ttgccggtgc tgtgccagga    1560
ccatggcctg accccggacc aagtggtggc tatcgccagc aacggtggcg gcaagcaagc    1620
gctcgaaacg gtgcagcggc tgttgccggt gctgtgccag gaccatggcc tgaccccgga    1680
ccaagtggtg gctatcgcca gccacgatgg cggcaagcaa gcgctcgaaa cggtgcagcg    1740
gctgttgccg gtgctgtgcc aggaccatgg cctgaccccg gaccaagtgg tggctatcgc    1800
cagcaacaat ggcggcaagc aagcgctcga aacggtgcag cggctgttgc cggtgctgtg    1860
```

```
ccaggaccat ggcctgactc cggaccaagt ggtggctatc gccagccacg atggcggcaa    1920
gcaagcgctc gaaacggtgc agcggctgtt gccggtgctg tgccaggacc atggcctgac    1980
tccggaccaa gtggtggcta tcgccagcca cgatggcggc aagcaagcgc tcgaaacggt    2040
gcagcggctg ttgccggtgc tgtgccagga ccatggcctg accccggacc aagtggtggc    2100
tatcgccagc aacaatggcg gcaagcaagc gctcgaaacg gtgcagcggc tgttgccggt    2160
gctgtgccag gaccatggcc tgaccccgga ccaagtggtg gctatcgcca gcaacggtgg    2220
cggcaagcaa gcgctcgaaa gcattgtggc ccagctgagc cggcctgatc ggcgttggc     2280 cgcgttgacc aacgaccacc tcgtcgcctt ggcctgcctc ggcggacgtc ctgccatgga    2340
tgcagtgaaa aagggattgc cgcacgcgcc ggaattgatc agaagagtca atcgccgtat    2400
tggcgaacgc acgtcccatc gcgttgccgg atcccagctg gtgaagtccg agctggaaga    2460
aaaaaagagc gagctgcgcc acaagctcaa gtacgtgccc cacgagtaca tcgagctgat    2520
cgagatcgcc cgcaacagca cccaagaccg catcctggag atgaaagtga tggagttctt    2580
catgaaggtg tacggctacc gcggcaagca cctgggcggc tcccgcaagc ccgatggcgc    2640
catctacacc gtgggctccc ccatcgacta tggcgtcatt gtcgacacca aggcctactc    2700
cggcggctac aacttaccca tcggtcaggc cgacgagatg caacgctacg tgaaggagaa    2760
ccagacccgc aataagcaca ttaatcccaa cgagtggtgg aaggtgtacc cctcctccgt    2820
gaccgagttc aaaattcctgt tcgtgtccgg ccacttcaag ggcaattata aggcccaact    2880
gacccgcctg aaccacaaga ccaactgcaa cggcgccgtg ctgtccgtgg aggaactgct    2940
gatcggcggc gagatgatca aggctggtac cctgaccctg aagaggtgc gccgcaagtt     3000 caacaatggt gaaatcaatt tcaggtccgg cggcggagag ggcagaggaa gtcttctaac    3060
atgcggtgac gtggaggaga atcccggccc taggatggac tacaaagacc atgacggtga    3120
ttataaagat catgacatcg attacaagga tgacgatgac aagatggccc ccaagaagaa    3180
gaggaaggtg ggcattcacg gggtgccggc tagcatggtg gatctacgca cgctcggcta    3240
cagtcagcag cagcaagaga agatcaaaacc gaaggtgcgt tcgacagtgg cgcagcacca    3300
cgaggcactg gtgggccatg ggtttacaca cgcgcacatc gttgcgctca gccaacaccc    3360
ggcagcgtta gggaccgtcg ctgtcacgta tcagcacata atcacggcgt tgccagaggc    3420
gacacacgaa gacatcgttg gcgtcggcaa acagtggtcc ggcgcacgcg ccctggaggc    3480
cttgctcacg gatgcggggg agttgagagg tccgccgtta cagttggaca caggccaact    3540
tgtgaagatt gcaaaacgtg gcggcgtgac cgcaatggag gcagtgcatg catcgcgcaa    3600
tgcactgacg ggtgccccc tgaacctgac cccggaccaa gtggtggcta tcgccagcaa     3660
caagggcggc aagcaagcgc tcgaaacggt gcagcggctg ttgccggtgc tgtgccagga    3720
ccatggcctg accccggacc aagtggtggc tatcgccagc aacaagggcg gcaagcaagc    3780
gctcgaaacg gtgcagcggc tgttgccggt gctgtgccag gaccatggcc tgaccccgga    3840
ccaagtggtg gctatcgcca gcaacaaggg cggcaagcaa gcgctcgaaa cggtgcagcg    3900
gctgttgccg gtgctgtgcc aggaccatgg cctgaccccg gaccaagtgg tggctatcgc    3960
cagcaacatt ggcggcaagc aagcgctcga aacggtgcag cggctgttgc cggtgctgtg    4020
ccaggaccat ggcctgaccc cggaccaagt ggtggctatc gccagcaaca agggcggcaa    4080
gcaagcgctc gaaacggtgc agcggctgtt gccggtgctg tgccaggacc atggcctgac    4140
cccggaccaa gtggtggcta tcgccagcaa cattggcggc aagcaagcgc tcgaaacggt    4200
```

```
gcagcggctg ttgccggtgc tgtgccagga ccatggcctg accccggacc aagtggtggc    4260
tatcgccagc aacggtggcg gcaagcaagc gctcgaaacg gtgcagcggc tgttgccggt    4320
gctgtgccag gaccatggcc tgaccccgga ccaagtggtg gctatcgcca gcaacaaggg    4380
cggcaagcaa gcgctcgaaa cggtgcagcg gctgttgccg gtgctgtgcc aggaccatgg    4440
cctgactccg gaccaagtgg tggctatcgc cagccacgat ggcggcaagc aagcgctcga    4500
aacggtgcag cggctgttgc cggtgctgtg ccaggaccat ggcctgaccc cggaccaagt    4560
ggtggctatc gccagcaaca ttggcggcaa gcaagcgctc gaaacggtgc agcggctgtt    4620
gccggtgctg tgccaggacc atggcctgac cccggaccaa gtggtggcta tcgccagcaa    4680
cggtggcggc aagcaagcgc tcgaaacggt gcagcggctg ttgccggtgc tgtgccagga    4740
ccatggcctg accccggacc aagtggtggc tatcgccagc aacattggcg gcaagcaagc    4800
gctcgaaacg gtgcagcggc tgttgccggt gctgtgccag gaccatggcc tgaccccgga    4860
ccaagtggtg gctatcgcca gcaacggtgg cggcaagcaa gcgctcgaaa cggtgcagcg    4920
gctgttgccg gtgctgtgcc aggaccatgg cctgactccg gaccaagtgg tggctatcgc    4980
cagccacgat ggcggcaagc aagcgctcga aacggtgcag cggctgttgc cggtgctgtg    5040
ccaggaccat ggcctgactc cggaccaagt ggtggctatc gccagccacg atggcggcaa    5100
gcaagcgctc gaaacggtgc agcggctgtt gccggtgctg tgccaggacc atggcctgac    5160
tccggaccaa gtggtggcta tcgccagcca cgatggcggc aagcaagcgc tcgaaacggt    5220
gcagcggctg ttgccggtgc tgtgccagga ccatggcctg accccggacc aagtggtggc    5280
tatcgccagc aacaagggcg gcaagcaagc gctcgaaagc attgtggccc agctgagccg    5340
gcctgatccg gcgttggccg cgttgaccaa cgaccacctc gtcgccttgg cctgcctcgg    5400
cggacgtcct gccatggatg cagtgaaaaa gggattgccg cacgcgccgg aattgatcag    5460
aagagtcaat cgccgtattg gcgaacgcac gtcccatcgc gttgccagat ctcaactagt    5520
caaaagtgaa ctggaggaga agaaatctga acttcgtcat aaattgaaat atgtgcctca    5580
tgaatatatt gaattaattg aaattgccag aaattccact caggatagaa ttcttgaaat    5640
gaaggtaatg gaatttttta tgaaagttta tggatataga ggtaaacatt tgggtggatc    5700
aaggaaaccg gacggagcaa tttatactgt cggatctcct attgattacg gtgtgatcgt    5760
ggatactaaa gcttatagcg gaggttataa tctgccaatt ggccaagcag atgaaatgga    5820
gcgatatgtc gaagaaaatc aaacacgaaa caaacatctc aaccctaatg aatggtggaa    5880
agtctatcca tcttctgtaa cggaatttaa gttttatttt gtgagtggtc actttaaagg    5940
aaactacaaa gctcagctta cacgattaaa tcatatcact aattgtaatg gagctgttct    6000
tagtgtagaa gagcttttaa ttggtggaga atgattaaaa gccggcacat taaccttaga    6060
ggaagtgaga cggaaattta ataacggcga gataaacttt taatagaagg gcgaattcga    6120
cccagctttc ttgtacaaag ttggcattat aaaaaataat tgctcatcaa tttgttgcaa    6180
cgaacaggtc actatcagtc aaaataaaat cattatttg                          6219

<210> SEQ ID NO 11
<211> LENGTH: 5868
<212> TYPE: DNA
<213> ORGANISM: Triticum aestivum

<400> SEQUENCE: 11
atggtggatc tacgcacgct cggctacagt cagcagcagc aagagaagat caaaccgaag      60
gtgcgttcga cagtggcgca gcaccacgag gcactggtgg gccatgggtt tacacacgcg     120
```

-continued

```
cacatcgttg cgctcagcca acacccggca gcgttaggga ccgtcgctgt cacgtatcag      180
cacataatca cggcgttgcc agaggcgaca cacgaagaca tcgttggcgt cggcaaacag      240
tggtccggcg cacgcgccct ggaggccttg ctcacggatg cggggagtt gagaggtccg       300 ccgttacagt tggacacagg ccaacttgtg aagattgcaa acgtggcgg cgtgaccgca       360 atggaggcag tgcatgcatc gcgcaatgca ctgacgggtg ccccctgaa cctgaccccg       420 gaccaagtgg tggctatcgc cagccacgat ggcggcaagc aagcgctcga aacggtgcag      480
cggctgttgc cggtgctgtg ccaggaccat ggcctgaccc cggaccaagt ggtggctatc      540
gccagcaaca atggcggcaa gcaagcgctc gaaacggtgc agcggctgtt gccggtgctg      600
tgccaggacc atggcctgac tccggaccaa gtggtggcta tcgccagcca cgatggcggc      660
aagcaagcgc tcgaaacggt gcagcggctg ttgccggtgc tgtgccagga ccatggcctg      720
accccggacc aagtggtggc tatcgccagc aacggtggcg gcaagcaagc gctcgaaacg      780
gtgcagcggc tgttgccggt gctgtgccag gaccatggcc tgaccccgga ccaagtggtg      840
gctatcgcca gcaacaatgg cggcaagcaa gcgctcgaaa cggtgcagcg gctgttgccg      900
gtgctgtgcc aggaccatgg cctgactccg gaccaagtgg tggctatcgc cagccacgat      960
ggcggcaagc aagcgctcga aacggtgcag cggctgttgc cggtgctgtg ccaggaccat     1020
ggcctgaccc cggaccaagt ggtggctatc gccagcaacg gtggcggcaa gcaagcgctc     1080
gaaacggtgc agcggctgtt gccggtgctg tgccaggacc atggcctgac cccggaccaa     1140
gtggtggcta tcgccagcaa caatggcggc aagcaagcgc tcgaaacggt gcagcggctg     1200
ttgccggtgc tgtgccagga ccatggcctg actccggacc aagtggtggc tatcgccagc     1260
cacgatggcg gcaagcaagc gctcgaaacg gtgcagcggc tgttgccggt gctgtgccag     1320
gaccatggcc tgaccccgga ccaagtggtg gctatcgcca gcaacggtgg cggcaagcaa     1380
gcgctcgaaa cggtgcagcg gctgttgccg gtgctgtgcc aggaccatgg cctgaccccg     1440
gaccaagtgg tggctatcgc cagccacgat ggcggcaagc aagcgctcga aacggtgcag     1500
cggctgttgc cggtgctgtg ccaggaccat ggcctgaccc cggaccaagt ggtggctatc     1560
gccagcaaca atggcggcaa gcaagcgctc gaaacggtgc agcggctgtt gccggtgctg     1620
tgccaggacc atggcctgac tccggaccaa gtggtggcta tcgccagcca cgatggcggc     1680
aagcaagcgc tcgaaacggt gcagcggctg ttgccggtgc tgtgccagga ccatggcctg     1740
actccggacc aagtggtggc tatcgccagc cacgatggcg gcaagcaagc gctcgaaacg     1800
gtgcagcggc tgttgccggt gctgtgccag gaccatggcc tgaccccgga ccaagtggtg     1860
gctatcgcca gcaacaatgg cggcaagcaa gcgctcgaaa cggtgcagcg gctgttgccg     1920
gtgctgtgcc aggaccatgg cctgaccccg gaccaagtgg tggctatcgc cagcaacggt     1980
ggcggcaagc aagcgctcga aagcattgtg gcccagctga gccggcctga tccggcgttg     2040
gccgcgttga ccaacgacca cctcgtcgcc ttggcctgcc tcggcggacg tcctgccatg     2100
gatgcagtga aaagggatt gccgcacgcg ccggaattga tcagaagagt caatcgccgt      2160
attggcgaac gcacgtccca tcgcgttgcc ggatcccagc tggtgaagtc cgagctggaa     2220
gaaaaaaaga gcgagctgcg ccacaagctc aagtacgtgc ccacgagta catcgagctg      2280 atcgagatcg cccgcaacag cacccaagac cgcatcctgg agatgaaagt gatggagttc     2340
ttcatgaagg tgtacggcta ccgcggcaag cacctgggcg gctcccgcaa gcccgatggc     2400
gccatctaca ccgtgggctc ccccatcgac tatggcgtca ttgtcgacac caaggcctac     2460
```

```
tccggcggct acaacttacc catcggtcag gccgacgaga tgcaacgcta cgtgaaggag    2520
aaccagaccc gcaataagca cattaatccc aacgagtggt ggaaggtgta ccccctcctcc  2580 gtgaccgagt tcaaattcct gttcgtgtcc ggccacttca agggcaatta taaggcccaa   2640
ctgacccgcc tgaaccacaa gaccaactgc aacggcgccg tgctgtccgt ggaggaactg   2700
ctgatcggcg gcgagatgat caaggctggt accctgaccc tggaagaggt gcgccgcaag   2760
ttcaacaatg gtgaaatcaa tttcaggtcc ggcggcggag agggcagagg aagtcttcta   2820
acatgcggtg acgtggagga gaatcccggc cctaggatgg actacaaaga ccatgacggt   2880
gattataaag atcatgacat cgattacaag gatgacgatg acaagatggc ccccaagaag   2940
aagaggaagg tgggcattca cggggtgccg gctagcatgg tggatctacg cacgctcggc   3000
tacagtcagc agcagcaaga gaagatcaaa ccgaaggtgc gttcgacagt ggcgcagcac   3060
cacgaggcac tggtgggcca tgggtttaca cacgcgcaca tcgttgcgct cagccaacac   3120
ccggcagcgt tagggaccgt cgctgtcacg tatcagcaca taatcacggc gttgccagag   3180
gcgacacacg aagacatcgt tggcgtcggc aaacagtggt ccggcgcacg cgccctggag   3240
gccttgctca cggatgcggg ggagttgaga ggtccgccgt tacagttgga cacaggccaa   3300
cttgtgaaga ttgcaaaacg tggcggcgtg accgcaatgg aggcagtgca tgcatcgcgc   3360
aatgcactga cgggtgcccc cctgaacctg accccggacc aagtggtggc tatcgccagc   3420
aacaagggcg gcaagcaagc gctcgaaacg gtgcagcggc tgttgccggt gctgtgccag   3480
gaccatggcc tgaccccgga ccaagtggtg gctatcgcca gcaacaaggg cggcaagcaa   3540
gcgctcgaaa cggtgcagcg gctgttgccg gtgctgtgcc aggaccatgg cctgaccccg   3600
gaccaagtgg tggctatcgc cagcaacaag ggcggcaagc aagcgctcga aacggtgcag   3660
cggctgttgc cggtgctgtg ccaggaccat ggcctgaccc cggaccaagt ggtggctatc   3720
gccagcaaca ttggcggcaa gcaagcgctc gaaacggtgc agcggctgtt gccggtgctg   3780
tgccaggacc atggcctgac cccggaccaa gtggtggcta tcgccagcaa caagggcggc   3840
aagcaagcgc tcgaaacggt gcagcggctg ttgccggtgc tgtgccagga ccatggcctg   3900
accccggacc aagtggtggc tatcgccagc aacattggcg gcaagcaagc gctcgaaacg   3960
gtgcagcggc tgttgccggt gctgtgccag gaccatggcc tgaccccgga ccaagtggtg   4020
gctatcgcca gcaacggtgg cggcaagcaa gcgctcgaaa cggtgcagcg gctgttgccg   4080
gtgctgtgcc aggaccatgg cctgaccccg gaccaagtgg tggctatcgc cagcaacaag   4140
ggcggcaagc aagcgctcga aacggtgcag cggctgttgc cggtgctgtg ccaggaccat   4200
ggcctgactc cggaccaagt ggtggctatc gccagccacg atggcggcaa gcaagcgctc   4260
gaaacggtgc agcggctgtt gccggtgctg tgccaggacc atggcctgac cccggaccaa   4320
gtggtggcta tcgccagcaa cattggcggc aagcaagcgc tcgaaacggt gcagcggctg   4380
ttgccggtgc tgtgccagga ccatggcctg accccggacc aagtggtggc tatcgccagc   4440
aacggtggcg gcaagcaagc gctcgaaacg gtgcagcggc tgttgccggt gctgtgccag   4500
gaccatggcc tgaccccgga ccaagtggtg gctatcgcca gcaacattgg cggcaagcaa   4560
gcgctcgaaa cggtgcagcg gctgttgccg gtgctgtgcc aggaccatgg cctgaccccg   4620
gaccaagtgg tggctatcgc cagcaacggt ggcggcaagc aagcgctcga aacggtgcag   4680
cggctgttgc cggtgctgtg ccaggaccat ggcctgactc cggaccaagt ggtggctatc   4740
gccagccacg atggcggcaa gcaagcgctc gaaacggtgc agcggctgtt gccggtgctg   4800
tgccaggacc atggcctgac tccggaccaa gtggtggcta tcgccagcca cgatggcggc   4860
```

-continued

```
aagcaagcgc tcgaaacggt gcagcggctg ttgccggtgc tgtgccagga ccatggcctg      4920
actccggacc aagtggtggc tatcgccagc cacgatggcg gcaagcaagc gctcgaaacg      4980
gtgcagcggc tgttgccggt gctgtgccag gaccatggcc tgaccccgga ccaagtggtg      5040
gctatcgcca gcaacaaggg cggcaagcaa gcgctcgaaa gcattgtggc ccagctgagc      5100
cggcctgatc cggcgttggc cgcgttgacc aacgaccacc tcgtcgcctt ggcctgcctc      5160
ggcggacgtc ctgccatgga tgcagtgaaa aagggattgc cgcacgcgcc ggaattgatc      5220
agaagagtca atcgccgtat tggcgaacgc acgtcccatc gcgttgccag atctcaacta      5280
gtcaaaagtg aactggagga gaagaaatct gaacttcgtc ataaattgaa atatgtgcct      5340
catgaatata ttgaattaat tgaaattgcc agaaattcca ctcaggatag aattcttgaa      5400
atgaaggtaa tggaatttt tatgaaagtt tatggatata gaggtaaaca tttgggtgga      5460
tcaaggaaac cggacggagc aatttatact gtcggatctc ctattgatta cggtgtgatc      5520
gtggatacta aagcttatag cggaggttat aatctgccaa ttggccaagc agatgaaatg      5580
gagcgatatg tcgaagaaaa tcaaacacga acaaacatc tcaaccctaa tgaatggtgg      5640
aaagtctatc catcttctgt aacggaattt aagttttat ttgtgagtgg tcactttaaa      5700
ggaaactaca agctcagct tacacgatta atcatatca ctaattgtaa tggagctgtt      5760
cttagtgtag aagagctttt aattggtgga gaaatgatta agccggcac attaaccta      5820 gaggaagtga gacggaaatt taataacggc gagataaact tttaatag                  5868
```

<210> SEQ ID NO 12
<211> LENGTH: 1954
<212> TYPE: PRT
<213> ORGANISM: Triticum aestivum

<400> SEQUENCE: 12

```
Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Thr Tyr Gln His Ile Ile Thr
    50                  55                  60

Ala Leu Pro Glu Ala Thr His Glu Asp Ile Val Gly Val Gly Lys Gln
65                  70                  75                  80

Trp Ser Gly Ala Arg Ala Leu Glu Ala Leu Thr Asp Ala Gly Glu
                85                  90                  95

Leu Arg Gly Pro Pro Leu Gln Leu Asp Thr Gly Gln Leu Val Lys Ile
            100                 105                 110

Ala Lys Arg Gly Gly Val Thr Ala Met Glu Ala Val His Ala Ser Arg
        115                 120                 125

Asn Ala Leu Thr Gly Ala Pro Leu Asn Leu Thr Pro Asp Gln Val Val
    130                 135                 140

Ala Ile Ala Ser His Asp Gly Gly Lys Gln Ala Leu Glu Thr Val Gln
145                 150                 155                 160

Arg Leu Leu Pro Val Leu Cys Gln Asp His Gly Leu Thr Pro Asp Gln
                165                 170                 175

Val Val Ala Ile Ala Ser Asn Asn Gly Gly Lys Gln Ala Leu Glu Thr
            180                 185                 190
```

```
Val Gln Arg Leu Leu Pro Val Leu Cys Gln Asp His Gly Leu Thr Pro
            195                 200                 205

Asp Gln Val Val Ala Ile Ala Ser His Asp Gly Gly Lys Gln Ala Leu
210                 215                 220

Glu Thr Val Gln Arg Leu Leu Pro Val Leu Cys Gln Asp His Gly Leu
225                 230                 235                 240

Thr Pro Asp Gln Val Val Ala Ile Ala Ser Asn Gly Gly Lys Gln
            245                 250                 255

Ala Leu Glu Thr Val Gln Arg Leu Leu Pro Val Leu Cys Gln Asp His
            260                 265                 270

Gly Leu Thr Pro Asp Gln Val Val Ala Ile Ala Ser Asn Asn Gly Gly
            275                 280                 285

Lys Gln Ala Leu Glu Thr Val Gln Arg Leu Leu Pro Val Leu Cys Gln
290                 295                 300

Asp His Gly Leu Thr Pro Asp Gln Val Val Ala Ile Ala Ser His Asp
305                 310                 315                 320

Gly Gly Lys Gln Ala Leu Glu Thr Val Gln Arg Leu Leu Pro Val Leu
            325                 330                 335

Cys Gln Asp His Gly Leu Thr Pro Asp Gln Val Val Ala Ile Ala Ser
            340                 345                 350

Asn Gly Gly Gly Lys Gln Ala Leu Glu Thr Val Gln Arg Leu Leu Pro
            355                 360                 365

Val Leu Cys Gln Asp His Gly Leu Thr Pro Asp Gln Val Val Ala Ile
            370                 375                 380

Ala Ser Asn Asn Gly Gly Lys Gln Ala Leu Glu Thr Val Gln Arg Leu
385                 390                 395                 400

Leu Pro Val Leu Cys Gln Asp His Gly Leu Thr Pro Asp Gln Val Val
            405                 410                 415

Ala Ile Ala Ser His Asp Gly Gly Lys Gln Ala Leu Glu Thr Val Gln
            420                 425                 430

Arg Leu Leu Pro Val Leu Cys Gln Asp His Gly Leu Thr Pro Asp Gln
            435                 440                 445

Val Val Ala Ile Ala Ser Asn Gly Gly Gly Lys Gln Ala Leu Glu Thr
450                 455                 460

Val Gln Arg Leu Leu Pro Val Leu Cys Gln Asp His Gly Leu Thr Pro
465                 470                 475                 480

Asp Gln Val Val Ala Ile Ala Ser His Asp Gly Gly Lys Gln Ala Leu
            485                 490                 495

Glu Thr Val Gln Arg Leu Leu Pro Val Leu Cys Gln Asp His Gly Leu
            500                 505                 510

Thr Pro Asp Gln Val Val Ala Ile Ala Ser Asn Asn Gly Gly Lys Gln
            515                 520                 525

Ala Leu Glu Thr Val Gln Arg Leu Leu Pro Val Leu Cys Gln Asp His
            530                 535                 540

Gly Leu Thr Pro Asp Gln Val Val Ala Ile Ala Ser His Asp Gly Gly
545                 550                 555                 560

Lys Gln Ala Leu Glu Thr Val Gln Arg Leu Leu Pro Val Leu Cys Gln
            565                 570                 575

Asp His Gly Leu Thr Pro Asp Gln Val Val Ala Ile Ala Ser His Asp
            580                 585                 590

Gly Gly Lys Gln Ala Leu Glu Thr Val Gln Arg Leu Leu Pro Val Leu
            595                 600                 605

Cys Gln Asp His Gly Leu Thr Pro Asp Gln Val Val Ala Ile Ala Ser
```

-continued

```
            610                 615                 620
Asn Asn Gly Gly Lys Gln Ala Leu Glu Thr Val Gln Arg Leu Leu Pro
625                 630                 635                 640

Val Leu Cys Gln Asp His Gly Leu Thr Pro Asp Gln Val Val Ala Ile
                645                 650                 655

Ala Ser Asn Gly Gly Lys Gln Ala Leu Glu Ser Ile Val Ala Gln
                660                 665                 670

Leu Ser Arg Pro Asp Pro Ala Leu Ala Ala Leu Thr Asn Asp His Leu
                675                 680                 685

Val Ala Leu Ala Cys Leu Gly Gly Arg Pro Ala Met Asp Ala Val Lys
690                 695                 700

Lys Gly Leu Pro His Ala Pro Glu Leu Ile Arg Arg Val Asn Arg Arg
705                 710                 715                 720

Ile Gly Glu Arg Thr Ser His Arg Val Ala Gly Ser Gln Leu Val Lys
                725                 730                 735

Ser Glu Leu Glu Glu Lys Lys Ser Glu Leu Arg His Lys Leu Lys Tyr
                740                 745                 750

Val Pro His Glu Tyr Ile Glu Leu Ile Glu Ile Ala Arg Asn Ser Thr
                755                 760                 765

Gln Asp Arg Ile Leu Glu Met Lys Val Met Glu Phe Phe Met Lys Val
770                 775                 780

Tyr Gly Tyr Arg Gly Lys His Leu Gly Gly Ser Arg Lys Pro Asp Gly
785                 790                 795                 800

Ala Ile Tyr Thr Val Gly Ser Pro Ile Asp Tyr Gly Val Ile Val Asp
                805                 810                 815

Thr Lys Ala Tyr Ser Gly Gly Tyr Asn Leu Pro Ile Gly Gln Ala Asp
                820                 825                 830

Glu Met Gln Arg Tyr Val Lys Glu Asn Gln Thr Arg Asn Lys His Ile
                835                 840                 845

Asn Pro Asn Glu Trp Trp Lys Val Tyr Pro Ser Ser Val Thr Glu Phe
850                 855                 860

Lys Phe Leu Phe Val Ser Gly His Phe Lys Gly Asn Tyr Lys Ala Gln
865                 870                 875                 880

Leu Thr Arg Leu Asn His Lys Thr Asn Cys Asn Gly Ala Val Leu Ser
                885                 890                 895

Val Glu Glu Leu Leu Ile Gly Gly Glu Met Ile Lys Ala Gly Thr Leu
                900                 905                 910

Thr Leu Glu Glu Val Arg Arg Lys Phe Asn Asn Gly Glu Ile Asn Phe
                915                 920                 925

Arg Ser Gly Gly Gly Glu Gly Arg Gly Ser Leu Leu Thr Cys Gly Asp
930                 935                 940

Val Glu Glu Asn Pro Gly Pro Arg Met Asp Tyr Lys Asp His Asp Gly
945                 950                 955                 960

Asp Tyr Lys Asp His Asp Ile Asp Tyr Lys Asp Asp Asp Asp Lys Met
                965                 970                 975

Ala Pro Lys Lys Lys Arg Lys Val Gly Ile His Gly Val Pro Ala Ser
                980                 985                 990

Met Val Asp Leu Arg Thr Leu Gly  Tyr Ser Gln Gln  Gln Glu Lys
                995                 1000                1005

Ile Lys  Pro Lys Val Arg Ser  Thr Val Ala Gln His  His Glu Ala
    1010                1015                1020

Leu Val  Gly His Gly Phe Thr  His Ala His Ile Val  Ala Leu Ser
    1025                1030                1035
```

```
Gln His Pro Ala Ala Leu Gly Thr Val Ala Val Thr Tyr Gln His
    1040                1045                1050
Ile Ile Thr Ala Leu Pro Glu Ala Thr His Glu Asp Ile Val Gly
    1055                1060                1065
Val Gly Lys Gln Trp Ser Gly Ala Arg Ala Leu Glu Ala Leu Leu
    1070                1075                1080
Thr Asp Ala Gly Glu Leu Arg Gly Pro Pro Leu Gln Leu Asp Thr
    1085                1090                1095
Gly Gln Leu Val Lys Ile Ala Lys Arg Gly Gly Val Thr Ala Met
    1100                1105                1110
Glu Ala Val His Ala Ser Arg Asn Ala Leu Thr Gly Ala Pro Leu
    1115                1120                1125
Asn Leu Thr Pro Asp Gln Val Val Ala Ile Ala Ser Asn Lys Gly
    1130                1135                1140
Gly Lys Gln Ala Leu Glu Thr Val Gln Arg Leu Leu Pro Val Leu
    1145                1150                1155
Cys Gln Asp His Gly Leu Thr Pro Asp Gln Val Ala Ile Ala
    1160                1165                1170
Ser Asn Lys Gly Gly Lys Gln Ala Leu Glu Thr Val Gln Arg Leu
    1175                1180                1185
Leu Pro Val Leu Cys Gln Asp His Gly Leu Thr Pro Asp Gln Val
    1190                1195                1200
Val Ala Ile Ala Ser Asn Lys Gly Gly Lys Gln Ala Leu Glu Thr
    1205                1210                1215
Val Gln Arg Leu Leu Pro Val Leu Cys Gln Asp His Gly Leu Thr
    1220                1225                1230
Pro Asp Gln Val Val Ala Ile Ala Ser Asn Ile Gly Gly Lys Gln
    1235                1240                1245
Ala Leu Glu Thr Val Gln Arg Leu Leu Pro Val Leu Cys Gln Asp
    1250                1255                1260
His Gly Leu Thr Pro Asp Gln Val Val Ala Ile Ala Ser Asn Lys
    1265                1270                1275
Gly Gly Lys Gln Ala Leu Glu Thr Val Gln Arg Leu Leu Pro Val
    1280                1285                1290
Leu Cys Gln Asp His Gly Leu Thr Pro Asp Gln Val Val Ala Ile
    1295                1300                1305
Ala Ser Asn Ile Gly Gly Lys Gln Ala Leu Glu Thr Val Gln Arg
    1310                1315                1320
Leu Leu Pro Val Leu Cys Gln Asp His Gly Leu Thr Pro Asp Gln
    1325                1330                1335
Val Val Ala Ile Ala Ser Asn Gly Gly Gly Lys Gln Ala Leu Glu
    1340                1345                1350
Thr Val Gln Arg Leu Leu Pro Val Leu Cys Gln Asp His Gly Leu
    1355                1360                1365
Thr Pro Asp Gln Val Val Ala Ile Ala Ser Asn Lys Gly Gly Lys
    1370                1375                1380
Gln Ala Leu Glu Thr Val Gln Arg Leu Leu Pro Val Leu Cys Gln
    1385                1390                1395
Asp His Gly Leu Thr Pro Asp Gln Val Val Ala Ile Ala Ser His
    1400                1405                1410
Asp Gly Gly Lys Gln Ala Leu Glu Thr Val Gln Arg Leu Leu Pro
    1415                1420                1425
```

-continued

| | | | | | | | | | | | |
|---|---|---|---|---|---|---|---|---|---|---|---|
| Val | Leu | Cys | Gln | Asp | His | Gly | Leu | Thr | Pro | Asp | Gln | Val | Val | Ala |
| 1430 | | | | | 1435 | | | | | 1440 | |

Val Leu Cys Gln Asp His Gly Leu Thr Pro Asp Gln Val Val Ala
1430                1435                1440

Ile Ala Ser Asn Ile Gly Gly Lys Gln Ala Leu Glu Thr Val Gln
1445                1450                1455

Arg Leu Leu Pro Val Leu Cys Gln Asp His Gly Leu Thr Pro Asp
1460                1465                1470

Gln Val Val Ala Ile Ala Ser Asn Gly Gly Gly Lys Gln Ala Leu
1475                1480                1485

Glu Thr Val Gln Arg Leu Leu Pro Val Leu Cys Gln Asp His Gly
1490                1495                1500

Leu Thr Pro Asp Gln Val Val Ala Ile Ala Ser Asn Ile Gly Gly
1505                1510                1515

Lys Gln Ala Leu Glu Thr Val Gln Arg Leu Leu Pro Val Leu Cys
1520                1525                1530

Gln Asp His Gly Leu Thr Pro Asp Gln Val Val Ala Ile Ala Ser
1535                1540                1545

Asn Gly Gly Gly Lys Gln Ala Leu Glu Thr Val Gln Arg Leu Leu
1550                1555                1560

Pro Val Leu Cys Gln Asp His Gly Leu Thr Pro Asp Gln Val Val
1565                1570                1575

Ala Ile Ala Ser His Asp Gly Gly Lys Gln Ala Leu Glu Thr Val
1580                1585                1590

Gln Arg Leu Leu Pro Val Leu Cys Gln Asp His Gly Leu Thr Pro
1595                1600                1605

Asp Gln Val Val Ala Ile Ala Ser His Asp Gly Gly Lys Gln Ala
1610                1615                1620

Leu Glu Thr Val Gln Arg Leu Leu Pro Val Leu Cys Gln Asp His
1625                1630                1635

Gly Leu Thr Pro Asp Gln Val Val Ala Ile Ala Ser His Asp Gly
1640                1645                1650

Gly Lys Gln Ala Leu Glu Thr Val Gln Arg Leu Leu Pro Val Leu
1655                1660                1665

Cys Gln Asp His Gly Leu Thr Pro Asp Gln Val Val Ala Ile Ala
1670                1675                1680

Ser Asn Lys Gly Gly Lys Gln Ala Leu Glu Ser Ile Val Ala Gln
1685                1690                1695

Leu Ser Arg Pro Asp Pro Ala Leu Ala Ala Leu Thr Asn Asp His
1700                1705                1710

Leu Val Ala Leu Ala Cys Leu Gly Gly Arg Pro Ala Met Asp Ala
1715                1720                1725

Val Lys Lys Gly Leu Pro His Ala Pro Glu Leu Ile Arg Arg Val
1730                1735                1740

Asn Arg Arg Ile Gly Glu Arg Thr Ser His Arg Val Ala Arg Ser
1745                1750                1755

Gln Leu Val Lys Ser Glu Leu Glu Glu Lys Lys Ser Glu Leu Arg
1760                1765                1770

His Lys Leu Lys Tyr Val Pro His Glu Tyr Ile Glu Leu Ile Glu
1775                1780                1785

Ile Ala Arg Asn Ser Thr Gln Asp Arg Ile Leu Glu Met Lys Val
1790                1795                1800

Met Glu Phe Phe Met Lys Val Tyr Gly Tyr Arg Gly Lys His Leu
1805                1810                1815

Gly Gly Ser Arg Lys Pro Asp Gly Ala Ile Tyr Thr Val Gly Ser

```
                    1820                1825                1830
Pro  Ile  Asp  Tyr  Gly  Val  Ile  Val  Asp  Thr  Lys  Ala  Tyr  Ser  Gly
                    1835                1840                1845

Gly  Tyr  Asn  Leu  Pro  Ile  Gly  Gln  Ala  Asp  Glu  Met  Glu  Arg  Tyr
                    1850                1855                1860

Val  Glu  Glu  Asn  Gln  Thr  Arg  Asn  Lys  His  Leu  Asn  Pro  Asn  Glu
     1865                1870                1875

Trp  Trp  Lys  Val  Tyr  Pro  Ser  Ser  Val  Thr  Glu  Phe  Lys  Phe  Leu
     1880                1885                1890

Phe  Val  Ser  Gly  His  Phe  Lys  Gly  Asn  Tyr  Lys  Ala  Gln  Leu  Thr
     1895                1900                1905

Arg  Leu  Asn  His  Ile  Thr  Asn  Cys  Asn  Gly  Ala  Val  Leu  Ser  Val
     1910                1915                1920

Glu  Glu  Leu  Leu  Ile  Gly  Gly  Glu  Met  Ile  Lys  Ala  Gly  Thr  Leu
     1925                1930                1935

Thr  Leu  Glu  Glu  Val  Arg  Arg  Lys  Phe  Asn  Asn  Gly  Glu  Ile  Asn
     1940                1945                1950

Phe
```

<210> SEQ ID NO 13
<211> LENGTH: 53
<212> TYPE: DNA
<213> ORGANISM: Triticum aestivum

<400> SEQUENCE: 13
tcgctgctgc tcgccgtgac gcaggacccc atctccggga tatgcatctc cga    53

<210> SEQ ID NO 14
<211> LENGTH: 53
<212> TYPE: DNA
<213> ORGANISM: Triticum aestivum

<400> SEQUENCE: 14
tcgctgctgc tcgccgtcac gcaggaccca atctccggga tatgcatctc cca    53

<210> SEQ ID NO 15
<211> LENGTH: 53
<212> TYPE: DNA
<213> ORGANISM: Triticum aestivum

<400> SEQUENCE: 15
tcgctgctgc tcgccgtgac gcaggacccc atctccggga tatgcatctc cga    53

<210> SEQ ID NO 16
<211> LENGTH: 53
<212> TYPE: DNA
<213> ORGANISM: Artificial Sequence
<220> FEATURE:
<223> OTHER INFORMATION: Synthetic sequence

<400> SEQUENCE: 16
tcgctgctgc tcgccgtgac gcaggaccca atctccggga tatgcatctc cga    53

<210> SEQ ID NO 17
<211> LENGTH: 23
<212> TYPE: DNA
<213> ORGANISM: Triticum aestivum

<400> SEQUENCE: 17
ccgtcacgca ggacccaatc tcc    23

<210> SEQ ID NO 18
<211> LENGTH: 32
<212> TYPE: DNA
<213> ORGANISM: Artificial Sequence
<220> FEATURE:
<223> OTHER INFORMATION: MLO-A1-F - Primer

<400> SEQUENCE: 18
tggcgctggt cttcgccgtc atgatcatcg tc                                     32

<210> SEQ ID NO 19
<211> LENGTH: 27
<212> TYPE: DNA
<213> ORGANISM: Artificial Sequence
<220> FEATURE:
<223> OTHER INFORMATION: MLO-A1-R - Primer

<400> SEQUENCE: 19
tacgatgagc gccaccttgc ccgggaa                                           27

<210> SEQ ID NO 20
<211> LENGTH: 30
<212> TYPE: DNA
<213> ORGANISM: Artificial Sequence
<220> FEATURE:
<223> OTHER INFORMATION: MLO-B1-F - Primer

<400> SEQUENCE: 20
ataagctcgg ccatgtaagt tccttcccgg                                        30

<210> SEQ ID NO 21
<211> LENGTH: 28
<212> TYPE: DNA
<213> ORGANISM: Artificial Sequence
<220> FEATURE:
<223> OTHER INFORMATION: MLO-B1-R - Primer

<400> SEQUENCE: 21
ccggccggaa tttgtttgtg tttttgtt                                          28

<210> SEQ ID NO 22
<211> LENGTH: 28
<212> TYPE: DNA
<213> ORGANISM: Artificial Sequence
<220> FEATURE:
<223> OTHER INFORMATION: MLO-D1-F  - Primer

<400> SEQUENCE: 22
tggcttcctc tgctcccttg gtgcacct                                          28

<210> SEQ ID NO 23
<211> LENGTH: 30
<212> TYPE: DNA
<213> ORGANISM: Artificial Sequence
<220> FEATURE:
<223> OTHER INFORMATION: MLO-D1-R - Primer

<400> SEQUENCE: 23
tggagctggt gcaagctgcc cgtggacatt                                        30

<210> SEQ ID NO 24
<211> LENGTH: 27
<212> TYPE: DNA
<213> ORGANISM: Artificial Sequence
<220> FEATURE:

<223> OTHER INFORMATION: MLO-F - Primer

<400> SEQUENCE: 24
gtcttcgccg tcatgatcat cgtctcc 27

<210> SEQ ID NO 25
<211> LENGTH: 28
<212> TYPE: DNA
<213> ORGANISM: Artificial Sequence
<220> FEATURE:
<223> OTHER INFORMATION: MLO-R - Primer

<400> SEQUENCE: 25
tggtattcca aggaggcggt ctctgtct 28

<210> SEQ ID NO 26
<211> LENGTH: 23
<212> TYPE: DNA
<213> ORGANISM: Artificial Sequence
<220> FEATURE:
<223> OTHER INFORMATION: Synthetic sequence

<400> SEQUENCE: 26
cttggagatt gggtcctgcg tga 23

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
aaactcacgc aggacccaat ctc 23

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
gtcttcgccg tcatgatcat cgtctcc 27

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ggtgctcagg tagtggttgt c 21

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
ctttgtcgtg aatataaacc agacacgag 29

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
tggtattcca aggaggcggt ctctgtct                                    28

<210> SEQ ID NO 32
<211> LENGTH: 30
<212> TYPE: DNA
<213> ORGANISM: Artificial Sequence
<220> FEATURE:
<223> OTHER INFORMATION: Ubi-F - Primer

<400> SEQUENCE: 32
cagttagaca tggtctaaag gacaattgag                                  30

<210> SEQ ID NO 33
<211> LENGTH: 27
<212> TYPE: DNA
<213> ORGANISM: Artificial Sequence
<220> FEATURE:
<223> OTHER INFORMATION: Ubi-R - Primer

<400> SEQUENCE: 33
ccaaccacac cacatcatca caaccaa                                     27

<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34
ttcgactggt cggtgcgcgg tcacccatc atcatcatca tcac                   44

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tcaccacggg cgagaacaag tt                                          22

<210> SEQ ID NO 36
<211> LENGTH: 44
<212> TYPE: DNA
<213> ORGANISM: Artificial Sequence
<220> FEATURE:
<223> OTHER INFORMATION: Primer

<400> SEQUENCE: 36
cgctgctgct cgccgtcacg cagaacagaa actgatctct gaag                  44

<210> SEQ ID NO 37
<211> LENGTH: 31
<212> TYPE: DNA
<213> ORGANISM: Artificial Sequence
<220> FEATURE:
<223> OTHER INFORMATION: Primer

<400> SEQUENCE: 37
aagacctgcc atctccggga tatgcatctc c                                      31

<210> SEQ ID NO 38
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(10)
<223> OTHER INFORMATION: n is a, c, g, or t

<400> SEQUENCE: 38 ggaccnnnnn                                                              10

<210> SEQ ID NO 39
<211> LENGTH: 1573
<212> TYPE: DNA
<213> ORGANISM: Triticum aestivum

<400> SEQUENCE: 39
atggcggagg acgacgggta cccccccggcg cggacgctgc cggagacgcc gtcctgggcg      60
gtggcgctgg tcttcgccgt catgatcatc gtctccgtcc tcctggagca cgcgctccac     120
aagctcggcc agtggttcca caagcggcac aagaacgcgc tggcggaggc gctggagaag     180
atgaaggcgg agctgatgct ggtgggattc aatctccggg atatgcatct cccagaaggc     240
cgccagcatc atgcgcccct gcaaggtgga acccggttcc gtcaagagca agtacaagga     300
ctactactgc gccaaagagg gcaaggtggc gctcatgtcc acgggcagcc tgcaccagct     360
ccacatattc atcttcgtgc tagccgtctt ccatgtcacc tacagcgtca tcatcatggc     420
tctaagccgt ctcaagatga aacatggaa gaaatgggag acagagaccg cctccttgga     480
ataccagttc gcaaatgatc ctgcgcggtt ccgcttcacg caccagacgt cgttcgtgaa     540
gcggcacctg ggcctgtcca gcacccccgg cgtcagatgg gtggtggcct tcttcaggca     600
gttcttcagg tcggtcacca aggtggacta cctcaccttg agggcaggct tcatcaacgc     660
gcacttgtcg cagaacagca agttcgactt ccacaagtac atcaagaggt ccatggagga     720
cgacttcaaa gtcgtcgttg gcatcagcct cccgctgtgg gctgtggcga tcctcacccct    780 cttccttgat atcgacggga tcggcacact cacctgggtt tctttcatcc ctctcatcat     840
cctcttgtgt gttggaacca agctagagat gatcatcatg gagatggccc tggagatcca     900
ggaccggtcg agcgtcatca aggggggcacc cgtggtcgag cccagcaaca agttcttctg     960
gttccaccgc cccgactggg tcctcttctt catacacctg acgctgttcc agaacgcgtt    1020
tcagatggca catttcgtgt ggacagtggc cacgcccggc ttgaaggact gcttccatat    1080
gaacatcggg ctgagcatca tgaaggtcgt gctggggctg gctctccagt tcctgtgcag    1140
ctacatcacc ttccccctct acgcgctagt cacacagatg ggatcaaaca tgaagaggtc    1200
catcttcgac gagcagacag ccaaggcgct gaccaactgg cggaacacgg ccaaggagaa    1260
gaagaaggtc cgagacacgg acatgctgat ggcgcagatg atcggcgacg caacacccag    1320
ccgaggcacg tccccgatgc ctagccgggg ctcatcgccg gtgcacctgc ttcagaaggg    1380
catgggacgg tctgacgatc cccagagcgc accgacctcg ccaaggacca tggaggaggc    1440
tagggacatg tacccggttg tggtggcgca tcctgtacac agactaaatc ctgctgacag    1500
gagaaggtcg gtctcttcat cagccctcga tgccgacatc cccagcgcag attttttcctt    1560 cagccaggga tga                                                          1573

<210> SEQ ID NO 40
<211> LENGTH: 1746
<212> TYPE: DNA
<213> ORGANISM: Triticum aestivum

<400> SEQUENCE: 40

```
atggcggagg acgacgggta ccccccagcg aggacgctgc cggagacgcc gtcctgggcg      60
gtggccctcg tcttcgccgt catgatcatc gtgtccgtcc tcctggagca cgcgctccat     120
aagctcggcc agtggttcca caagcggcac aagaacgcgc tggcggaggc gctggagaag     180
atcaaggcgg agctcatgct ggtgggcttc atctcgctgc tgctcgccgt gacgcaggac     240
gaggcactgg tgggccatgg gtttacacac gcgcacatcg ttgcgctcag ccaacacccg     300
gcagcgttag ggaccgtcgc tgtcacgtat cagcacataa tcacggcgtt gccagaggcg     360
acacacgaag acatcgttgg ccccatctcc gggatatgca tctccgagaa ggccgccagc     420
atcatgcggc cctgcaagct gccccctggc tccgtcaaga gcaagtacaa agactactac     480
tgcgccaaac agggcaaggt gtcgctcatg tccacgggca gcttgcacca gctgcacata     540
ttcatcttcg tgctcgccgt cttccatgtc acctacagcg tcatcatcat ggctctaagc     600
cgtctcaaga tgagaacctg gaagaaatgg gagacagaga ccgcctccct ggaataccag     660
ttcgcaaatg atcctgcgcg gttccgcttc acgcaccaga cgtcgttcgt gaagcggcac     720
ctgggcctct ccagcacccc cggcgtcaga tgggtggtgg ccttcttcag gcagttcttc     780
aggtcggtca ccaaggtgga ctacctcacc ttgagggcag gcttcatcaa cgcgcatttg     840
tcgcataaca gcaagttcga cttccacaag tacatcaaga ggtccatgga ggacgacttc     900
aaagtcgtcg ttggcatcag cctcccgctg tggtgtgtgg cgatcctcac cctcttcctt     960
gacattgacg ggatcggcac gctcacctgg atttctttca tccctctcgt catcctcttg    1020
tgtgttggaa ccaagctgga gatgatcatc atggagatgg ccctggagat ccaggaccgg    1080
gcgagcgtca tcaaggggc gcccgtggtt gagcccagca acaagttctt ctggttccac    1140
cgccccgact gggtcctctt cttcatacac ctgacgctat tccagaacgc gtttcagatg    1200
gcacatttcg tgtggacagt ggccacgccc ggcttgaaga aatgcttcca tatgcacatc    1260
gggctgagca tcatgaaggt cgtgctgggg ctggctcttc agttcctctg cagctatatc    1320
accttcccgc tctacgcgct cgtcacacag atgggatcaa acatgaagag gtccatcttc    1380
gacgagcaga cggccaaggc gctgacaaac tggcggaaca cggccaagga agaagaagaag    1440
gtccgagaca cggacatgct gatggcgcag atgatcggcg acgcgacgcc cagccgaggg    1500
gcgtcgccca tgcctagccg gggctcgtcg ccagtgcacc tgcttcacaa gggcatggga    1560
cggtccgacg atccccagag cacgccaacc tcgccaaggg ccatggagga ggctagggac    1620
atgtacccgg ttgtggtggc gcatccagtg cacagactaa atcctgctga caggagaagg    1680
tcggtctcgt cgtcggcact cgatgtcgac attcccagcg cagatttttc cttcagccag    1740
ggatga                                                                1746
```

<210> SEQ ID NO 41
<211> LENGTH: 1675
<212> TYPE: DNA
<213> ORGANISM: Triticum aestivum

<400> SEQUENCE: 41

-continued

```
atggcggagg acgacgggta ccccccggcg cggacgctgc cggagacgcc gtcctgggcg    60
gtggcgctcg tcttcgccgt catgatcatc gtgtccgtcc tcctggagca cgcgctccac   120
aagctcggcc agtggttcca caagcggcac aagaacgcgc tggcggaggc gctggagaag   180
atcaaagcgg agctgatgct ggtggggttc atctcgctgc tgctcgccgt gacgcaggag   240
atgcatatcc cggagatggc taaactaact atgcgtgacg gcgagcagca ggagatgcat   300
atcccggaga tggctaaact ggatatgcat ctccgagaag gccgccagca tcatgcggcc   360
ctgcagcctg cccctggtt ccgtcaagag caagtacaaa gactactact gcgccaaaaa    420
gggcaaggtg tcgctaatgt ccacgggcag cttgcaccag ctccacatat tcatcttcgt   480
gctcgccgtc ttccatgtca cctacagcgt catcatcatg gctctaagcc gtctcaagat   540
gaggacatgg aagaaatggg agacagagac cgcctccttg gaataccagt tcgcaaatga   600
tcctgcgcgg ttccgcttca cgcaccagac gtcgttcgtg aagcgtcacc tgggcctctc   660
cagcaccccc ggcatcagat gggtggtggc cttcttcagg cagttcttca ggtcggtcac   720
caaggtggac tacctcaccc tgagggcagg cttcatcaac gcgcatttgt cgcataacag   780
caagttcgac ttccacaagt acatcaagag gtccatggag gacgacttca aagtcgtcgt   840
tggcatcagc ctcccgctgt ggtgtgtggc gatcctcacc ctcttccttg atattgacgg   900
gatcggcacg ctcacctgga tttctttcat ccctctcgtc atcctcttgt gtgttggaac   960
caagctggag atgatcatca tggagatggc cctggagatc caggaccggg cgagcgtcat  1020
caaggggggcg cccgtggttg agcccagcaa caagttcttc tggttccacc gccccgactg  1080
ggtcctcttc ttcatacacc tgacgctgtt ccagaatgcg tttcagatgg cacatttcgt  1140
ctggacagtg gccacgcccg gcttgaagaa atgcttccat atgcacatcg ggctgagcat  1200
catgaaggtc gtgctgggc tggctcttca gttcctctgc agctatatca ccttcccgct   1260
ctacgcgctc gtcacacaga tgggatcaaa catgaagagg tccatcttcg acgagcagac  1320
ggccaaggcg ctgacaaact ggcggaacac ggccaaggaa aagaagaagg tccgagacac  1380
ggacatgctg atggcgcaga tgatcggcga cgcgacgccc agccgagggg cgtcgcccat  1440
gcctagccgg ggctcgtcgc cagtgcacct gcttcacaag ggcatgggac ggtccgacga  1500
tccccagagc acgccaacct cgccaagggc catggaggag gctagggaca tgtacccggt  1560
tgtggtggcg catccagtgc acagactaaa tcctgctgac aggagaaggt cggtctcttc  1620
gtcggcactc gatgccgaca tccccagcgc agattttttcc ttcagccagg gatga      1675
```

<210> SEQ ID NO 42
<211> LENGTH: 27
<212> TYPE: DNA
<213> ORGANISM: Artificial Sequence
<220> FEATURE:
<223> OTHER INFORMATION: Synthetic sequence

<400> SEQUENCE: 42

```
ctgatgctgg tgggattcaa tctccgg                                        27
```

<210> SEQ ID NO 43
<211> LENGTH: 28
<212> TYPE: DNA
<213> ORGANISM: Artificial Sequence
<220> FEATURE:
<223> OTHER INFORMATION: Synthetic sequence

<400> SEQUENCE: 43

```
tggtattcca aggaggcggt ctctgtct                                       28
```

```
<210> SEQ ID NO 44
<211> LENGTH: 28
<212> TYPE: DNA
<213> ORGANISM: Artificial Sequence
<220> FEATURE:
<223> OTHER INFORMATION: Synthetic sequence

<400> SEQUENCE: 44
acatcgttgc gctcagccaa cacccggc                                      28

<210> SEQ ID NO 45
<211> LENGTH: 28
<212> TYPE: DNA
<213> ORGANISM: Artificial Sequence
<220> FEATURE:
<223> OTHER INFORMATION: Synthetic sequence

<400> SEQUENCE: 45
tggtattcca aggaggcggt ctctgtct                                      28

<210> SEQ ID NO 46
<211> LENGTH: 29
<212> TYPE: DNA
<213> ORGANISM: Artificial Sequence
<220> FEATURE:
<223> OTHER INFORMATION: Synthetic sequence

<400> SEQUENCE: 46
ctaactatgc gtgacggcga gcagcagga                                     29

<210> SEQ ID NO 47
<211> LENGTH: 28
<212> TYPE: DNA
<213> ORGANISM: Artificial Sequence
<220> FEATURE:
<223> OTHER INFORMATION: Synthetic sequence

<400> SEQUENCE: 47
tggtattcca aggaggcggt ctctgtct                                      28

<210> SEQ ID NO 48
<211> LENGTH: 21
<212> TYPE: DNA
<213> ORGANISM: Artificial Sequence
<220> FEATURE:
<223> OTHER INFORMATION: Synthetic sequence

<400> SEQUENCE: 48
tcgctgctgc tcgccgtcac g                                             21

<210> SEQ ID NO 49
<211> LENGTH: 13
<212> TYPE: DNA
<213> ORGANISM: Artificial Sequence
<220> FEATURE:
<223> OTHER INFORMATION: Synthetic sequence

<400> SEQUENCE: 49
tatgcatctc cca                                                      13

<210> SEQ ID NO 50
<211> LENGTH: 26
<212> TYPE: DNA
<213> ORGANISM: Artificial Sequence
<220> FEATURE:
```

<223> OTHER INFORMATION: Synthetic sequence

<400> SEQUENCE: 50
tcgctgctgc tcgccgtcac gcagga                                    26

<210> SEQ ID NO 51
<211> LENGTH: 24
<212> TYPE: DNA
<213> ORGANISM: Artificial Sequence
<220> FEATURE:
<223> OTHER INFORMATION: Synthetic sequence

<400> SEQUENCE: 51
aatctccggg atatgcatct ccca                                      24

<210> SEQ ID NO 52
<211> LENGTH: 25
<212> TYPE: DNA
<213> ORGANISM: Artificial Sequence
<220> FEATURE:
<223> OTHER INFORMATION: Synthetic sequence

<400> SEQUENCE: 52
caatctccgg gatatgcatc tccca                                     25

<210> SEQ ID NO 53
<211> LENGTH: 26
<212> TYPE: DNA
<213> ORGANISM: Artificial Sequence
<220> FEATURE:
<223> OTHER INFORMATION: Synthetic sequence

<400> SEQUENCE: 53
tcgctgctgc tcgccgtgac gcagga                                    26

<210> SEQ ID NO 54
<211> LENGTH: 27
<212> TYPE: DNA
<213> ORGANISM: Artificial Sequence
<220> FEATURE:
<223> OTHER INFORMATION: Synthetic sequence

<400> SEQUENCE: 54
ccccatctcc gggatatgca tctccga                                   27

<210> SEQ ID NO 55
<211> LENGTH: 26
<212> TYPE: DNA
<213> ORGANISM: Artificial Sequence
<220> FEATURE:
<223> OTHER INFORMATION: Synthetic sequence

<400> SEQUENCE: 55
tcgctgctgc tcgccgtgac gcagga                                    26

<210> SEQ ID NO 56
<211> LENGTH: 16
<212> TYPE: DNA
<213> ORGANISM: Artificial Sequence
<220> FEATURE:
<223> OTHER INFORMATION: Synthetic sequence

<400> SEQUENCE: 56
ggatatgcat ctccga                                               16

```
<210> SEQ ID NO 57
<211> LENGTH: 25
<212> TYPE: DNA
<213> ORGANISM: Artificial Sequence
<220> FEATURE:
<223> OTHER INFORMATION: Synthetic sequence

<400> SEQUENCE: 57
tcgctgctgc tcgccgtgac gcagg                                             25

<210> SEQ ID NO 58
<211> LENGTH: 23
<212> TYPE: DNA
<213> ORGANISM: Artificial Sequence
<220> FEATURE:
<223> OTHER INFORMATION: Synthetic sequence

<400> SEQUENCE: 58
atctccggga tatgcatctc cga                                               23

<210> SEQ ID NO 59
<211> LENGTH: 24
<212> TYPE: DNA
<213> ORGANISM: Artificial Sequence
<220> FEATURE:
<223> OTHER INFORMATION: Synthetic sequence

<400> SEQUENCE: 59
tcgctgctgc tcgccgtgac gcag                                              24

<210> SEQ ID NO 60
<211> LENGTH: 24
<212> TYPE: DNA
<213> ORGANISM: Artificial Sequence
<220> FEATURE:
<223> OTHER INFORMATION: Synthetic sequence

<400> SEQUENCE: 60
aatctccggg atatgcatct ccga                                              24

<210> SEQ ID NO 61
<211> LENGTH: 23
<212> TYPE: DNA
<213> ORGANISM: Artificial Sequence
<220> FEATURE:
<223> OTHER INFORMATION: Synthetic sequence

<400> SEQUENCE: 61
tcgctgctgc tcgccgtgac gca                                               23

<210> SEQ ID NO 62
<211> LENGTH: 24
<212> TYPE: DNA
<213> ORGANISM: Artificial Sequence
<220> FEATURE:
<223> OTHER INFORMATION: Synthetic sequence

<400> SEQUENCE: 62
aatctccggg atatgcatct ccga                                              24

<210> SEQ ID NO 63
<211> LENGTH: 26
<212> TYPE: DNA
<213> ORGANISM: Artificial Sequence
<220> FEATURE:
<223> OTHER INFORMATION: Synthetic sequence
```

<400> SEQUENCE: 63
tcgctgctgc tcgccgtcac gcagga                                  26

<210> SEQ ID NO 64
<211> LENGTH: 24
<212> TYPE: DNA
<213> ORGANISM: Artificial Sequence
<220> FEATURE:
<223> OTHER INFORMATION: Synthetic sequence

<400> SEQUENCE: 64
aatctccggg atatgcatct ccca                                    24

<210> SEQ ID NO 65
<211> LENGTH: 26
<212> TYPE: DNA
<213> ORGANISM: Artificial Sequence
<220> FEATURE:
<223> OTHER INFORMATION: Synthetic sequence

<400> SEQUENCE: 65
tcgctgctgc tcgccgtcac gcagga                                  26

<210> SEQ ID NO 66
<211> LENGTH: 23
<212> TYPE: DNA
<213> ORGANISM: Artificial Sequence
<220> FEATURE:
<223> OTHER INFORMATION: Synthetic sequence

<400> SEQUENCE: 66
atctccggga tatgcatctc cca                                     23

<210> SEQ ID NO 67
<211> LENGTH: 27
<212> TYPE: DNA
<213> ORGANISM: Artificial Sequence
<220> FEATURE:
<223> OTHER INFORMATION: Synthetic sequence

<400> SEQUENCE: 67
tcgctgctgc tcgccgtcac gcaggac                                 27

<210> SEQ ID NO 68
<211> LENGTH: 24
<212> TYPE: DNA
<213> ORGANISM: Artificial Sequence
<220> FEATURE:
<223> OTHER INFORMATION: Synthetic sequence

<400> SEQUENCE: 68
aatctccggg atatgcatct ccca                                    24

<210> SEQ ID NO 69
<211> LENGTH: 27
<212> TYPE: DNA
<213> ORGANISM: Artificial Sequence
<220> FEATURE:
<223> OTHER INFORMATION: Synthetic sequence

<400> SEQUENCE: 69
tcgctgctgc tcgccgtgac gcaggac                                 27

<210> SEQ ID NO 70
<211> LENGTH: 24

<212> TYPE: DNA
<213> ORGANISM: Artificial Sequence
<220> FEATURE:
<223> OTHER INFORMATION: Synthetic sequence

<400> SEQUENCE: 70
aatctccggg atatgcatct ccga                                    24

<210> SEQ ID NO 71
<211> LENGTH: 24
<212> TYPE: DNA
<213> ORGANISM: Artificial Sequence
<220> FEATURE:
<223> OTHER INFORMATION: Synthetic sequence

<400> SEQUENCE: 71
tcgctgctgc tcgccgtcac gcag                                    24

<210> SEQ ID NO 72
<211> LENGTH: 22
<212> TYPE: DNA
<213> ORGANISM: Artificial Sequence
<220> FEATURE:
<223> OTHER INFORMATION: Synthetic sequence

<400> SEQUENCE: 72
tctccgggat atgcatctcc ca                                      22

<210> SEQ ID NO 73
<211> LENGTH: 25
<212> TYPE: DNA
<213> ORGANISM: Artificial Sequence
<220> FEATURE:
<223> OTHER INFORMATION: Synthetic sequence

<400> SEQUENCE: 73
tcgctgctgc tcgccgtcac gcagg                                   25

<210> SEQ ID NO 74
<211> LENGTH: 25
<212> TYPE: DNA
<213> ORGANISM: Artificial Sequence
<220> FEATURE:
<223> OTHER INFORMATION: Synthetic sequence

<400> SEQUENCE: 74
caatctccgg gatatgcatc tccca                                   25

<210> SEQ ID NO 75
<211> LENGTH: 25
<212> TYPE: DNA
<213> ORGANISM: Artificial Sequence
<220> FEATURE:
<223> OTHER INFORMATION: Synthetic sequence

<400> SEQUENCE: 75
tcgctgctgc tcgccgtgac gcagg                                   25

<210> SEQ ID NO 76
<211> LENGTH: 26
<212> TYPE: DNA
<213> ORGANISM: Artificial Sequence
<220> FEATURE:
<223> OTHER INFORMATION: Synthetic sequence

<400> SEQUENCE: 76

```
cccatctccg ggatatgcat ctccga                                              26

<210> SEQ ID NO 77
<211> LENGTH: 21
<212> TYPE: DNA
<213> ORGANISM: Artificial Sequence
<220> FEATURE:
<223> OTHER INFORMATION: Synthetic sequence

<400> SEQUENCE: 77
tcgctgctgc tcgccgtcac g                                                   21

<210> SEQ ID NO 78
<211> LENGTH: 22
<212> TYPE: DNA
<213> ORGANISM: Artificial Sequence
<220> FEATURE:
<223> OTHER INFORMATION: Synthetic sequence

<400> SEQUENCE: 78
tctccgggat atgcatctcc ca                                                  22

<210> SEQ ID NO 79
<211> LENGTH: 27
<212> TYPE: DNA
<213> ORGANISM: Artificial Sequence
<220> FEATURE:
<223> OTHER INFORMATION: Synthetic sequence

<400> SEQUENCE: 79
tcgctgctgc tcgccgtgac gcaggac                                             27

<210> SEQ ID NO 80
<211> LENGTH: 21
<212> TYPE: DNA
<213> ORGANISM: Artificial Sequence
<220> FEATURE:
<223> OTHER INFORMATION: Synthetic sequence

<400> SEQUENCE: 80
ctccgggata tgcatctccg a                                                   21

<210> SEQ ID NO 81
<211> LENGTH: 27
<212> TYPE: DNA
<213> ORGANISM: Artificial Sequence
<220> FEATURE:
<223> OTHER INFORMATION: Synthetic sequence

<400> SEQUENCE: 81
tcgctgctgc tcgccgtgac gcaggac                                             27

<210> SEQ ID NO 82
<211> LENGTH: 22
<212> TYPE: DNA
<213> ORGANISM: Artificial Sequence
<220> FEATURE:
<223> OTHER INFORMATION: Synthetic sequence

<400> SEQUENCE: 82
tctccgggat atgcatctcc ga                                                  22

<210> SEQ ID NO 83
<211> LENGTH: 27
<212> TYPE: DNA
<213> ORGANISM: Artificial Sequence
```

```
<220> FEATURE:
<223> OTHER INFORMATION: Synthetic sequence

<400> SEQUENCE: 83
tcgctgctgc tcgccgtgac gcaggac                                    27

<210> SEQ ID NO 84
<211> LENGTH: 24
<212> TYPE: DNA
<213> ORGANISM: Artificial Sequence
<220> FEATURE:
<223> OTHER INFORMATION: Synthetic sequence

<400> SEQUENCE: 84
aatctccggg atatgcatct ccga                                       24

<210> SEQ ID NO 85
<211> LENGTH: 21
<212> TYPE: DNA
<213> ORGANISM: Artificial Sequence
<220> FEATURE:
<223> OTHER INFORMATION: Synthetic sequence

<400> SEQUENCE: 85
tcgctgctgc tcgccgtcac g                                          21

<210> SEQ ID NO 86
<211> LENGTH: 21
<212> TYPE: DNA
<213> ORGANISM: Artificial Sequence
<220> FEATURE:
<223> OTHER INFORMATION: Synthetic sequence

<400> SEQUENCE: 86
ctccgggata tgcatctccc a                                          21

<210> SEQ ID NO 87
<211> LENGTH: 21
<212> TYPE: DNA
<213> ORGANISM: Artificial Sequence
<220> FEATURE:
<223> OTHER INFORMATION: Synthetic sequence

<400> SEQUENCE: 87
tcgctgctgc tcgccgtcac g                                          21

<210> SEQ ID NO 88
<211> LENGTH: 29
<212> TYPE: DNA
<213> ORGANISM: Artificial Sequence
<220> FEATURE:
<223> OTHER INFORMATION: Synthetic sequence

<400> SEQUENCE: 88
gacccaatct ccgggatatg catctccca                                  29

<210> SEQ ID NO 89
<211> LENGTH: 12
<212> TYPE: DNA
<213> ORGANISM: Artificial Sequence
<220> FEATURE:
<223> OTHER INFORMATION: Synthetic sequence

<400> SEQUENCE: 89
tcgctgctgc tc                                                    12
```

<210> SEQ ID NO 90
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: n is a, c, g, or t

<400> SEQUENCE: 90 catctccgan                                                          10

<210> SEQ ID NO 91
<211> LENGTH: 22
<212> TYPE: DNA
<213> ORGANISM: Artificial Sequence
<220> FEATURE:
<223> OTHER INFORMATION: Synthetic sequence

<400> SEQUENCE: 91
tcgctgccgc tcgccgtcac gc                                            22

<210> SEQ ID NO 92
<211> LENGTH: 23
<212> TYPE: DNA
<213> ORGANISM: Artificial Sequence
<220> FEATURE:
<223> OTHER INFORMATION: Synthetic sequence

<400> SEQUENCE: 92
atctccggga tatgcatctc cca                                           23

<210> SEQ ID NO 93
<211> LENGTH: 26
<212> TYPE: DNA
<213> ORGANISM: Artificial Sequence
<220> FEATURE:
<223> OTHER INFORMATION: Synthetic sequence

<400> SEQUENCE: 93
tcgctgccgc tcgccgtcac gcagga                                        26

<210> SEQ ID NO 94
<211> LENGTH: 21
<212> TYPE: DNA
<213> ORGANISM: Artificial Sequence
<220> FEATURE:
<223> OTHER INFORMATION: Synthetic sequence

<400> SEQUENCE: 94
ctccgggata tgcatctccc a                                             21

<210> SEQ ID NO 95
<211> LENGTH: 22
<212> TYPE: DNA
<213> ORGANISM: Artificial Sequence
<220> FEATURE:
<223> OTHER INFORMATION: Synthetic sequence

<400> SEQUENCE: 95
tcgctgccgc tcgccgtcac gc                                            22

<210> SEQ ID NO 96
<211> LENGTH: 24

<212> TYPE: DNA
<213> ORGANISM: Artificial Sequence
<220> FEATURE:
<223> OTHER INFORMATION: Synthetic sequence

<400> SEQUENCE: 96
aatctccggg atatgcatct ccca                                          24

<210> SEQ ID NO 97
<211> LENGTH: 23
<212> TYPE: DNA
<213> ORGANISM: Artificial Sequence
<220> FEATURE:
<223> OTHER INFORMATION: Synthetic sequence

<400> SEQUENCE: 97
tcgctgccgc tcgccgtcac gca                                           23

<210> SEQ ID NO 98
<211> LENGTH: 19
<212> TYPE: DNA
<213> ORGANISM: Artificial Sequence
<220> FEATURE:
<223> OTHER INFORMATION: Synthetic sequence

<400> SEQUENCE: 98
ccgggatatg catctccca                                                19

<210> SEQ ID NO 99
<211> LENGTH: 82
<212> TYPE: DNA
<213> ORGANISM: Artificial Sequence
<220> FEATURE:
<223> OTHER INFORMATION: Synthetic sequence

<400> SEQUENCE: 99
tcgctgctgc tcgccgtgac gcaggacccc atctccggga tatgcatctc cgaaagcttg   60
tcgacggatc catggtgagc aa                                            82

<210> SEQ ID NO 100
<211> LENGTH: 23
<212> TYPE: DNA
<213> ORGANISM: Artificial Sequence
<220> FEATURE:
<223> OTHER INFORMATION: Synthetic sequence

<400> SEQUENCE: 100
tcgctgctgc tcgccgtcac gca                                           23

<210> SEQ ID NO 101
<211> LENGTH: 53
<212> TYPE: DNA
<213> ORGANISM: Artificial Sequence
<220> FEATURE:
<223> OTHER INFORMATION: Synthetic sequence

<400> SEQUENCE: 101
catctccggg atatgcatct ccgaaagctt gtcgacggat ccatggtgag caa           53

<210> SEQ ID NO 102
<211> LENGTH: 26
<212> TYPE: DNA
<213> ORGANISM: Artificial Sequence
<220> FEATURE:
<223> OTHER INFORMATION: Synthetic sequence

<400> SEQUENCE: 102
tcgctgctgc tcgccgtcac gcagga    26

<210> SEQ ID NO 103
<211> LENGTH: 54
<212> TYPE: DNA
<213> ORGANISM: Artificial Sequence
<220> FEATURE:
<223> OTHER INFORMATION: Synthetic sequence

<400> SEQUENCE: 103
ccatctccgg gatatgcatc tccgaaagct tgtcgacgga tccatggtga gcaa    54

<210> SEQ ID NO 104
<211> LENGTH: 23
<212> TYPE: DNA
<213> ORGANISM: Artificial Sequence
<220> FEATURE:
<223> OTHER INFORMATION: Synthetic sequence

<400> SEQUENCE: 104
tcgctgctgc tcgccgtcac gca    23

<210> SEQ ID NO 105
<211> LENGTH: 51
<212> TYPE: DNA
<213> ORGANISM: Artificial Sequence
<220> FEATURE:
<223> OTHER INFORMATION: Synthetic sequence

<400> SEQUENCE: 105
tctccgggat atgcatctcc gaaagcttgt cgacggatcc atggtgagca a    51

<210> SEQ ID NO 106
<211> LENGTH: 22
<212> TYPE: DNA
<213> ORGANISM: Artificial Sequence
<220> FEATURE:
<223> OTHER INFORMATION: Synthetic sequence

<400> SEQUENCE: 106
tcgctgctgc tcgccgtcac gc    22

<210> SEQ ID NO 107
<211> LENGTH: 52
<212> TYPE: DNA
<213> ORGANISM: Artificial Sequence
<220> FEATURE:
<223> OTHER INFORMATION: Synthetic sequence

<400> SEQUENCE: 107
atctccggga tatgcatctc cgaaagcttg tcgacggatc catggtgagc aa    52

<210> SEQ ID NO 108
<211> LENGTH: 19
<212> TYPE: DNA
<213> ORGANISM: Artificial Sequence
<220> FEATURE:
<223> OTHER INFORMATION: Synthetic sequence

<400> SEQUENCE: 108
tcgctgctgc tcgccgtga    19

<210> SEQ ID NO 109
<211> LENGTH: 63

```
<212> TYPE: DNA
<213> ORGANISM: Artificial Sequence
<220> FEATURE:
<223> OTHER INFORMATION: Synthetic sequence

<400> SEQUENCE: 109
cgcaggaccc catctccggg atatgcatct ccgaaagctt gtcgacggat ccatggtgag     60
caa                                                                   63

<210> SEQ ID NO 110
<211> LENGTH: 53
<212> TYPE: DNA
<213> ORGANISM: Artificial Sequence
<220> FEATURE:
<223> OTHER INFORMATION: Synthetic sequence

<400> SEQUENCE: 110
cctcacaccg gtgacgggga tcgcatgcga ttcgctgctg ctcgccgtga cgc           53

<210> SEQ ID NO 111
<211> LENGTH: 29
<212> TYPE: DNA
<213> ORGANISM: Artificial Sequence
<220> FEATURE:
<223> OTHER INFORMATION: Synthetic sequence

<400> SEQUENCE: 111
gaccccatct ccgggatatg catctccga                                       29

<210> SEQ ID NO 112
<211> LENGTH: 52
<212> TYPE: DNA
<213> ORGANISM: Artificial Sequence
<220> FEATURE:
<223> OTHER INFORMATION: Synthetic sequence

<400> SEQUENCE: 112
cctcacaccg gtgacgggga tcgcatgcga ttcgctgctg ctcgccgtga cg            52

<210> SEQ ID NO 113
<211> LENGTH: 28
<212> TYPE: DNA
<213> ORGANISM: Artificial Sequence
<220> FEATURE:
<223> OTHER INFORMATION: Synthetic sequence

<400> SEQUENCE: 113
acccaatctc cgggatatgc atctccca                                        28

<210> SEQ ID NO 114
<211> LENGTH: 53
<212> TYPE: DNA
<213> ORGANISM: Artificial Sequence
<220> FEATURE:
<223> OTHER INFORMATION: Synthetic sequence

<400> SEQUENCE: 114
cctcacaccg gtgacgggga tcgcatgcga ttcgctgctg ctcgccgtga cgc           53

<210> SEQ ID NO 115
<211> LENGTH: 22
<212> TYPE: DNA
<213> ORGANISM: Artificial Sequence
<220> FEATURE:
<223> OTHER INFORMATION: Synthetic sequence
```

```
<400> SEQUENCE: 115
tctccgggat atgcatctcc ga                                         22

<210> SEQ ID NO 116
<211> LENGTH: 58
<212> TYPE: DNA
<213> ORGANISM: Artificial Sequence
<220> FEATURE:
<223> OTHER INFORMATION: Synthetic sequence

<400> SEQUENCE: 116
cctcacaccg gtgacgggga tcgcatgcga ttcgctgctg ctcgccgtga cgcaggac  58

<210> SEQ ID NO 117
<211> LENGTH: 23
<212> TYPE: DNA
<213> ORGANISM: Artificial Sequence
<220> FEATURE:
<223> OTHER INFORMATION: Synthetic sequence

<400> SEQUENCE: 117
atctccggga tatgcatctc cga                                        23

<210> SEQ ID NO 118
<211> LENGTH: 55
<212> TYPE: DNA
<213> ORGANISM: Artificial Sequence
<220> FEATURE:
<223> OTHER INFORMATION: Synthetic sequence

<400> SEQUENCE: 118
cctcacaccg gtgacgggga tcgcatgcga ttcgctgctg ctcgccgtga cgcag     55

<210> SEQ ID NO 119
<211> LENGTH: 26
<212> TYPE: DNA
<213> ORGANISM: Artificial Sequence
<220> FEATURE:
<223> OTHER INFORMATION: Synthetic sequence

<400> SEQUENCE: 119
ccaatctccg ggatatgcat ctccca                                     26

<210> SEQ ID NO 120
<211> LENGTH: 53
<212> TYPE: DNA
<213> ORGANISM: Artificial Sequence
<220> FEATURE:
<223> OTHER INFORMATION: Synthetic sequence

<400> SEQUENCE: 120
tcgctgctgc tcgccgtcac gcaggaccca atctccggga tatgcatctc cca       53

<210> SEQ ID NO 121
<211> LENGTH: 25
<212> TYPE: DNA
<213> ORGANISM: Artificial Sequence
<220> FEATURE:
<223> OTHER INFORMATION: Synthetic sequence

<400> SEQUENCE: 121
tcgctgctgc tcgccgtcac gcagg                                      25

<210> SEQ ID NO 122
<211> LENGTH: 24
```

```
<212> TYPE: DNA
<213> ORGANISM: Artificial Sequence
<220> FEATURE:
<223> OTHER INFORMATION: Synthetic sequence

<400> SEQUENCE: 122
aatctccggg atatgcatct ccca                                           24

<210> SEQ ID NO 123
<211> LENGTH: 26
<212> TYPE: DNA
<213> ORGANISM: Artificial Sequence
<220> FEATURE:
<223> OTHER INFORMATION: Synthetic sequence

<400> SEQUENCE: 123
tcgctgctgc tcgccgtcac gcagga                                         26

<210> SEQ ID NO 124
<211> LENGTH: 24
<212> TYPE: DNA
<213> ORGANISM: Artificial Sequence
<220> FEATURE:
<223> OTHER INFORMATION: Synthetic sequence

<400> SEQUENCE: 124
aatctccggg atatgcatct ccca                                           24

<210> SEQ ID NO 125
<211> LENGTH: 27
<212> TYPE: DNA
<213> ORGANISM: Artificial Sequence
<220> FEATURE:
<223> OTHER INFORMATION: Synthetic sequence

<400> SEQUENCE: 125
tcgctgctgc tcgccgtcac gcagacc                                        27

<210> SEQ ID NO 126
<211> LENGTH: 25
<212> TYPE: DNA
<213> ORGANISM: Artificial Sequence
<220> FEATURE:
<223> OTHER INFORMATION: Synthetic sequence

<400> SEQUENCE: 126
caatctccgg gatatgcatc tccca                                          25

<210> SEQ ID NO 127
<211> LENGTH: 26
<212> TYPE: DNA
<213> ORGANISM: Artificial Sequence
<220> FEATURE:
<223> OTHER INFORMATION: Synthetic sequence

<400> SEQUENCE: 127
tcgctgctgc tcgccgtcac gcagga                                         26

<210> SEQ ID NO 128
<211> LENGTH: 24
<212> TYPE: DNA
<213> ORGANISM: Artificial Sequence
<220> FEATURE:
<223> OTHER INFORMATION: Synthetic sequence

<400> SEQUENCE: 128
```

```
aatctccggg atatgcatct ccca                                           24

<210> SEQ ID NO 129
<211> LENGTH: 24
<212> TYPE: DNA
<213> ORGANISM: Artificial Sequence
<220> FEATURE:
<223> OTHER INFORMATION: Synthetic sequence

<400> SEQUENCE: 129
tcgctgctgc tcgccgtcac gcag                                           24

<210> SEQ ID NO 130
<211> LENGTH: 25
<212> TYPE: DNA
<213> ORGANISM: Artificial Sequence
<220> FEATURE:
<223> OTHER INFORMATION: Synthetic sequence

<400> SEQUENCE: 130
caatctccgg gatatgcatc tccca                                          25

<210> SEQ ID NO 131
<211> LENGTH: 53
<212> TYPE: DNA
<213> ORGANISM: Artificial Sequence
<220> FEATURE:
<223> OTHER INFORMATION: Synthetic sequence

<400> SEQUENCE: 131
tcgctgctgc tcgccgtgac gcaggaccccc atctccggga tatgcatctc cga          53

<210> SEQ ID NO 132
<211> LENGTH: 23
<212> TYPE: DNA
<213> ORGANISM: Artificial Sequence
<220> FEATURE:
<223> OTHER INFORMATION: Synthetic sequence

<400> SEQUENCE: 132
tcgctgctgc tcgccgtgac gca                                            23

<210> SEQ ID NO 133
<211> LENGTH: 24
<212> TYPE: DNA
<213> ORGANISM: Artificial Sequence
<220> FEATURE:
<223> OTHER INFORMATION: Synthetic sequence

<400> SEQUENCE: 133
catctccggg atatgcatct ccga                                           24

<210> SEQ ID NO 134
<211> LENGTH: 23
<212> TYPE: DNA
<213> ORGANISM: Artificial Sequence
<220> FEATURE:
<223> OTHER INFORMATION: Synthetic sequence

<400> SEQUENCE: 134
tcgctgctgc tcgccgtgac gca                                            23

<210> SEQ ID NO 135
<211> LENGTH: 27
<212> TYPE: DNA
<213> ORGANISM: Artificial Sequence
```

```
<220> FEATURE:
<223> OTHER INFORMATION: Synthetic sequence

<400> SEQUENCE: 135
ccccatctcc gggatatgca tctccga                                          27

<210> SEQ ID NO 136
<211> LENGTH: 23
<212> TYPE: DNA
<213> ORGANISM: Artificial Sequence
<220> FEATURE:
<223> OTHER INFORMATION: Synthetic sequence

<400> SEQUENCE: 136
tcgctgctgc tcgccgtgac gca                                              23

<210> SEQ ID NO 137
<211> LENGTH: 23
<212> TYPE: DNA
<213> ORGANISM: Artificial Sequence
<220> FEATURE:
<223> OTHER INFORMATION: Synthetic sequence

<400> SEQUENCE: 137
atctccggga tatgcatctc cga                                              23

<210> SEQ ID NO 138
<211> LENGTH: 24
<212> TYPE: DNA
<213> ORGANISM: Artificial Sequence
<220> FEATURE:
<223> OTHER INFORMATION: Synthetic sequence

<400> SEQUENCE: 138
tcgctgctgc tcgccgtgac gcag                                             24

<210> SEQ ID NO 139
<211> LENGTH: 25
<212> TYPE: DNA
<213> ORGANISM: Artificial Sequence
<220> FEATURE:
<223> OTHER INFORMATION: Synthetic sequence

<400> SEQUENCE: 139
ccatctccgg gatatgcatc tccga                                            25

<210> SEQ ID NO 140
<211> LENGTH: 26
<212> TYPE: DNA
<213> ORGANISM: Artificial Sequence
<220> FEATURE:
<223> OTHER INFORMATION: Synthetic sequence

<400> SEQUENCE: 140
tcgctgctac tcgccgtgac gcaggc                                           26

<210> SEQ ID NO 141
<211> LENGTH: 23
<212> TYPE: DNA
<213> ORGANISM: Artificial Sequence
<220> FEATURE:
<223> OTHER INFORMATION: Synthetic sequence

<400> SEQUENCE: 141
atctccggga tatgcatctc cga                                              23
```

```
<210> SEQ ID NO 142
<211> LENGTH: 53
<212> TYPE: DNA
<213> ORGANISM: Artificial Sequence
<220> FEATURE:
<223> OTHER INFORMATION: Synthetic sequence

<400> SEQUENCE: 142
tcgctgctgc tcgccgtgac gcaggaccca atctccggga tatgcatctc cga          53

<210> SEQ ID NO 143
<211> LENGTH: 26
<212> TYPE: DNA
<213> ORGANISM: Artificial Sequence
<220> FEATURE:
<223> OTHER INFORMATION: Synthetic sequence

<400> SEQUENCE: 143
tcgctgctgc tcgccgtgac gcagga                                        26

<210> SEQ ID NO 144
<211> LENGTH: 23
<212> TYPE: DNA
<213> ORGANISM: Artificial Sequence
<220> FEATURE:
<223> OTHER INFORMATION: Synthetic sequence

<400> SEQUENCE: 144
atctccggga tatgcatctc cga                                           23

<210> SEQ ID NO 145
<211> LENGTH: 23
<212> TYPE: DNA
<213> ORGANISM: Artificial Sequence
<220> FEATURE:
<223> OTHER INFORMATION: Synthetic sequence

<400> SEQUENCE: 145
tcgctgctgc tcgccgtgac gca                                           23

<210> SEQ ID NO 146
<211> LENGTH: 23
<212> TYPE: DNA
<213> ORGANISM: Artificial Sequence
<220> FEATURE:
<223> OTHER INFORMATION: Synthetic sequence

<400> SEQUENCE: 146
atctccggga tatgcatctc cga                                           23

<210> SEQ ID NO 147
<211> LENGTH: 26
<212> TYPE: DNA
<213> ORGANISM: Artificial Sequence
<220> FEATURE:
<223> OTHER INFORMATION: Synthetic sequence

<400> SEQUENCE: 147
tcgctgctgc tcgccgtgac gcaggc                                        26

<210> SEQ ID NO 148
<211> LENGTH: 18
<212> TYPE: DNA
<213> ORGANISM: Artificial Sequence
<220> FEATURE:
<223> OTHER INFORMATION: Synthetic sequence
```

```
<400> SEQUENCE: 148
cgggatatgc atctccga                                                          18

<210> SEQ ID NO 149
<211> LENGTH: 21
<212> TYPE: DNA
<213> ORGANISM: Artificial Sequence
<220> FEATURE:
<223> OTHER INFORMATION: Synthetic sequence

<400> SEQUENCE: 149
tcgctgctgc tcgccgtcac g                                                      21

<210> SEQ ID NO 150
<211> LENGTH: 22
<212> TYPE: DNA
<213> ORGANISM: Artificial Sequence
<220> FEATURE:
<223> OTHER INFORMATION: Synthetic sequence

<400> SEQUENCE: 150
tctccgggat atgcatctcc ca                                                     22

<210> SEQ ID NO 151
<211> LENGTH: 25
<212> TYPE: DNA
<213> ORGANISM: Artificial Sequence
<220> FEATURE:
<223> OTHER INFORMATION: Synthetic sequence

<400> SEQUENCE: 151
tcgctgctgc tcgccgtgac gcagg                                                  25

<210> SEQ ID NO 152
<211> LENGTH: 26
<212> TYPE: DNA
<213> ORGANISM: Artificial Sequence
<220> FEATURE:
<223> OTHER INFORMATION: Synthetic sequence

<400> SEQUENCE: 152
cccatctccg ggatatgcat ctccga                                                 26

<210> SEQ ID NO 153
<211> LENGTH: 27
<212> TYPE: DNA
<213> ORGANISM: Artificial Sequence
<220> FEATURE:
<223> OTHER INFORMATION: Synthetic sequence

<400> SEQUENCE: 153
tcgctgctgc tcgccgtgac gcaggac                                                27

<210> SEQ ID NO 154
<211> LENGTH: 24
<212> TYPE: DNA
<213> ORGANISM: Artificial Sequence
<220> FEATURE:
<223> OTHER INFORMATION: Synthetic sequence

<400> SEQUENCE: 154
aatctccggg atatgcatct ccga                                                   24

<210> SEQ ID NO 155
```

```
<211> LENGTH: 24
<212> TYPE: DNA
<213> ORGANISM: Artificial Sequence
<220> FEATURE:
<223> OTHER INFORMATION: Synthetic sequence

<400> SEQUENCE: 155
tcgctgctgc tcgccgtcac gcag                                          24

<210> SEQ ID NO 156
<211> LENGTH: 22
<212> TYPE: DNA
<213> ORGANISM: Artificial Sequence
<220> FEATURE:
<223> OTHER INFORMATION: Synthetic sequence

<400> SEQUENCE: 156
tctccgggat atgcatctcc ca                                            22

<210> SEQ ID NO 157
<211> LENGTH: 25
<212> TYPE: DNA
<213> ORGANISM: Artificial Sequence
<220> FEATURE:
<223> OTHER INFORMATION: Synthetic sequence

<400> SEQUENCE: 157
tcgctgctgc tcgccgtgac gcagg                                         25

<210> SEQ ID NO 158
<211> LENGTH: 26
<212> TYPE: DNA
<213> ORGANISM: Artificial Sequence
<220> FEATURE:
<223> OTHER INFORMATION: Synthetic sequence

<400> SEQUENCE: 158
cccatctccg ggatatgcat ctccga                                        26

<210> SEQ ID NO 159
<211> LENGTH: 22
<212> TYPE: DNA
<213> ORGANISM: Artificial Sequence
<220> FEATURE:
<223> OTHER INFORMATION: Synthetic sequence

<400> SEQUENCE: 159
tcgctgctgc tcgccgtcac gc                                            22

<210> SEQ ID NO 160
<211> LENGTH: 28
<212> TYPE: DNA
<213> ORGANISM: Artificial Sequence
<220> FEATURE:
<223> OTHER INFORMATION: Synthetic sequence

<400> SEQUENCE: 160
acccaatctc cgggatatgc atctccca                                      28

<210> SEQ ID NO 161
<211> LENGTH: 12
<212> TYPE: DNA
<213> ORGANISM: Artificial Sequence
<220> FEATURE:
<223> OTHER INFORMATION: Synthetic sequence

<400> SEQUENCE: 161
```
tcgctgctgc tc                                                       12

<210> SEQ ID NO 162
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: n is a, c, g, or t

<400> SEQUENCE: 162 catctccgan                                                          10

<210> SEQ ID NO 163
<211> LENGTH: 26
<212> TYPE: DNA
<213> ORGANISM: Artificial Sequence
<220> FEATURE:
<223> OTHER INFORMATION: Synthetic sequence

<400> SEQUENCE: 163
tcgctgctgc tcgccgtgac gcagga                                        26

<210> SEQ ID NO 164
<211> LENGTH: 27
<212> TYPE: DNA
<213> ORGANISM: Artificial Sequence
<220> FEATURE:
<223> OTHER INFORMATION: Synthetic sequence

<400> SEQUENCE: 164
ccccatctcc gggatatgca tctccga                                       27

<210> SEQ ID NO 165
<211> LENGTH: 26
<212> TYPE: DNA
<213> ORGANISM: Artificial Sequence
<220> FEATURE:
<223> OTHER INFORMATION: Synthetic sequence

<400> SEQUENCE: 165
tcgctgctgc tcgccgtgac gcagga                                        26

<210> SEQ ID NO 166
<211> LENGTH: 16
<212> TYPE: DNA
<213> ORGANISM: Artificial Sequence
<220> FEATURE:
<223> OTHER INFORMATION: Synthetic sequence

<400> SEQUENCE: 166
ggatatgcat ctccga                                                   16

<210> SEQ ID NO 167
<211> LENGTH: 25
<212> TYPE: DNA
<213> ORGANISM: Artificial Sequence
<220> FEATURE:
<223> OTHER INFORMATION: Synthetic sequence

<400> SEQUENCE: 167
caatctccgg gatatgcatc tccca                                         25

<210> SEQ ID NO 168
<211> LENGTH: 26
<212> TYPE: DNA
<213> ORGANISM: Artificial Sequence
<220> FEATURE:
<223> OTHER INFORMATION: Synthetic sequence

<400> SEQUENCE: 168
tcgctgctgc tcgccgtgac gcagga                                          26

<210> SEQ ID NO 169
<211> LENGTH: 27
<212> TYPE: DNA
<213> ORGANISM: Artificial Sequence
<220> FEATURE:
<223> OTHER INFORMATION: Synthetic sequence

<400> SEQUENCE: 169
ccccatctcc gggatatgca tctccga                                         27

<210> SEQ ID NO 170
<211> LENGTH: 26
<212> TYPE: DNA
<213> ORGANISM: Artificial Sequence
<220> FEATURE:
<223> OTHER INFORMATION: Synthetic sequence

<400> SEQUENCE: 170
tcgctgctgc tcgccgtgac gcagga                                          26

<210> SEQ ID NO 171
<211> LENGTH: 16
<212> TYPE: DNA
<213> ORGANISM: Artificial Sequence
<220> FEATURE:
<223> OTHER INFORMATION: Synthetic sequence

<400> SEQUENCE: 171
ggatatgcat ctccga                                                     16

<210> SEQ ID NO 172
<211> LENGTH: 23
<212> TYPE: DNA
<213> ORGANISM: Artificial Sequence
<220> FEATURE:
<223> OTHER INFORMATION: Synthetic sequence

<400> SEQUENCE: 172
ccgtcacgca ggacccaatc tcc                                             23

<210> SEQ ID NO 173
<211> LENGTH: 10
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(10)
<223> OTHER INFORMATION: n is a, c, g, or t

<400> SEQUENCE: 173 ccgtcannnn                                                            10

<210> SEQ ID NO 174
<211> LENGTH: 16

```
<212> TYPE: DNA
<213> ORGANISM: Artificial Sequence
<220> FEATURE:
<223> OTHER INFORMATION: Synthetic sequence

<400> SEQUENCE: 174
gcaggaccca atctcc                                                    16

<210> SEQ ID NO 175
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(10)
<223> OTHER INFORMATION: n is a, c, g, or t

<400> SEQUENCE: 175 ccgtcannnn                                                           10

<210> SEQ ID NO 176
<211> LENGTH: 11
<212> TYPE: DNA
<213> ORGANISM: Artificial Sequence
<220> FEATURE:
<223> OTHER INFORMATION: Synthetic sequence

<400> SEQUENCE: 176
acccaatctc c                                                         11

<210> SEQ ID NO 177
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(10)
<223> OTHER INFORMATION: n is a, c, g, or t

<400> SEQUENCE: 177 ccgtnnnnnn                                                           10

<210> SEQ ID NO 178
<211> LENGTH: 12
<212> TYPE: DNA
<213> ORGANISM: Artificial Sequence
<220> FEATURE:
<223> OTHER INFORMATION: Synthetic sequence

<400> SEQUENCE: 178
gacccaatct cc                                                        12

<210> SEQ ID NO 179
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(10)
<223> OTHER INFORMATION: n is a, c, g, or t

<400> SEQUENCE: 179
```
ccgtcacnnn 10

<210> SEQ ID NO 180
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(10)
<223> OTHER INFORMATION: n is a, c, g, or t

<400> SEQUENCE: 180 ctccnnnnnn 10

<210> SEQ ID NO 181
<211> LENGTH: 52
<212> TYPE: DNA
<213> ORGANISM: Artificial Sequence
<220> FEATURE:
<223> OTHER INFORMATION: Synthetic sequence

<400> SEQUENCE: 181
tcgctgctgc tcgccgtcac gcaggaccca atctccggat atgcatctcc ca 52

<210> SEQ ID NO 182
<211> LENGTH: 19
<212> TYPE: DNA
<213> ORGANISM: Artificial Sequence
<220> FEATURE:
<223> OTHER INFORMATION: Synthetic sequence

<400> SEQUENCE: 182
tcgctgctgc tcgccgtca 19

<210> SEQ ID NO 183
<211> LENGTH: 30
<212> TYPE: DNA
<213> ORGANISM: Artificial Sequence
<220> FEATURE:
<223> OTHER INFORMATION: Synthetic sequence

<400> SEQUENCE: 183
aggacccaat ctccggatat gcatctccca 30

<210> SEQ ID NO 184
<211> LENGTH: 19
<212> TYPE: DNA
<213> ORGANISM: Artificial Sequence
<220> FEATURE:
<223> OTHER INFORMATION: Synthetic sequence

<400> SEQUENCE: 184
tcgctgctgc tcgccgtca 19

<210> SEQ ID NO 185
<211> LENGTH: 31
<212> TYPE: DNA
<213> ORGANISM: Artificial Sequence
<220> FEATURE:
<223> OTHER INFORMATION: Synthetic sequence

<400> SEQUENCE: 185
caggacccaa tctccggata tgcatctccc a 31

<210> SEQ ID NO 186
<211> LENGTH: 19
<212> TYPE: DNA
<213> ORGANISM: Artificial Sequence
<220> FEATURE:
<223> OTHER INFORMATION: Synthetic sequence

<400> SEQUENCE: 186
tcgctgctgc tcgccgtca                                                  19

<210> SEQ ID NO 187
<211> LENGTH: 29
<212> TYPE: DNA
<213> ORGANISM: Artificial Sequence
<220> FEATURE:
<223> OTHER INFORMATION: Synthetic sequence

<400> SEQUENCE: 187
ggacccaatc tccggatatg catctccca                                       29

<210> SEQ ID NO 188
<211> LENGTH: 53
<212> TYPE: DNA
<213> ORGANISM: Artificial Sequence
<220> FEATURE:
<223> OTHER INFORMATION: Synthetic sequence

<400> SEQUENCE: 188
tcgctgctgc tcgccgtcat cgcaggaccc aatctccgga tatgcatctc cca            53

<210> SEQ ID NO 189
<211> LENGTH: 1606
<212> TYPE: DNA
<213> ORGANISM: Artificial Sequence
<220> FEATURE:
<223> OTHER INFORMATION: Synthetic sequence

<400> SEQUENCE: 189
tcgctgctgc tcgccgtgac gcaggacccc atctccggga tatgcatctc cgaaagcttg     60
tcgacggatc catggtgagc aagggcgagg agctgttcac cggggtggtg cccatcctgg    120
tcgagctgga cggcgacgta aacggccaca gttcagcgt gtccggcgag ggcgagggcg    180
atgccaccta cggcaagctg accctgaagt tcatctgcac caccggcaag ctgcccgtgc    240
cctggcccac cctcgtgacc accttcacct acggcgtgca gtgcttcagc cgctaccccg    300
accacatgaa gcagcacgac ttcttcaagt ccgccatgcc cgaaggctac gtccaggagc    360
gcaccatctt cttcaaggac gacggcaact acaagacccg cgccgaggtg aagttcgagg    420
gcgacaccct ggtgaaccgc atcgagctga agggcatcga cttcaaggag gacggcaaca    480
tcctggggca caagctggag tacaactaca acagccacaa cgtctatatc atggccgaca    540
agcagaagaa cggcatcaag gtgaacttca gatccgcca caacatcgag gacggcagcg    600
tgcagctcgc cgaccactac cagcagaaca cccccatcgg cgacggcccc gtgctgctgc    660
ccgacaacca ctacctgagc acccagtccg ccctgagcaa agaccccaac gagaagcgcg    720
atcacatggt cctgctggag ttcgtgaccg ccgccgggat cactcacggc atggacgagc    780
tgtacaagta accgggcgag ctcgaattcg ctgaaatcac cagtctctct ctacaaatct    840
atctctctct attttctcca taaataatgt gtgagtagtt tcccgataag gaaattagg    900 gttcttatag ggtttcgctc atgtgttgag catataagaa acccttagta tgtatttgta    960
tttgtaaaat acttctatca ataaaatttc taattcctaa aaccaaaatc cagtactaaa    1020

```
atccagatct cctaaagtcc ctatagatct ttgtcgtgaa tataaaccag acacgagacg    1080
actaaacctg gagcccagac gccgttcgaa gctagaagta ccgcttaggc aggaggccgt    1140
tagggaaaag atgctaaggc agggttggtt acgttgactc ccccgtaggt ttggtttaaa    1200
tatgatgaag tggacggaag gaaggaggaa gacaaggaag gataaggttg caggccctgt    1260
gcaaggtaag aagatggaaa tttgatagag gtacgctact atacttatac tatacgctaa    1320
gggaatgctt gtatttatac cctatacccc ctaataaccc cttatcaatt taagaaataa    1380
tccgcataag cccccgctta aaaattggta tcagagccat gaataggtct atgaccaaaa    1440
ctcaagagga taaaacctca ccaaaatacg aaagagttct taactctaaa gataaaagat    1500
ctttcaagat caaaactagt tccctcacac cggtgacggg gatcgcatgc gattcgctgc    1560
tgctcgccgt gacgcaggac cccatctccg ggatatgcat ctccga                  1606
```